United States Patent [19]

Shturman et al.

[11] Patent Number: 5,893,857

[45] Date of Patent: Apr. 13, 1999

[54] HANDLE FOR ATHERECTOMY DEVICE

[75] Inventors: Leonid Shturman, Minnetonka, Minn.; Georgiy Morov, Moscow, Russian Federation

[73] Assignee: Shturman Cardiology Systems, Inc., Minneapolis, Minn.

[21] Appl. No.: 08/785,991

[22] Filed: Jan. 21, 1997

[51] Int. Cl.⁶ .......................... A61B 17/22; A61B 17/14
[52] U.S. Cl. .................................. 606/159; 606/180
[58] Field of Search ......................... 606/1, 159, 167, 606/170, 171, 174, 180–185

[56] References Cited

U.S. PATENT DOCUMENTS 5,287,858  2/1994  Hammerslag et al. ............... 606/180
5,314,407  5/1994  Auth et al. ............................ 606/159

*Primary Examiner*—Glenn K. Dawson
*Attorney, Agent, or Firm*—Gregory P. Kaihoi

[57] ABSTRACT

The invention provides a handle for a rotational atherectomy device, the handle including a guide wire clamp and a turbine brake operatively interconnected with the guide wire clamp so that the brake automatically prevents rotation of the turbine when the guide wire is unclamped. The brake is movable from a brake-released position to a brake-engaged position, in which position the brake prevents rotation of the turbine. A manual override is also provided, permitting unclamping of the guide wire independent of the position of the brake.

182 Claims, 31 Drawing Sheets

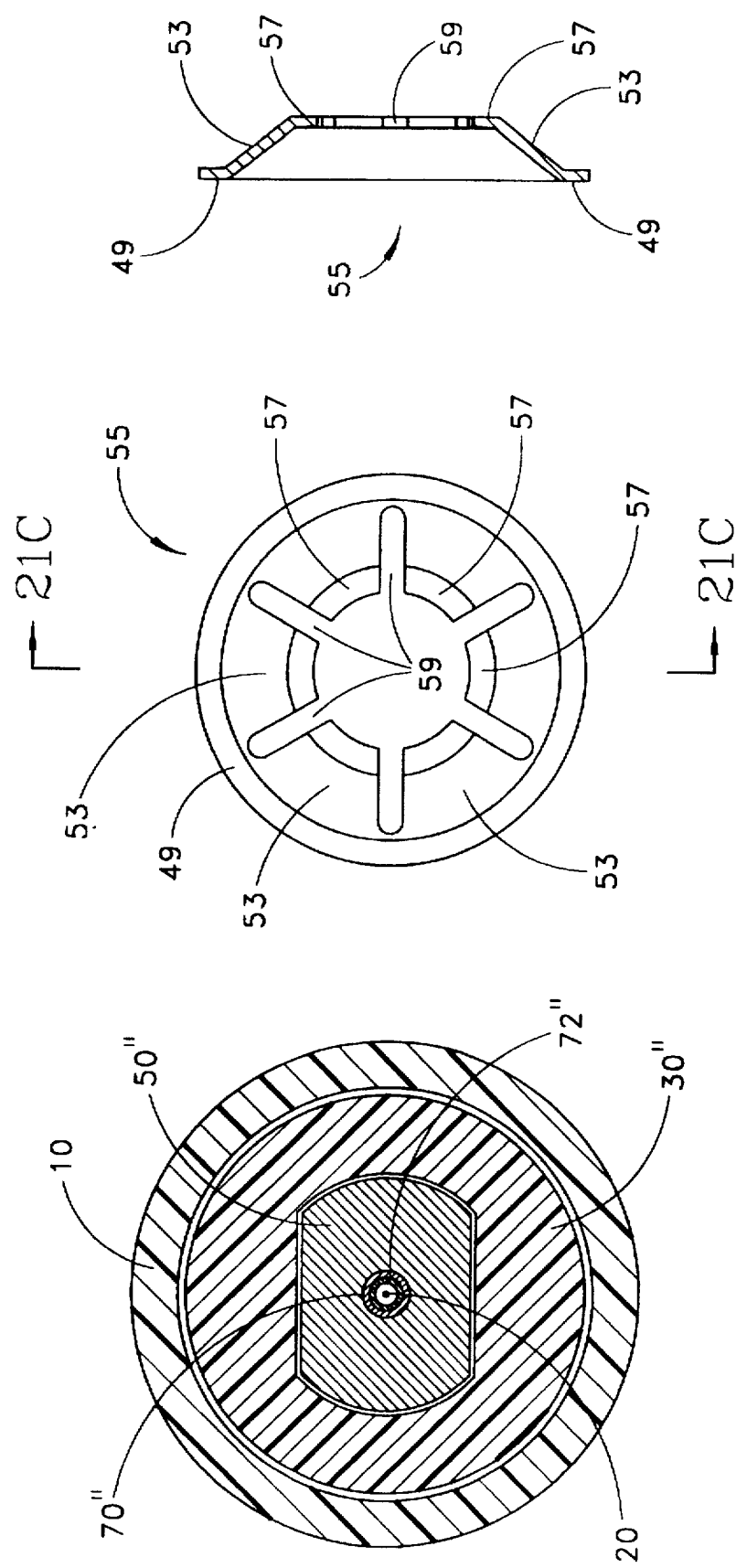

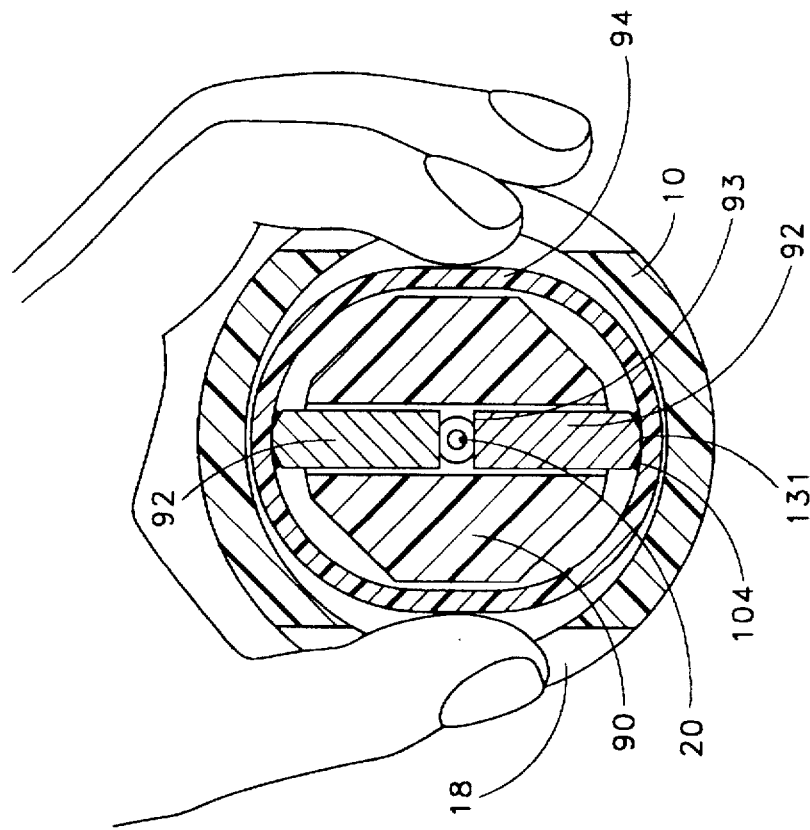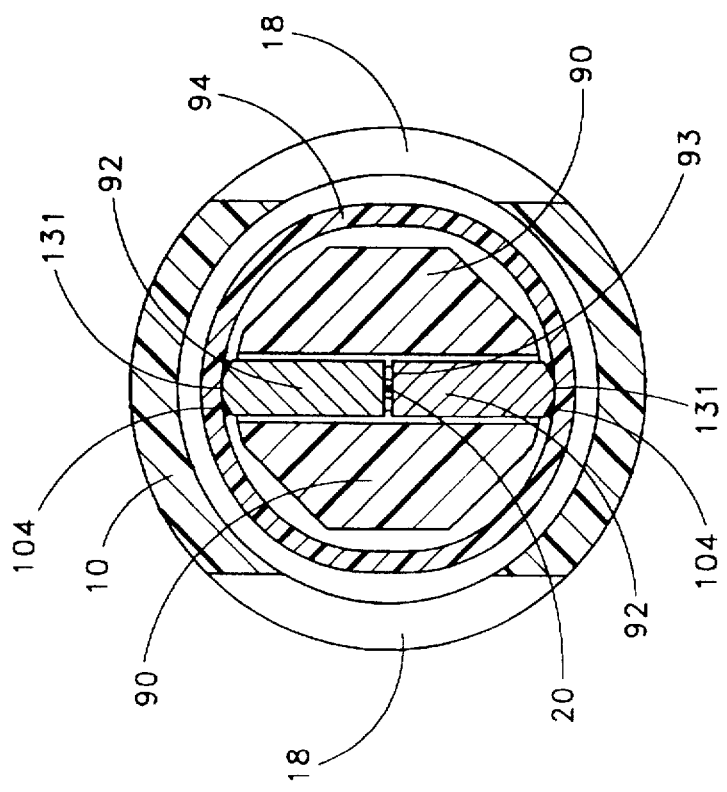

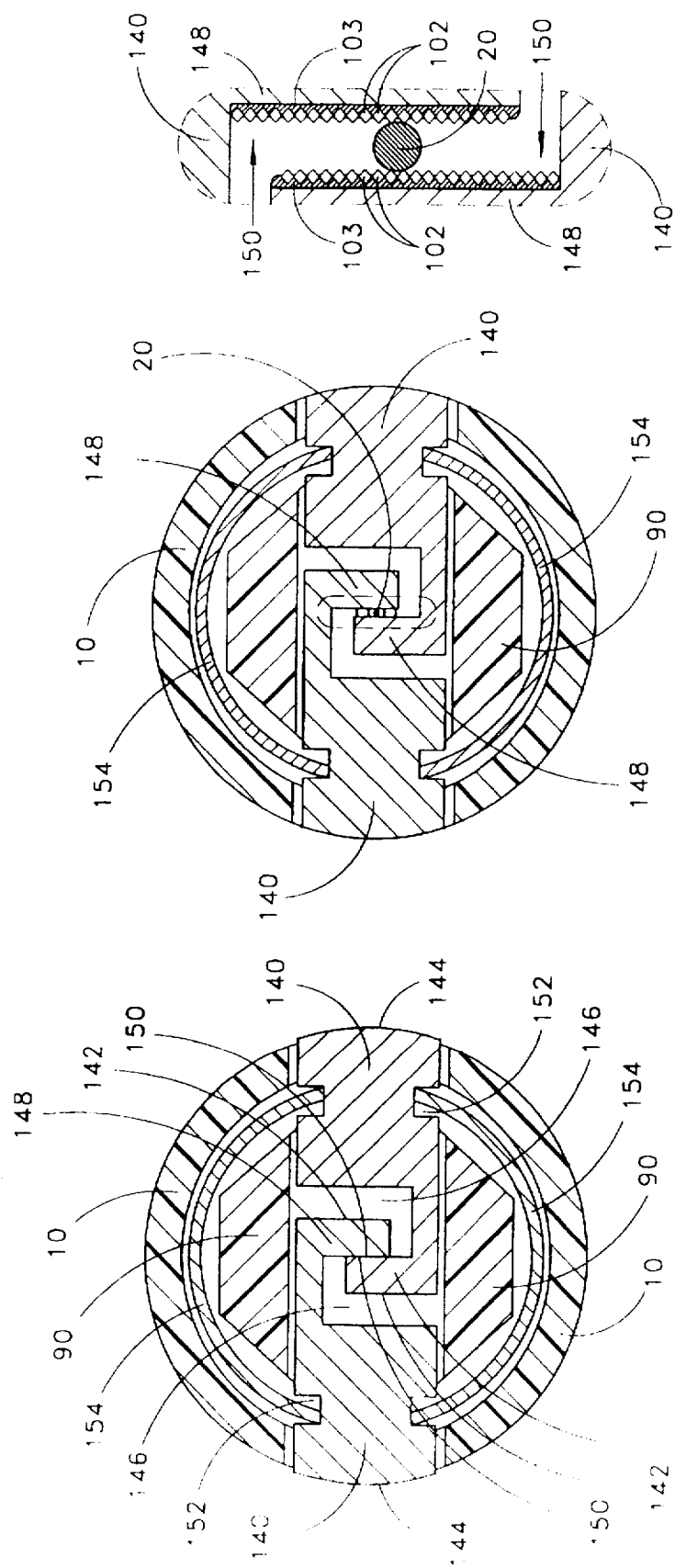

HANDLE FOR ATHERECTOMY DEVICE

TECHNICAL FIELD

The invention relates to devices and methods for removing tissue from body passageways, such as removal of atherosclerotic plaque from arteries, utilizing a rotational atherectomy device. In particular, the invention relates to improvements in a handle for a rotational atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®.

The Rotablator® device is depicted in FIG. 1, and includes a compressed gas driven turbine located inside a handle housing A. The compressed gas driven turbine is connected to a drive shaft B having an abrasive coated burr C at its distal end. The drive shaft and the burr are rotated at high speeds, typically in the range of, e.g., about 150,000 to about 190,000 rpms. The drive shaft is designed to be advanced over and rotated around a guide wire D. For most of its length the drive shaft is disposed inside a catheter E. The guide wire D must be clamped in some fashion to prevent it from rotating when the turbine and drive shaft are rotated, because uncontrolled rotation of the very flexible distal end portion of the guide wire could cause damage to the artery. For that purpose the Rotablator® device includes a pneumatic guide wire clamp built into the proximal end portion of the handle housing A. Compressed gas is supplied to the pneumatic guide wire clamp by a flexible gas supply tube F. This gas supply tube F is connected to a rigid conduit G (shown in FIGS. 3-5) that extends through the handle housing A and is connected to a flexible U-shaped tube H which supplies compressed gas to the turbine.

Under certain circumstances, however, it is desirable to override the guide wire clamp and release the guide wire from the clamp even when the turbine and the drive shaft are rotated. For example, it is useful to do so when both the drive shaft and the catheter are advanced over the guide wire to a position within a human artery or when they are removed from the human body. Sometimes it is also useful to override the guide wire clamp to permit advancement or retraction of the guide wire within the rotating drive shaft.

The proximal end portion of the handle of the Rotablator® device is shown in FIG. 2, and the details of the pneumatic guide wire clamp are shown in FIGS. 3-5. The clamp includes a pair of clamping blocks I on opposite sides of the guide wire. Each clamping block has an inner surface for engaging the guide wire D. Each clamping block also has an outer, tapered surface. A movable pneumatic piston L is provided within the handle, the piston having a proximal end with a central tapered portion in alignment with the outer tapered surfaces of the clamping blocks I.

A coil spring M is provided to normally bias the piston L distally away from the clamping blocks I, thus releasing the guide wire D from the clamp. FIG. 3 shows the clamp in this released position. When compressed gas is provided to a piston chamber N on the distal side of the piston L, the compressed gas urges the piston L proximally, overcoming the force of the spring M and moving the piston into the position shown in FIG. 4. (In FIGS. 4-5 the path of the compressed gas is shown by arrows.) As can be seen in FIG. 4, the tapered proximal end of the piston L presses against the complementary tapered surfaces of the clamping blocks I, resulting in a compression force exerted by the clamping blocks I against the guide wire D. Thus, when compressed gas is supplied to the piston chamber N, the clamping blocks I clamp the guide wire D to prevent rotation or longitudinal movement of the guide wire D. When the supply of compressed gas to the Rotablator® atherectomy device is interrupted and, as a result, the gas pressure is released from the piston chamber N, the spring M returns the piston L to its distal position (FIG. 3), releasing pressure on the clamping blocks I and the guide wire D.

The Rotablator® device is constructed so that the piston chamber N is connected pneumatically to the compressed gas tube F that powers both the pneumatic guide wire clamp and the rotatable turbine. The compressed gas supply tube F is connected on one side of the handle housing A to the conduit G positioned inside the handle housing. The conduit G conducts the compressed gas across the handle housing into the flexible U-shaped tube H which supplies the compressed gas to the turbine. Fittings P are used to connect the gas supply tube F and the U-shaped tube H to the conduit G. The conduit G in the handle housing is pneumatically connected to internal passageways which conduct the compressed gas to the piston chamber N. Thus, whenever compressed gas is provided through gas supply tube F to rotate the turbine (and, therefore, the drive shaft of the atherectomy device), the compressed gas is also provided to the piston chamber N to clamp the guide wire D.

An override mechanism is provided to permit the user to release the guide wire clamp even when the compressed gas is supplied to the Rotablator® atherectomy device and the drive shaft is rotating. This override mechanism consists of a movable spool-type valve R which can be moved from the position shown in FIGS. 3–4 to the position shown in FIG. 5 by pressing on the override button S. In the position shown in FIG. 5, one end of the spool valve R has been moved to a position where it interrupts the supply of compressed gas pressure to the piston chamber N. In this position the spool valve R also vents the piston chamber N to the surrounding atmosphere, releasing the pressure on the piston L and allowing the spring M to return the piston L to its distal position, releasing the clamp even though compressed gas is supplied to rotate the turbine. The spool valve R is biased by a valve spring T to return to the position shown in FIGS. 3–4 when manual pressure on the override button S is released.

The Rotablator® device's drive shaft begins to rotate very quickly when compressed gas is supplied to the turbine. Because its guide wire clamp can be activated only by supplying compressed gas to the turbine, the drive shaft may begin rotating, and may cause the guide wire D to begin to rotate, before the clamp has been fully activated (i.e., before the force of the spring M has been overcome and the piston L has been moved a sufficient distance to engage the clamping blocks I tightly against the guide wire D to prevent it from rotating). Thus, the Rotablator® clamp is not always as fast in its action as would be desirable. Moreover, the Rotablator® device does not provide a brake to prevent the rotation of the turbine and drive shaft when the guide wire clamp is released.

SUMMARY OF THE INVENTION

The invention provides a handle for a rotational atherectomy device, the handle including a guide wire clamp and a turbine brake operatively interconnected with the guide wire clamp so that the brake automatically prevents rotation of the turbine when the guide wire is unclamped. The brake is movable from a brake-released position to a brake-engaged position, in which position the brake prevents rotation of the turbine. A manual override is also provided, permitting unclamping of the guide wire independent of the position of the brake.

The device includes a handle housing and a turbine carriage carrying a rotatable turbine. The device also includes a rotatable drive shaft with an abrasive implement at its distal end. The proximal end of the rotatable drive shaft is connected to and rotated by the turbine.

Preferably the turbine carriage is movable longitudinally with respect to the handle from a turbine carriage-locked position, in which position the turbine carriage is restrained from longitudinal movement with respect to the handle, to a range of turbine carriage-unlocked positions, in which positions longitudinal movement of the turbine carriage with respect to the handle is substantially not restrained. A turbine carriage lock is provided for automatically restraining the turbine carriage from longitudinal movement with respect to the handle when the turbine carriage is moved longitudinally to the turbine carriage-locked position.

The brake preferably includes a brake shoe carried by the turbine carriage. The brake shoe is selectively movable between a brake shoe-released position and a brake shoe-engaged position, in which position the brake shoe is engaged with the turbine to prevent rotation of the turbine and the drive shaft.

In a preferred embodiment the clamp comprises a pair of opposed clamping blocks and a resilient collar encircling the clamping blocks. The resilient collar biases the clamping blocks toward each other, thereby clamping the guide wire between the clamping blocks. The handle of the atherectomy device also includes a clamp control mechanism for controlling the position of the clamp. Preferably the clamp control mechanism is comprised of a clamp control tube having a lumen for receiving the guide wire therethrough, the clamp control tube having a distal end portion connected to the brake shoe (and thus to the turbine carriage). The clamp control tube is movable longitudinally from a range of positions where its proximal end portion is spaced from the clamping blocks to a position where its proximal end portion is wedged between the clamping blocks, moving the clamp to a guide wire-released position.

In a preferred embodiment the clamp control tube, the brake shoe and the turbine carriage preferably are operatively interconnected so that:

(1) when the turbine carriage is moved into its turbine carriage-locked position the brake shoe becomes engaged with the turbine, preventing it from rotating, and the clamp control tube becomes wedged between the clamping blocks, releasing the guide wire from the clamp; and (2) when the turbine carriage is moved into its range of turbine carriage-unlocked positions the clamp control tube is moved away from the clamping blocks so that the guide wire is clamped between the clamping blocks of the guide wire clamp and the brake shoe is moved into its brake shoe-release position permitting the turbine to rotate.

Preferably the clamp control tube, the brake shoe and the turbine carriage are operatively interconnected so that as the turbine carriage is moved toward its turbine carriage-locked position the brake shoe reaches its brake shoe-engaged position preventing rotation of the turbine before the clamp control tube is wedged between the clamping blocks, thereby releasing the guide wire from the clamp. Similarly, as the turbine carriage is moved out of the turbine carriage-locked position into the range of turbine carriage-unlocked positions the clamp is moved into its guide wire-clamped position before the brake is released.

BRIEF DESCRIPTION OF THE DRAWINGS

FIG. 8A is an enlarged view of a portion of FIG. 8 shown in longitudinal cross-section;

FIG. 9A is an enlarged view of a portion of FIG. 9 shown in longitudinal cross-section;

FIG. 21A is a cross-sectional view of FIGS. 19 and 20, taken along lines 21A—21A thereof;

FIG. 21B is a plan view of a disk-shaped leaf spring utilized in the embodiment depicted in FIGS. 19-20;

FIG. 21C is a cross-sectional view of FIG. 21B, taken along lines 21C—21C thereof;

FIG. 25A is a transverse cross-sectional view of the clamp portion of an atherectomy device of the invention;

FIG. 25B is a transverse cross-sectional view of the clamp portion of the atherectomy device of FIG. 25A, shown in a moved position;

FIG. 34A depicts another embodiment of clamping blocks and a clamp biasing spring usable in the atherectomy device of the invention;

FIG. 34B depicts the clamp of FIG. 34A in a moved position;

FIG. 34C is an enlarged view of a portion of FIG. 34B;

DETAILED DESCRIPTION OF THE INVENTION

Figure 1:
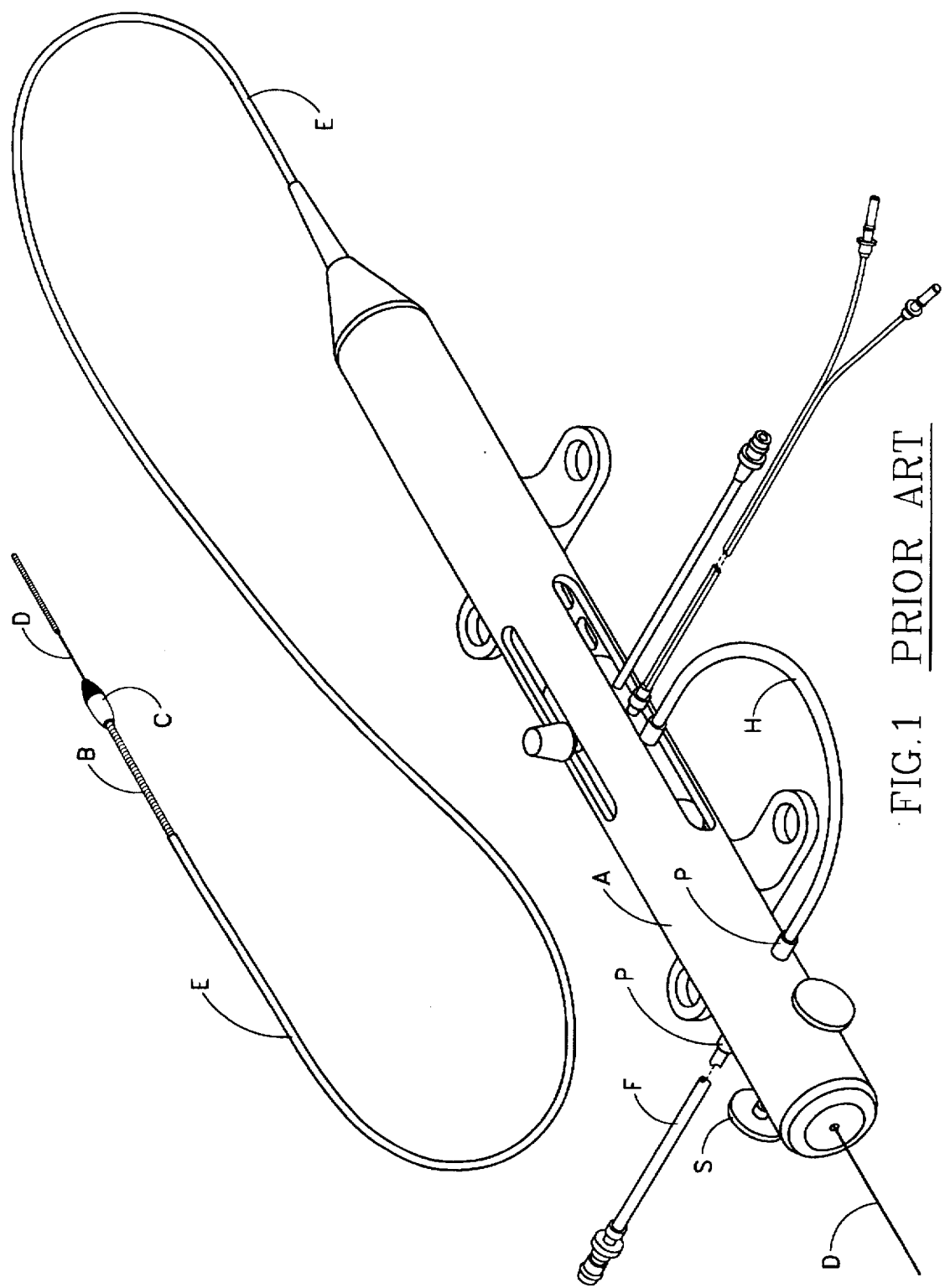
FIG. 1 is a perspective view of the prior art Rotablator® rotational atherectomy device described above.
Figure 2:
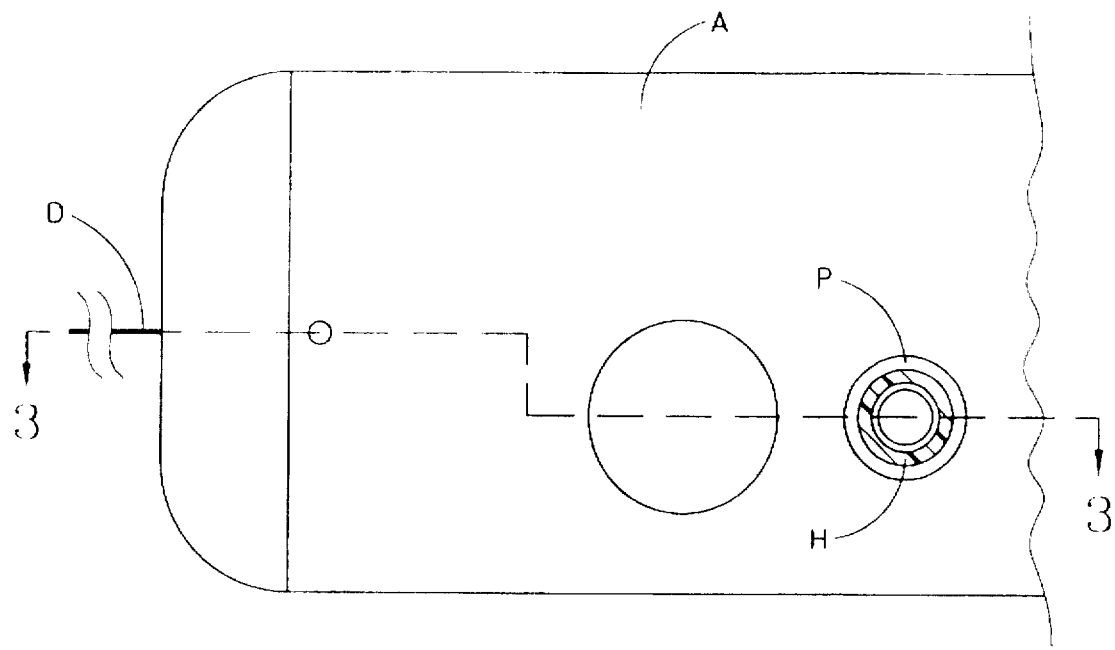
FIG. 2 is a side view of the proximal end portion of handle of the Rotablator® atherectomy device.
Figure 3:
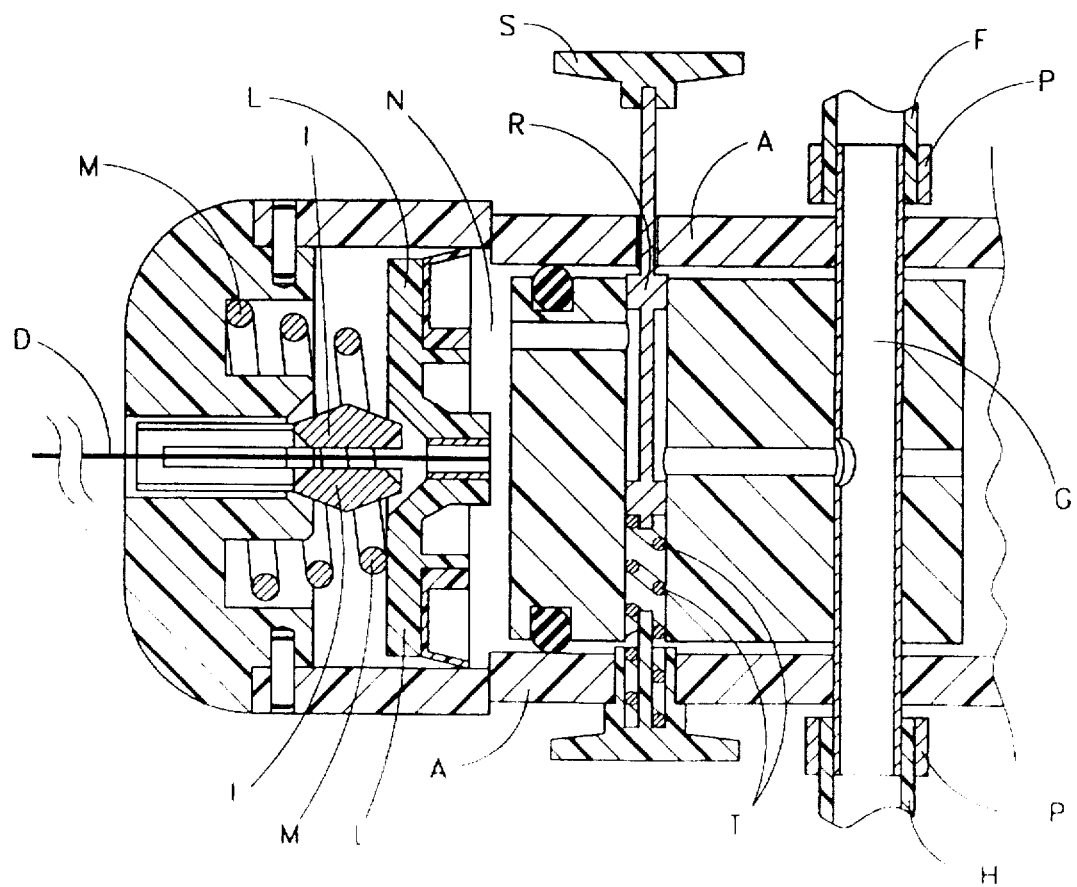
FIG. 3 is a cross-sectional view of FIG. 2, taken along lines 3—3 thereof.
Figure 4:
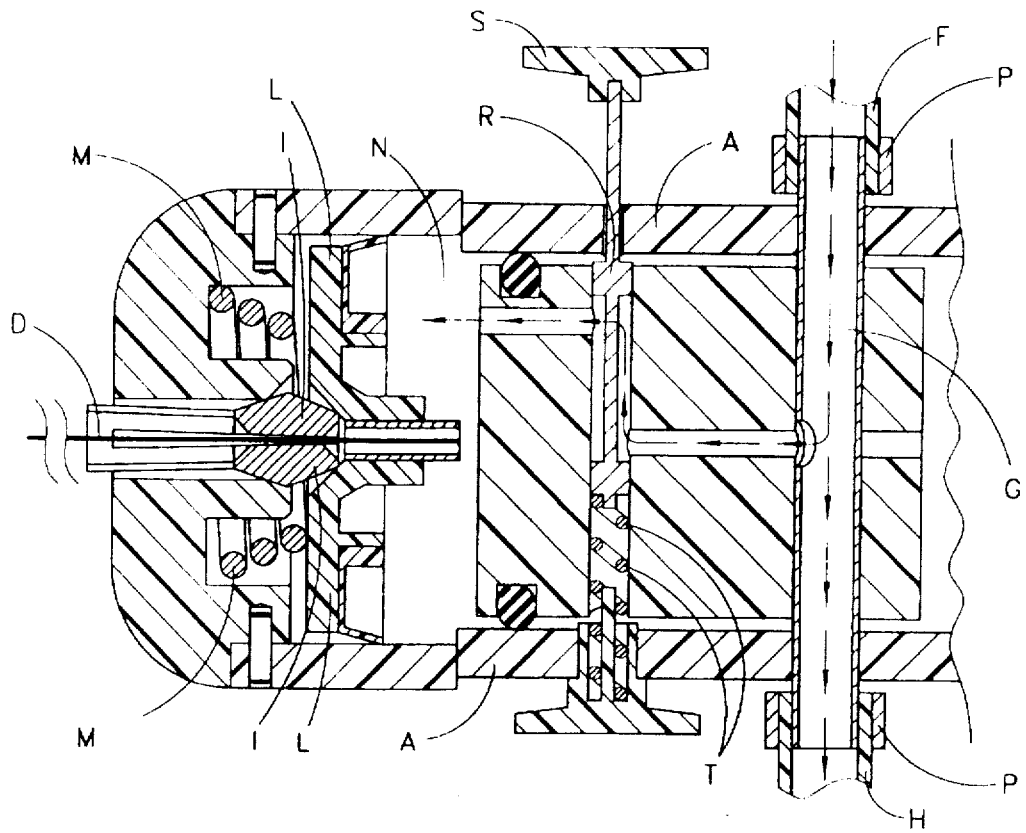
FIG. 4 is a cross-sectional view similar to FIG. 3, showing the pneumatic guide wire clamp of the Rotablator® device in a moved position (compressed gas has been supplied to activate the turbine of the device and its pneumatic guide wire clamp)
Figure 5:
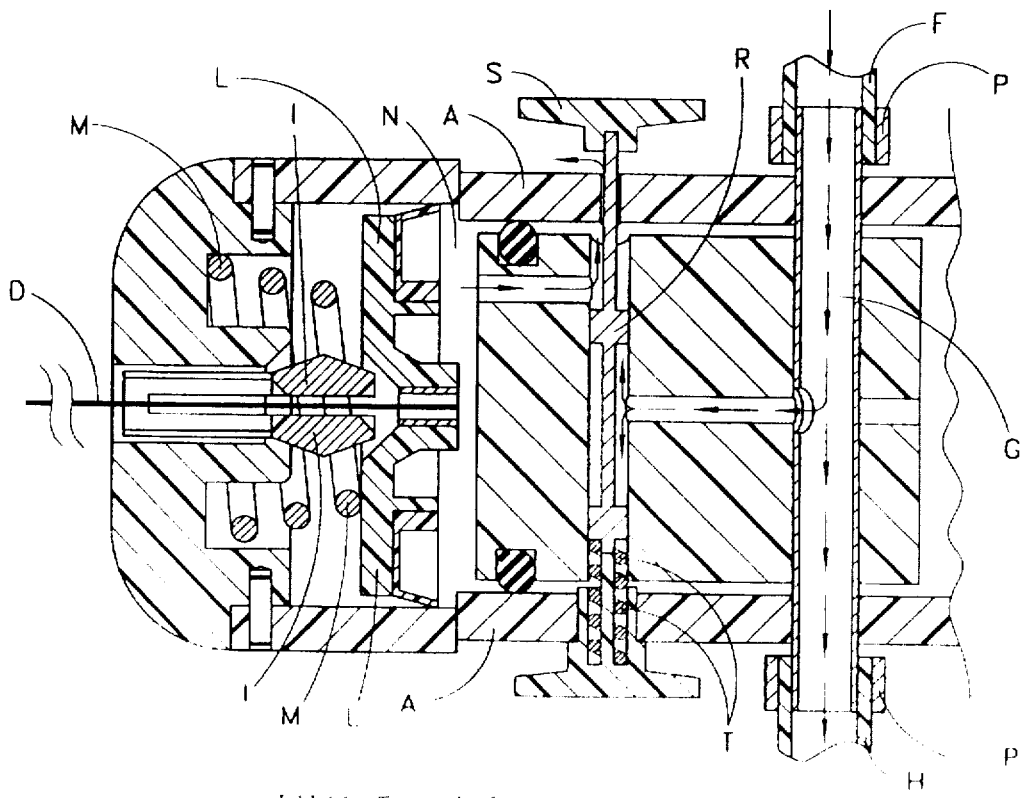
FIG. 5 is another cross-sectional view similar to FIG. 3, showing the guide wire clamp of the Rotablator® device in another moved position (the override button has been depressed to release the pneumatic guide wire clamp)
Figure 6:
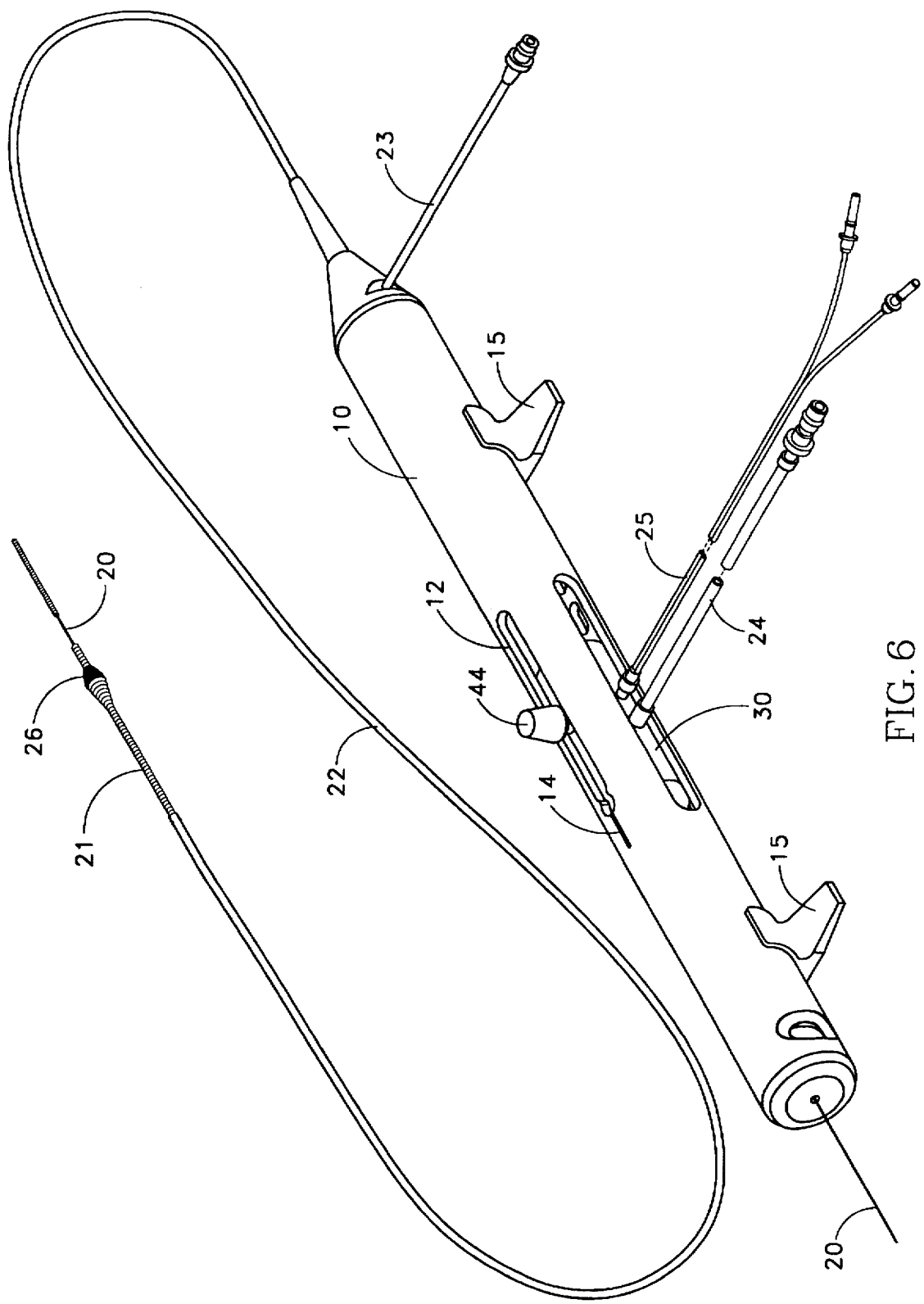
FIG. 6 is a perspective view of a rotational atherectomy device of the invention.

FIG. 6 illustrates in perspective view an atherectomy device of the invention. The device includes a handle having a housing 10, an elongated, flexible drive shaft 21 (typically constructed from multifilar helically coiled wire) having a tissue removal section 26 near its distal end, and an elongated catheter 22 extending distally from the handle housing 10. The catheter 22 has a lumen in which most of the length of the drive shaft 21 is disposed, the tissue removal section 26 extending distally beyond the distal end of the catheter 22. The drive shaft 21 also contains an inner lumen, permitting the drive shaft 21 to be advanced over a guide wire 20, which desirably extends both proximally of the handle housing 10 and distally beyond the drive shaft 21. A fluid supply line 23 may be provided for introducing a cooling and lubricating solution (typically saline or another biocompatible fluid) into the catheter 22.

A rotatable prime mover (such as a compressed gas driven turbine or similar supply of rotational motion) is connected to the proximal end of the drive shaft 21. In the preferred embodiment illustrated in the drawings the prime mover is disposed within the handle housing 10, and it is carried by a prime mover carriage 30 (sometimes referred to as a turbine carriage) which can be moved longitudinally within the handle housing 10 through a limited range of motion. A control knob 44 (secured to the prime mover carriage 30) is provided to facilitate advancing and retracting of the prime mover and rotatable drive shaft 21 with respect to the catheter 22 and the handle housing 10.

Preferably the prime mover is a turbine powered by compressed gas such as compressed nitrogen or compressed air. For this purpose a compressed gas supply line 24 may be provided, the supply line being connected to the turbine carriage 30. A pair of fiber optic cables 25 may also be provided for monitoring the speed of rotation of the turbine and drive shaft 21 (e.g., as described in the Auth '407 patent and implemented in the Rotablator® device). A pair of legs 15 attached to the handle housing 10 is also provided. For the sake of clarity, the legs 15 are not illustrated in many of the other drawings.

Figure 7:
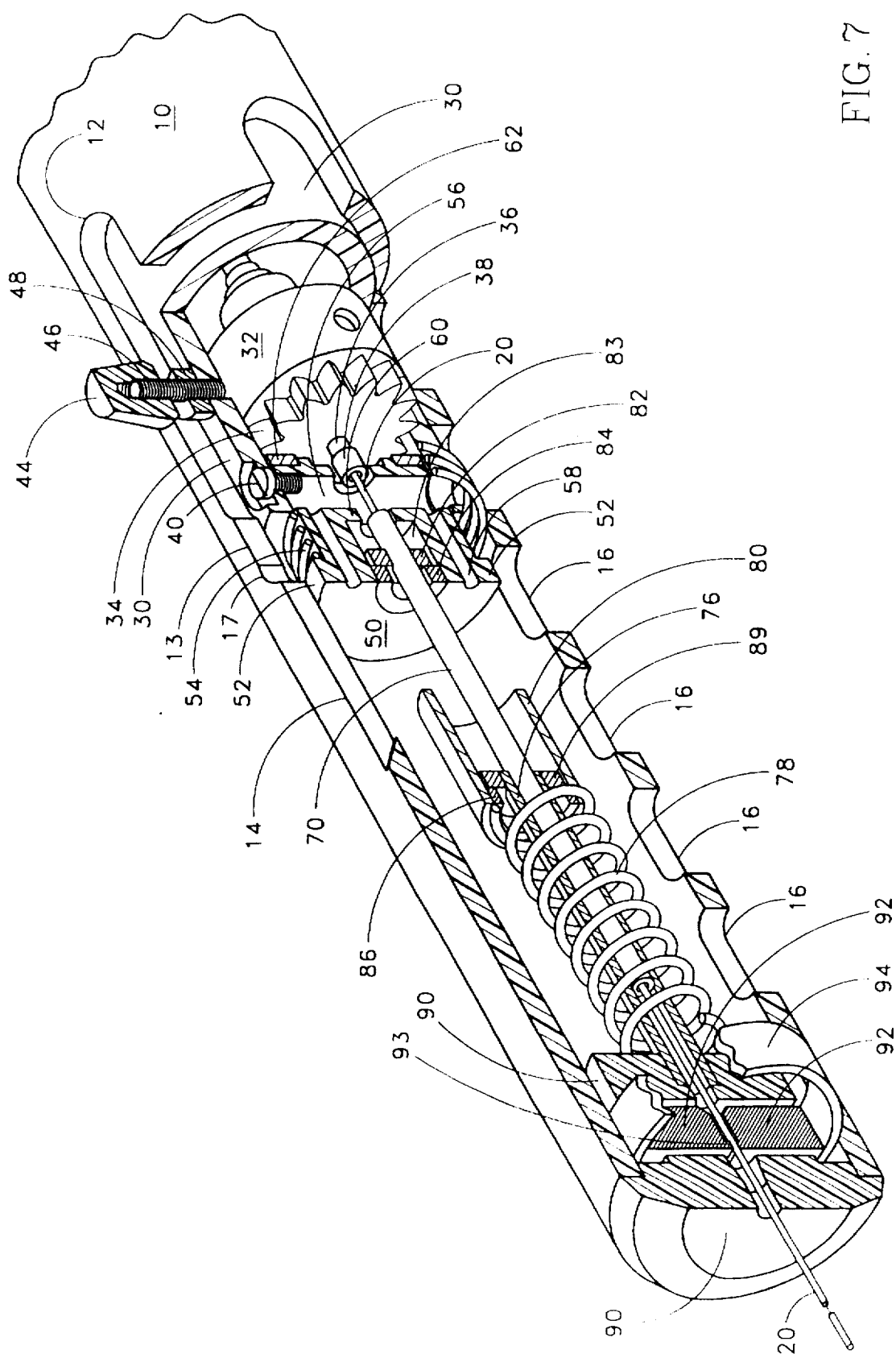
FIG. 7 is a perspective view of the proximal portion of the handle of the atherectomy device of FIG. 6, shown in partial longitudinal cross-section.
Figure 8:
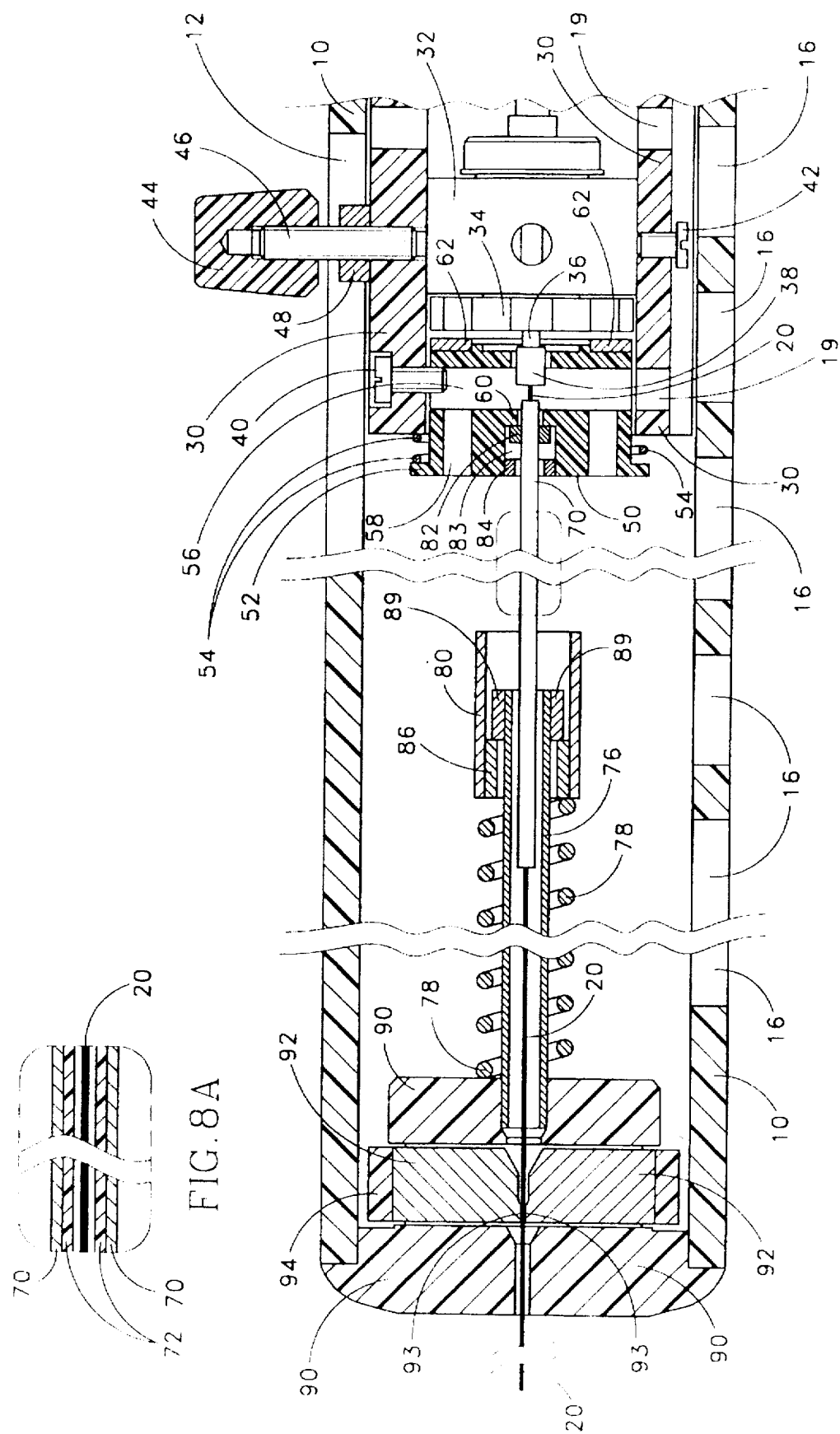
FIG. 8 is a longitudinal cross-sectional view of the proximal portion of the handle of the device of FIG. 6, the turbine carriage being located in a slightly moved position.

FIG. 7 provides a broken-away perspective view of the internal components of one embodiment of the atherectomy device handle of the invention, and FIG. 8 illustrates these components in longitudinal cross-section and with the turbine carriage 30 in a slightly moved position. The turbine carriage 30 has an outer diameter slightly smaller than the inner diameter of the handle housing 10, permitting the carriage 30 to move freely (within a limited range of motion) proximally and distally with respect to the handle housing. A control knob 44 is provided to permit the physician to easily move the turbine carriage 30 back and forth. The control knob 44 is connected by a suitable shaft 46 to the turbine carriage 30, the shaft extending outwardly through an elongated slot 12 in the handle housing 10. A collar 48 may be provided around the shaft 46 to reduce friction and guide the shaft along the walls of the slot 12 in the housing. The collar 48 may be rotatable with respect to the shaft 46 and, for that purpose, it may comprise a bearing. In certain situations when the handle housing 10 is made from a material that is not sufficiently resilient it may be desirable to make the collar 48 from a resilient material. The dimensions of the elongated slot 12 and the collar 48 determine the limits of longitudinal movement of the turbine carriage 30 within the handle housing 10.

The turbine carriage 30 carries a turbine for imparting rotation to the rotatable drive shaft 21. The turbine could be constructed in a variety of suitable ways. In the embodiment depicted in the drawings, the turbine includes a turbine wheel 34 carried on a hollow turbine shaft 36 which passes through a turbine housing 32 containing conventional bearings to support the turbine shaft 36. The hollow turbine shaft 36 in turn is connected to the proximal end of the rotatable drive shaft 21, so that rotation of the turbine wheel 34 by compressed gas imparts rotation to the rotatable drive shaft 21. Since the guide wire may be subject to vibrations when the drive shaft 21 and the turbine shaft 36 are rotated around it, and because the hollow turbine shaft 36 preferably is made from a suitable metal, a plastic bushing 38 may be provided at the proximal end of the turbine shaft 36 to protect the guide wire from abrasion by the proximal end of the rotating hollow shaft 36. A set screw 42 (or equivalent mechanical connection) is provided to secure the turbine housing 32 with respect to the turbine carriage 30.

Figure 17:
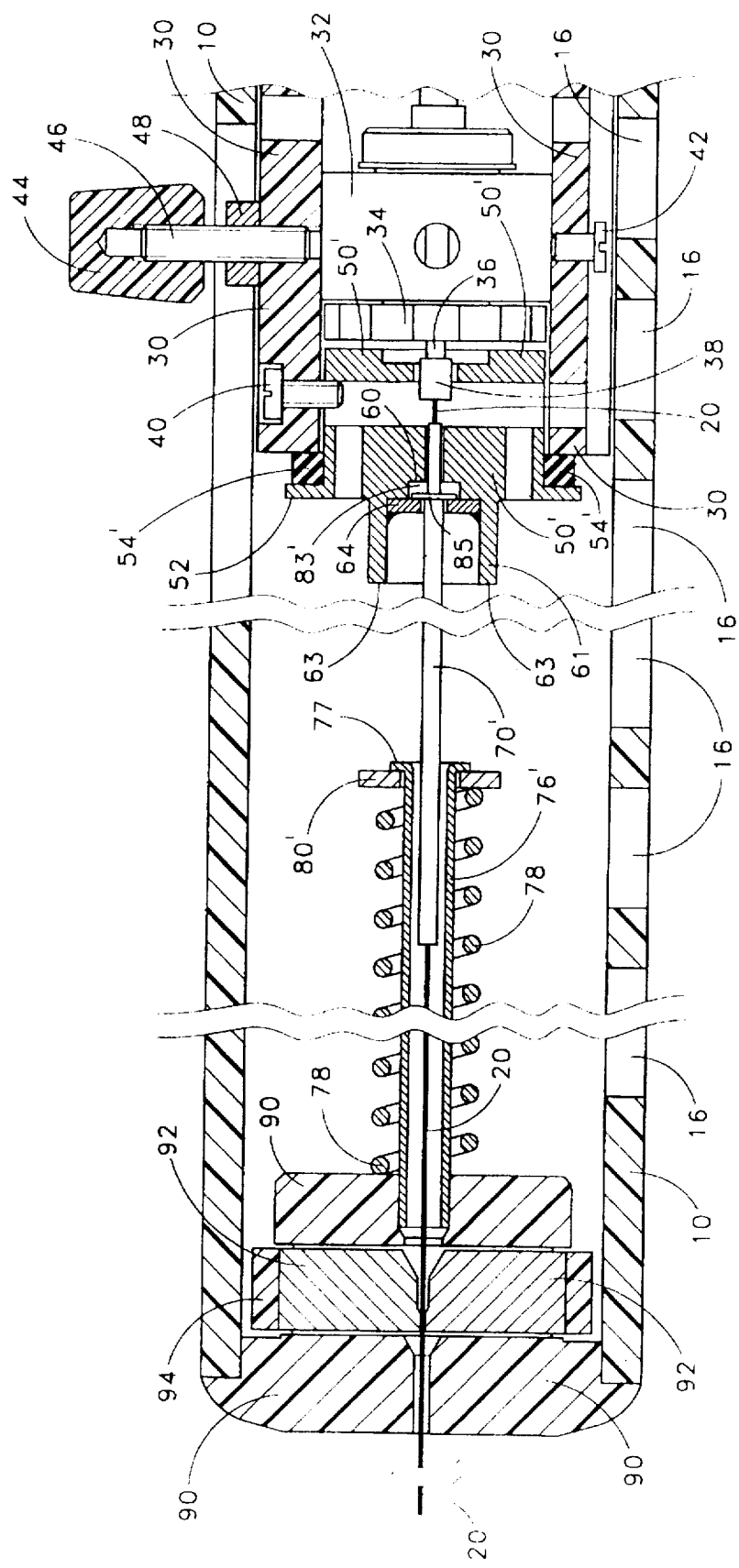
FIG. 17 is a longitudinal cross-sectional view of the proximal portion of a modified embodiment of the atherectomy device of the invention.
Figure 18:
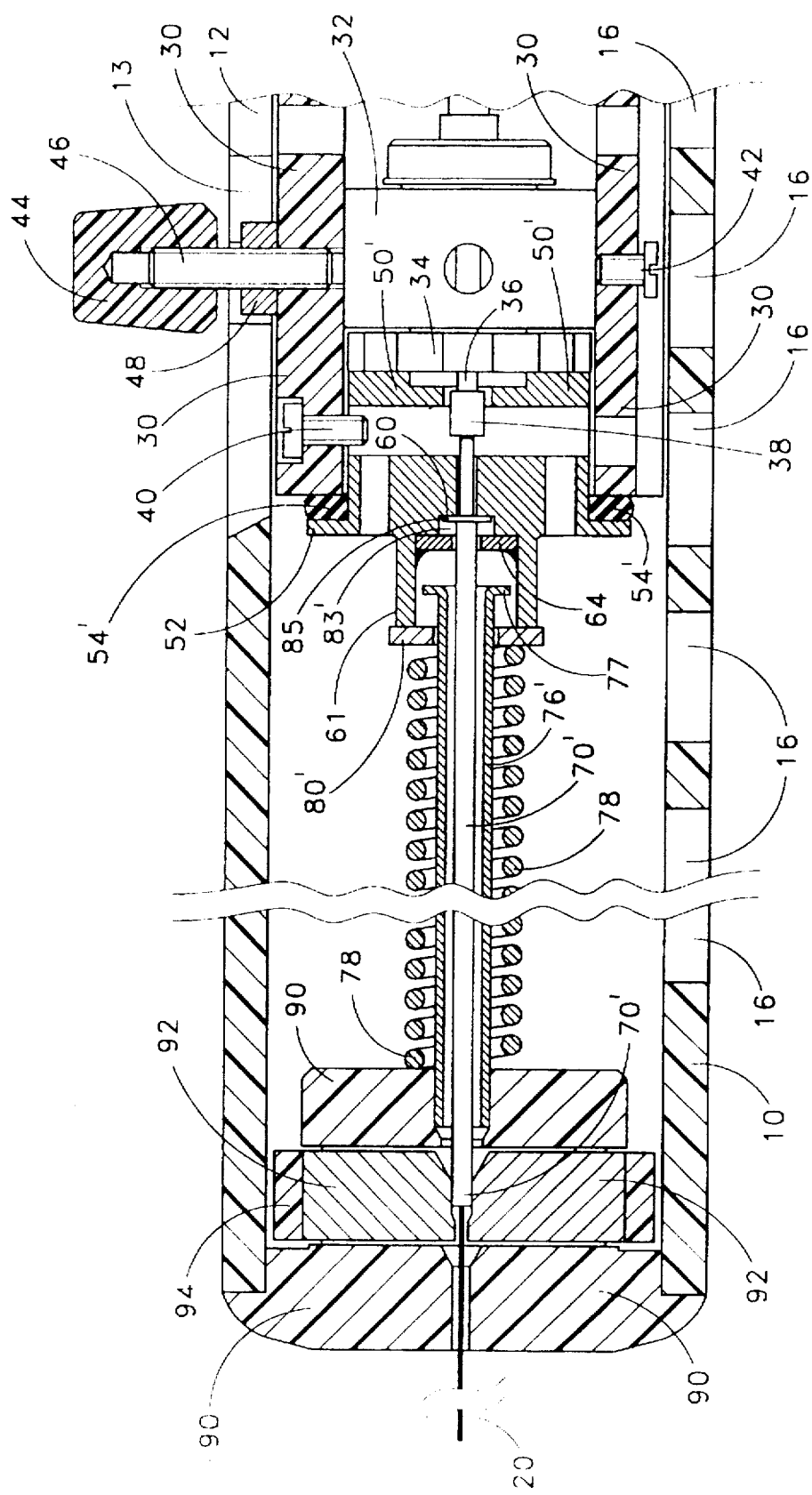
FIG. 18 is a longitudinal cross-sectional view of the atherectomy device of FIG. 17 but showing the device in a moved position.

An important feature of the invention is the provision of a brake which may be actuated to substantially prevent the rotation of the turbine wheel 34 and rotatable drive shaft 21. The brake preferably is constructed so that it will substantially prevent rotation of the turbine wheel 34 even if compressed gas is supplied to the turbine wheel 34. Although such a brake may be provided in a variety of ways, the preferred embodiment shown in the drawings utilizes a brake shoe 50, carried by the turbine carriage 30 just proximal to the turbine wheel 34, and a brake shoe biasing mechanism for biasing the brake shoe 50 away from the turbine wheel 34. As will be described in more detail below, the brake shoe biasing mechanism preferably is a resilient element such as a brake shoe biasing spring 54. In the embodiment shown in FIGS. 7–8 the brake shoe biasing spring 54 is a coil spring disposed between the proximal end of the turbine carriage 30 and a flange 52 extending radially from the brake shoe 50. Other suitable resilient elements may also be employed. For example, the resilient element may comprise a resilient O-ring (as depicted in FIGS. 17–18). A set screw 40 (or other suitable mechanism) is provided to prevent the brake shoe 50 from rotating while permitting it to have a limited range of longitudinal movement with respect to the turbine carriage 30 and the turbine wheel 34. This longitudinal movement is needed to permit the brake shoe biasing spring 54 to move the brake shoe 50 away from the turbine wheel 34. The diameter of the set screw 40 is smaller than the diameter of a preferably round drainage bore 56 into which the set screw extends, the differences in these two diameters determining the extent of longitudinal movement of the brake shoe 50 with respect to the turbine carriage 30 and turbine wheel 34.

A brake shoe engagement mechanism is also provided for overriding the brake shoe biasing mechanism and causing the brake shoe 50 to move from a brake shoe-released position, in which position the turbine wheel 34 is free to rotate, to a brake shoe-engaged position, in which position the brake shoe 50 is operatively engaged with the turbine wheel 34 to prevent rotation of the turbine and the drive shaft 21. (The "brake shoe engagement mechanism" is sometimes referred to as the "brake engagement mechanism," and the "brake shoe-engaged" and "brake shoe-released" positions are sometimes referred to as the "brake-engaged" and "brake-released" positions.) Preferably the brake shoe engagement mechanism is positioned with respect to the brake shoe 50 so that as the turbine carriage 30 is moved proximally (as is described in more detail below) the brake shoe 50 will encounter the brake shoe engagement mechanism. Further proximal movement of the turbine carriage 30 will then urge the brake shoe 50 against the brake shoe engagement mechanism, compressing the brake shoe biasing spring 54 and moving the brake shoe 50 from its brake shoe-released position to its brake shoe-engaged position. In this position the distal surface of the brake shoe 50 operatively engages the proximal surface of the turbine wheel 34, preventing the turbine wheel 34 from rotating. In FIGS. 7–8 the brake shoe engagement mechanism includes an abutment 80 and a brake shoe engagement spring 78. Both the abutment 80 and the brake shoe engagement spring 78 are carried by an outer telescopic tube 76. The brake shoe engagement spring 78 may be a conventional coil compression spring as is shown in FIGS. 7–8.

The embodiment depicted in FIGS. 7–8 includes as a separate component an annular brake pad 62 secured to the distal surface of the brake shoe 50—utilizing a brake pad 62 permits the use of metal or other conventional brake pad materials which may provide the desired brake performance, including the conduction of heat away from the friction interface between the brake pad 62 and the turbine wheel 34. Alternately, the brake shoe may be a single piece, machined or molded.

In the embodiment of FIGS. 7–8 the brake pad 62 directly engages the proximal surface of the turbine wheel 34. The device could also be constructed so that the brake shoe 62 engages the turbine indirectly. For example, a rotating component separate from the turbine wheel 34 could be positioned to be engaged by the brake shoe 62. Such a rotating component could be carried by the turbine wheel 34, the hollow turbine shaft 36 or even by the drive shaft 21. Other means of operatively engaging the brake shoe 50 to prevent rotation of the drive shaft 21 and turbine could also be employed by one of ordinary skill in the art.

Much of the fluid introduced by the fluid supply line 23 (discussed above with respect to FIG. 6) travels distally through the catheter 22 to the distal end of the catheter 22, but some of the fluid travels proximally along the drive shaft 21 and through the hollow turbine shaft 36. It is desirable to provide a path for this fluid to drain freely out of the handle housing 10 so that accumulation of fluid within the handle housing 10 does not interfere with the proper functioning of the atherectomy device handle. Any of a variety of paths may be provided for draining this fluid from the handle housing 10. FIGS. 7–8 illustrate one such configuration. The proximal end of the hollow turbine shaft 36, with its plastic bushing 38, terminates within a generally vertically oriented drainage bore 56 in the brake shoe 50. A pair of longitudinal drainage vents 58 is provided through the proximal portion of the brake shoe 50, the vents 58 providing ambient pressure to the brake shoe drainage bore 56. A plurality of drainage holes 19 are formed in the turbine carriage 30, one of them being in alignment with the drainage bore 56 in the brake shoe 50. A plurality of drainage slots 16 also are provided in the handle housing 10. Thus, fluid escaping the proximal end of the turbine's hollow shaft 36 enters the drainage bore 56 in the brake shoe 50 and drains out through the drainage hole 19 in the turbine carriage 30 and the drainage slots 16 in the handle housing 10, the drainage vents 58 facilitating the free flow of such fluid.

The braking function described above desirably is related to the clamping of the guide wire 20. FIGS. 7–8 depict a type of guide wire clamp that may be used to releasably engage the proximal portion of the guide wire 20 (i.e., that portion of the guide wire 20 that extends proximally from the drive shaft and is seen in the drawings as extending proximally from the turbine) once the distal end of the guide wire 20 has been properly placed across the stenosis and the atherectomy device has been advanced over the guide wire 20. Clamping of the guide wire is desirable to prevent rotation of the guide wire 20 when the turbine and the drive shaft 21 are rotated, and to prevent inadvertent longitudinal movement of the guide wire 20 as the turbine carriage 30 and drive shaft 21 are advanced and retracted.

The basic operation of the guide wire clamp of FIGS. 7–8 is as follows (some specific features of the clamp will be described in more detail below). The clamp is movable from a guide wire-clamped position to a guide wire-released position, and includes a clamp control mechanism (described below) for controlling the position of the clamp. A pair of opposed clamping blocks 92 is provided, each having a clamping surface 93, and a clamp biasing mechanism for biasing at least one of the clamping surfaces 93 toward the other to clamp the guide wire 20. Preferably the clamp biasing mechanism comprises one or more springs for biasing the clamping blocks 92 and their clamping surfaces 93 toward each other to clamp the guide wire 20.

Although any of a variety of springs could be utilized (and some alternate configurations for such springs are described below), in the preferred embodiment, shown in the FIGS. 7–8, a single spring is provided in the form of a resilient circumferential collar 94. In this embodiment, the collar 94 is manufactured to have a substantially round shape. When squeezed into an oval shape and mounted around the clamping blocks 92 (as is illustrated in FIGS. 26A–26D, described in greater detail below), the collar 94 attempts to return to its round shape. The size of the clamping blocks 92 preferably is selected so that the combined height of the clamping blocks 92 is slightly greater than the inner diameter of the round collar 94 so that the collar 94, after being placed around the clamping blocks, maintains a slightly oval shape, thus urging the clamping blocks 92 toward each other. Whenever the guide wire 20 is placed between the clamping surfaces 93 of the clamping blocks 92, the clamping blocks 92 are moved radially outwardly slightly, causing the collar 94 to become even more oval in shape, thereby further increasing the pressure on the clamping blocks 92. The oval resilient collar 94 thus exerts pressure on the clamping blocks 92, pinching the guide wire 20 between the clamping surfaces 93 of the clamping blocks 92.

The control knob 44, the turbine carriage 30 and the associated components have three sets of longitudinal positions (or ranges of positions) with respect to the handle housing 10. The significance of these positions (or ranges of positions) is described below:

(1) throughout most of the range of positions of the control knob 44 (see FIGS. 6–11) the clamp is in its guide wire-clamped position, securing the guide wire 20, and the brake is in its brake-released position, permitting the turbine and drive shaft 21 to rotate (this range of positions sometimes will be referred to as the "range of turbine carriage-unlocked positions" or "range of prime mover-unlocked positions", because throughout this range of positions the turbine carriage/ prime mover is generally permitted to move freely longitudinally (within a limited range of motion) along the slot 12 in the housing 10);

(2) when the control knob 44 is in the most proximal portion 17 of the slot 12 (see FIGS. 14–16), the clamp is in its guide wire-released position, permitting movement of the guide wire 20, and the brake is in its brake-engaged position, preventing rotation of the turbine and drive shaft 21 (this position sometimes will be referred to as the "turbine carriage-locked position" or "prime mover-locked position" because in the preferred embodiment illustrated in the drawings the turbine carriage/prime mover in this longitudinal position is releasably locked against free movement along the slot 12 in the housing 10); and (3) when the control knob 44 is moved into the narrowed portion 13 of the slot 12, (i.e., when the turbine carriage is moved from the range of turbine carriage-unlocked positions toward the turbine carriage-locked position (see FIGS. 12–13)), the brake becomes engaged, preventing rotation of the turbine and drive shaft 21, while the clamp is not yet released, so movement of the guide wire 20 is not yet possible (this range of positions will be referred to as the range of "transitional positions").

When the control knob 44 is moved from the turbine carriage-unlocked position to the turbine carriage-locked position the brake becomes engaged before the clamp is released. This sequence of operation of the brake and the clamp when the control knob 44 is moved from the turbine carriage-unlocked position to the turbine carriage-locked position assures operational safety of the atherectomy device.

In FIGS. 7–8 the control knob is located within the range of turbine carriage-unlocked positions, with the clamping blocks 92 engaging the guide wire 20 and the brake shoe 50 spaced away from the turbine wheel 34. In the position shown in FIGS. 7–8 compressed gas may be supplied to the turbine wheel 34, causing it, along with the drive shaft 21, to rotate, and permitting the physician to remove stenotic tissue from the lesion being treated. When treating such a stenosis the physician will move the control knob 44 (along with the turbine carriage 30, the turbine and the rotating drive shaft 21) forward and backward, causing the tissue removal section 26 of the drive shaft 21 to advance and retract with respect to the stenosis. The physician typically uses short forward and backward movements of the control knob 44 to remove small portions of the stenotic tissue with each stroke. Typically many such strokes are required to completely cross a stenotic lesion, and often more than one lesion must be treated along a length of an artery. Thus, desirably the tissue removal section 26 is capable of being moved longitudinally through a range of positions to permit treatment of more than one lesion without having to reposition the catheter 22 within the artery.

Figure 9:
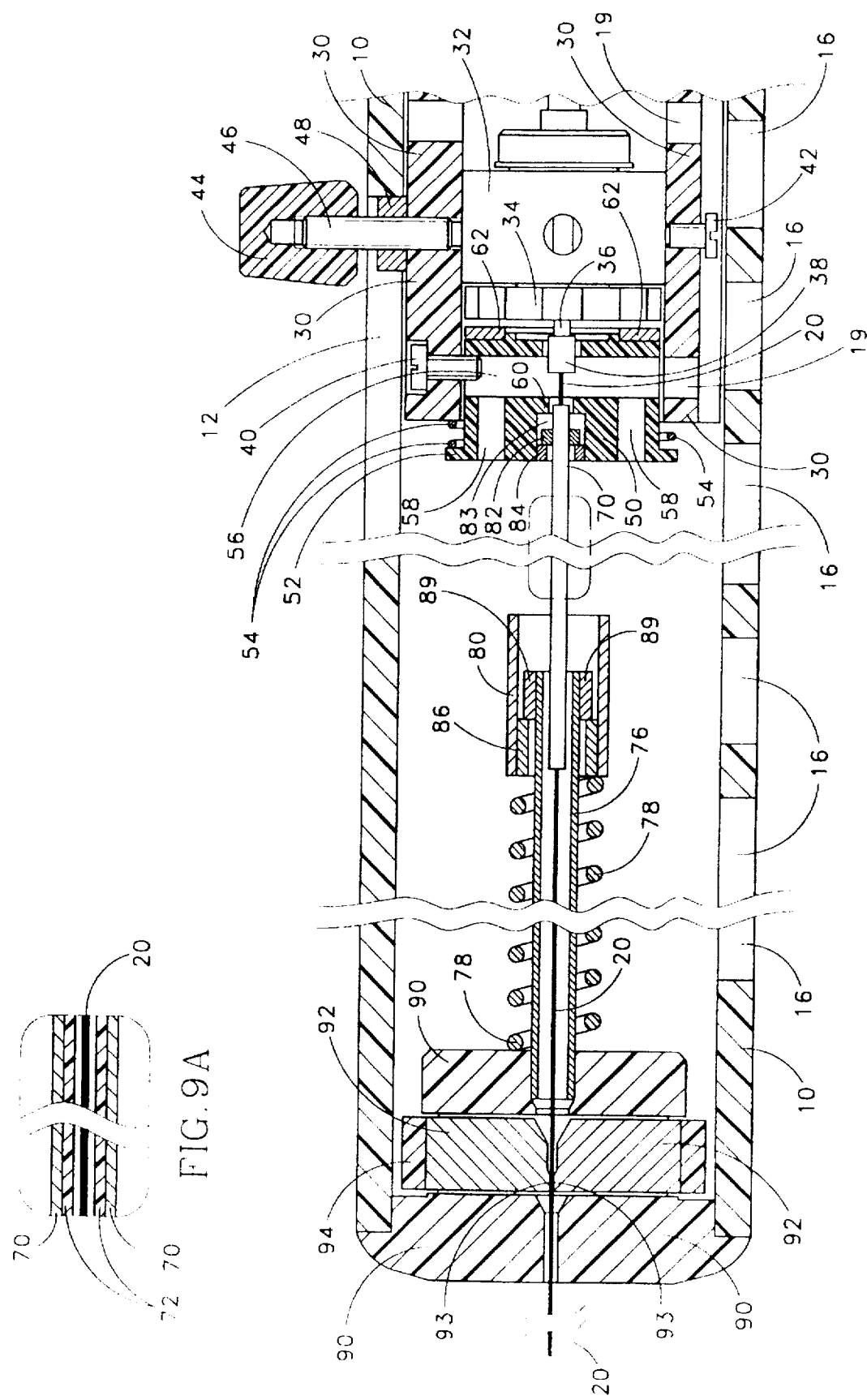
FIG. 9 is a longitudinal cross-sectional view similar to FIG. 8 but showing the atherectomy device in a moved position, the turbine carriage being located in its most distal position.
Figure 10:
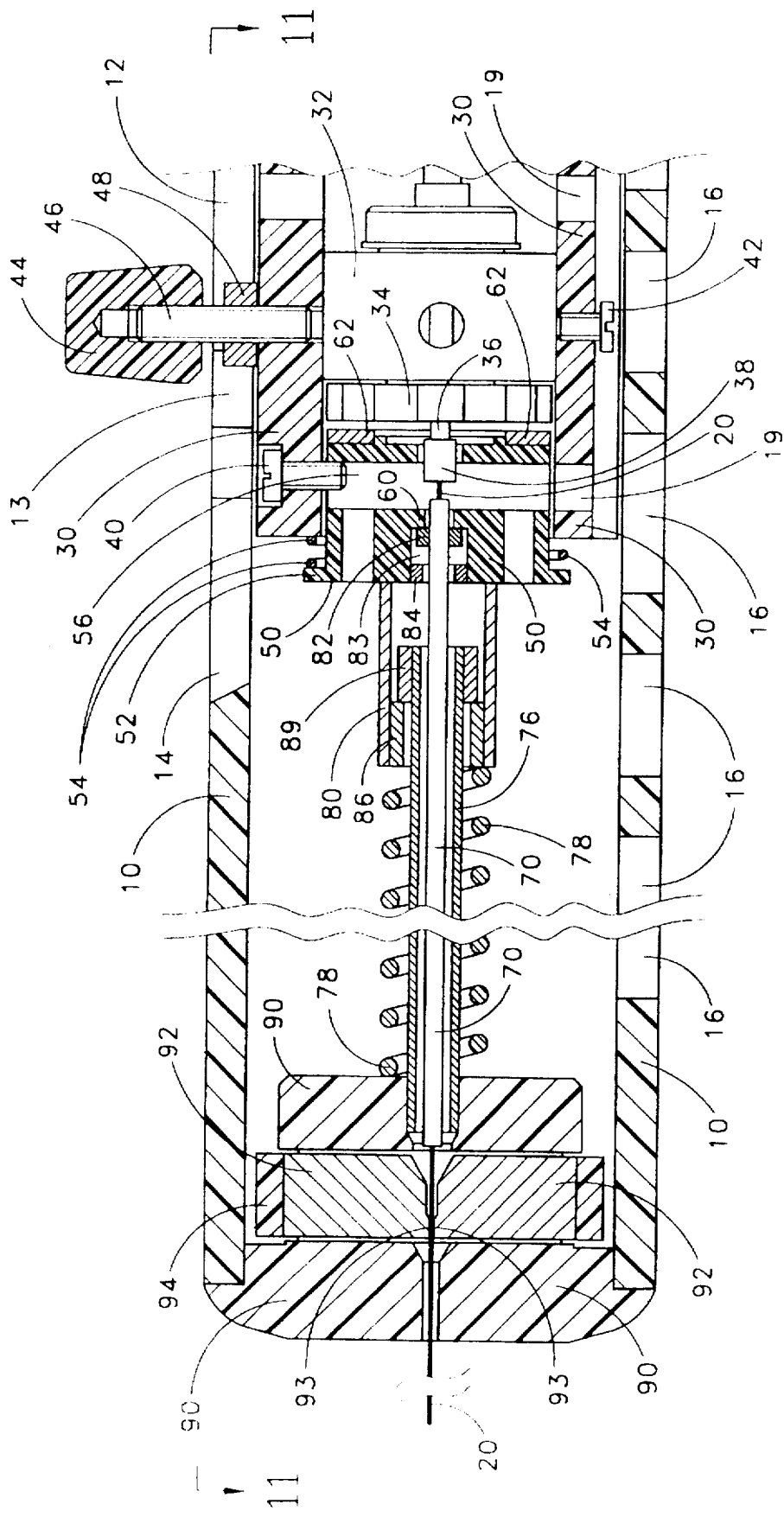
FIG. 10 is a longitudinal cross-sectional view similar to FIG. 8, showing the atherectomy device in another moved position, the turbine carriage being located at the most proximal end of a range of turbine carriage-unlocked positions.
Figure 11:
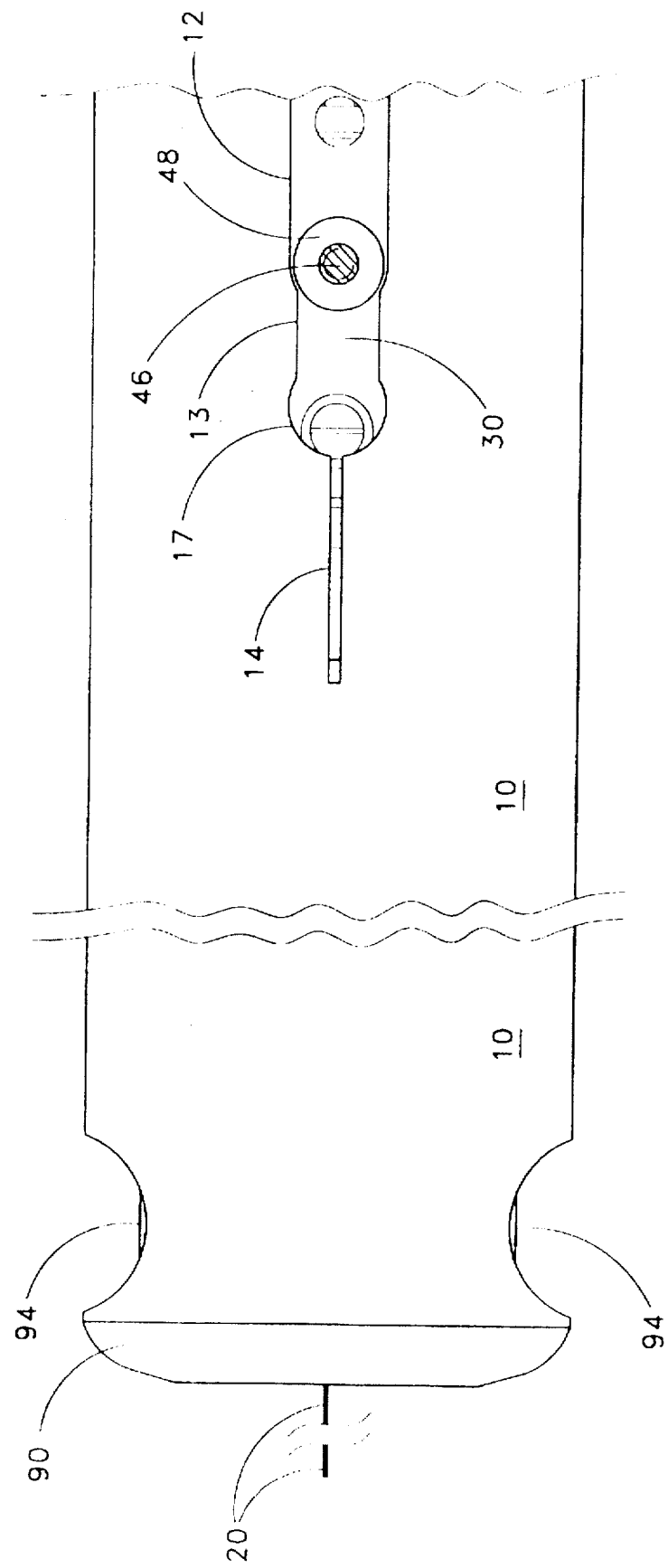
FIG. 11 is a top view (partial cross-section haven been taken along lines 11—11 of FIG. 10) showing the proximal portion of the atherectomy device in the position illustrated in FIG. 10.

The total range of longitudinal movement of the drive shaft 21 (and its tissue removal section 26) with respect to the catheter 22 is determined by the length and configuration of the slot 12 in the handle housing 10. The limit on forward (distal) movement of the drive shaft 21 with respect to the catheter 22 (i.e., the distal end of the range of turbine carriage-unlocked positions) is reached when the control knob 44 is moved distally and the collar 48 encounters the distal end of the slot 12. This position of the device is illustrated in FIG. 9. The proximal end of the range of turbine carriage-unlocked positions of the drive shaft 21 with respect to the catheter 22 is reached when the control knob 44 is moved proximally and the collar 48 encounters a narrowed portion 13 of the slot 12 in the handle housing 10. This position of the device is illustrated in FIGS. 10–11. Throughout the range of turbine carriage-unlocked positions the brake is in its brake-released position, permitting the turbine and drive shaft 21 to rotate, and the clamp is in its guide wire-clamped position, preventing the guide wire 20 from moving.

Figure 12:
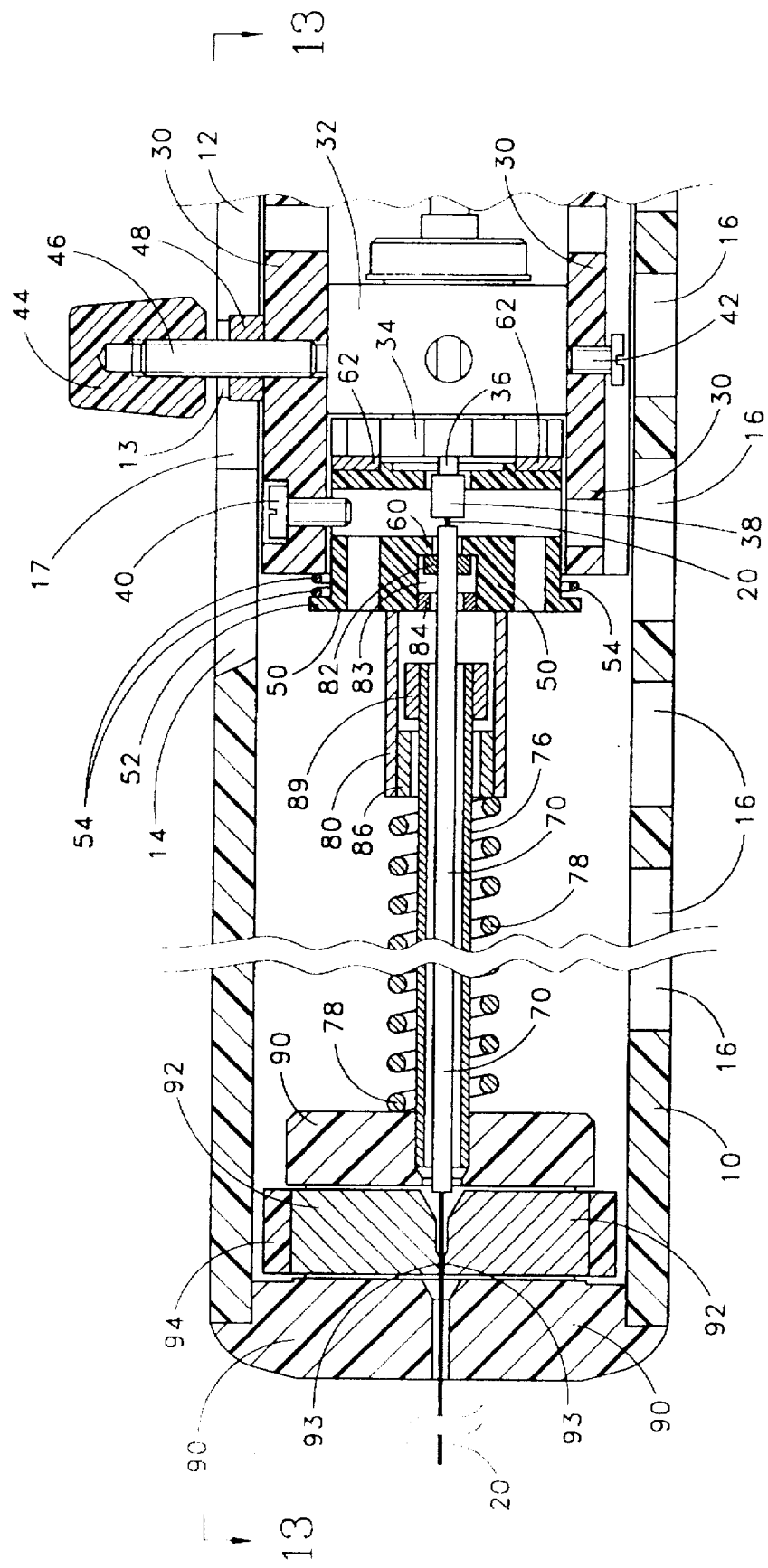
FIG. 12 is a longitudinal cross-sectional view similar to FIG. 8, showing the atherectomy device in another moved position, the turbine carriage being located in the range of transitional positions.
Figure 13:
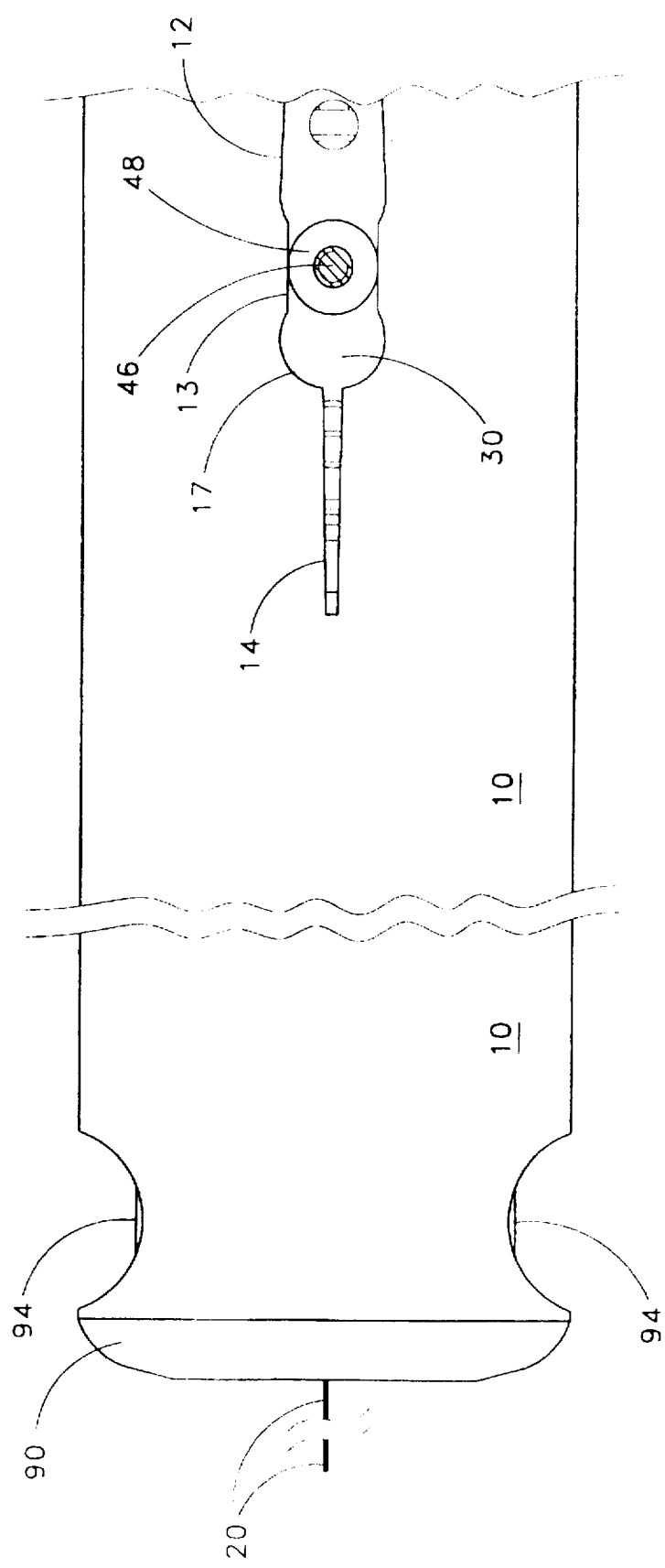
FIG. 13 is a top view (partial cross-section haven been taken along lines 13—13 of FIG. 12) showing the proximal portion of the atherectomy device in the position illustrated in FIG. 12.

In order to advance the drive shaft 21 and the handle of the atherectomy device over the guide wire 20 or to remove the guide wire from the atherectomy device the control knob 44 is moved from the range of turbine carriage-unlocked positions through the range of transitional positions into the turbine carriage-locked position. Referring to FIGS. 12–13, the control knob 44 in these drawings has already been moved from the range of turbine carriage-unlocked positions into the range of transitional positions. This is accomplished by applying a little extra rearward force on the control knob 44 to urge the collar 48 in between the walls of the narrowed portion 13 of the slot 12. A relief slot 14 is provided proximally of the main elongated slot 12, permitting the opposing walls of the narrowed portion 13 of the slot 12 to move slightly away from each other, thus slightly expanding the diameter and circumference of this portion of the handle housing 10 to permit the collar 48 to pass through the narrowed portion 13 of the slot 12. Desirably the handle housing is made from a somewhat resilient material (preferably a suitable plastic such as ABS) to permit it to radially expand slightly and act as a type of spring, regaining its original diameter and circumference when the control knob 44 is moved out of the range of transitional positions.

Figure 19:
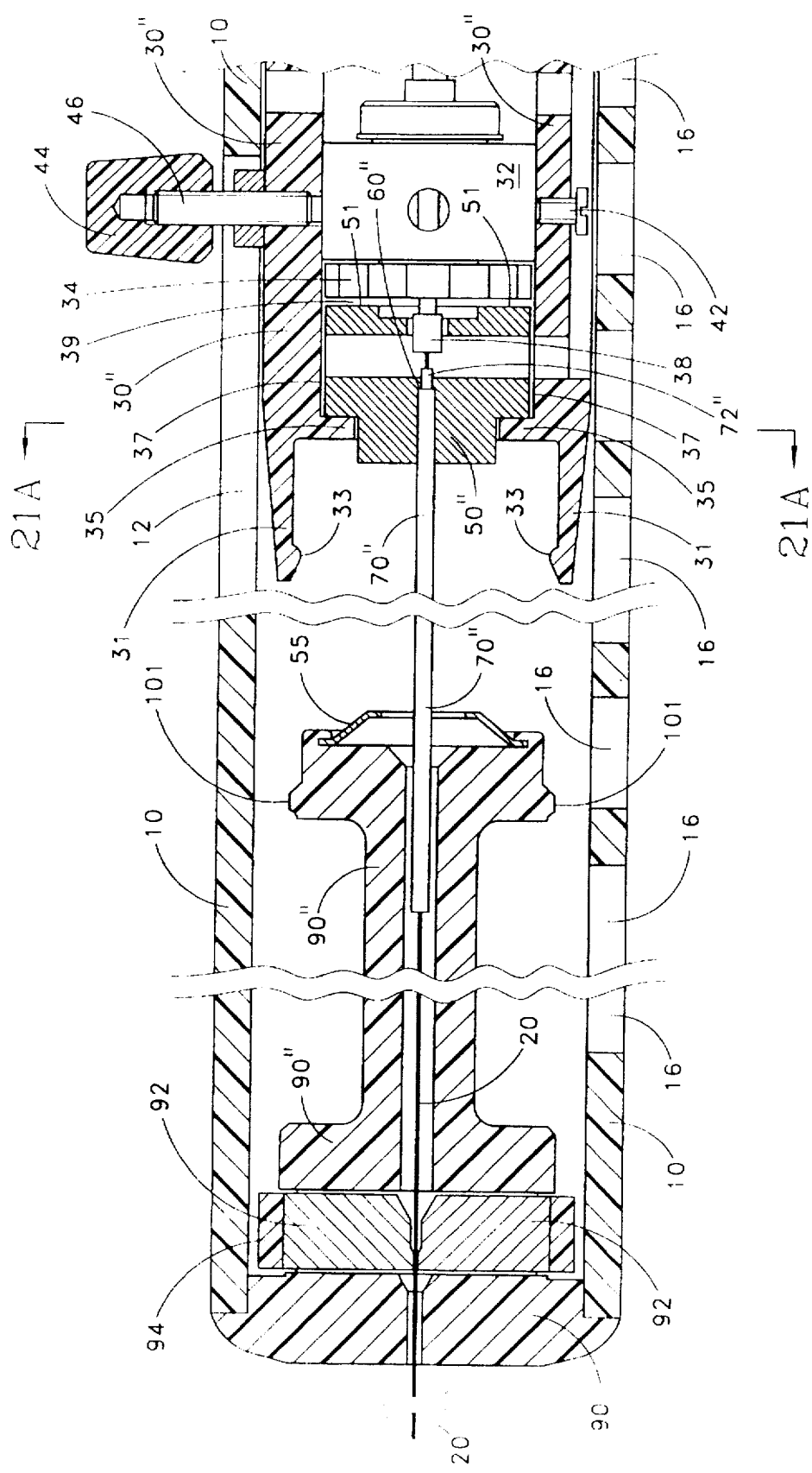
FIG. 19 is a longitudinal cross-sectional view of the proximal portion of another modified embodiment of the atherectomy device of the invention.
Figure 20:
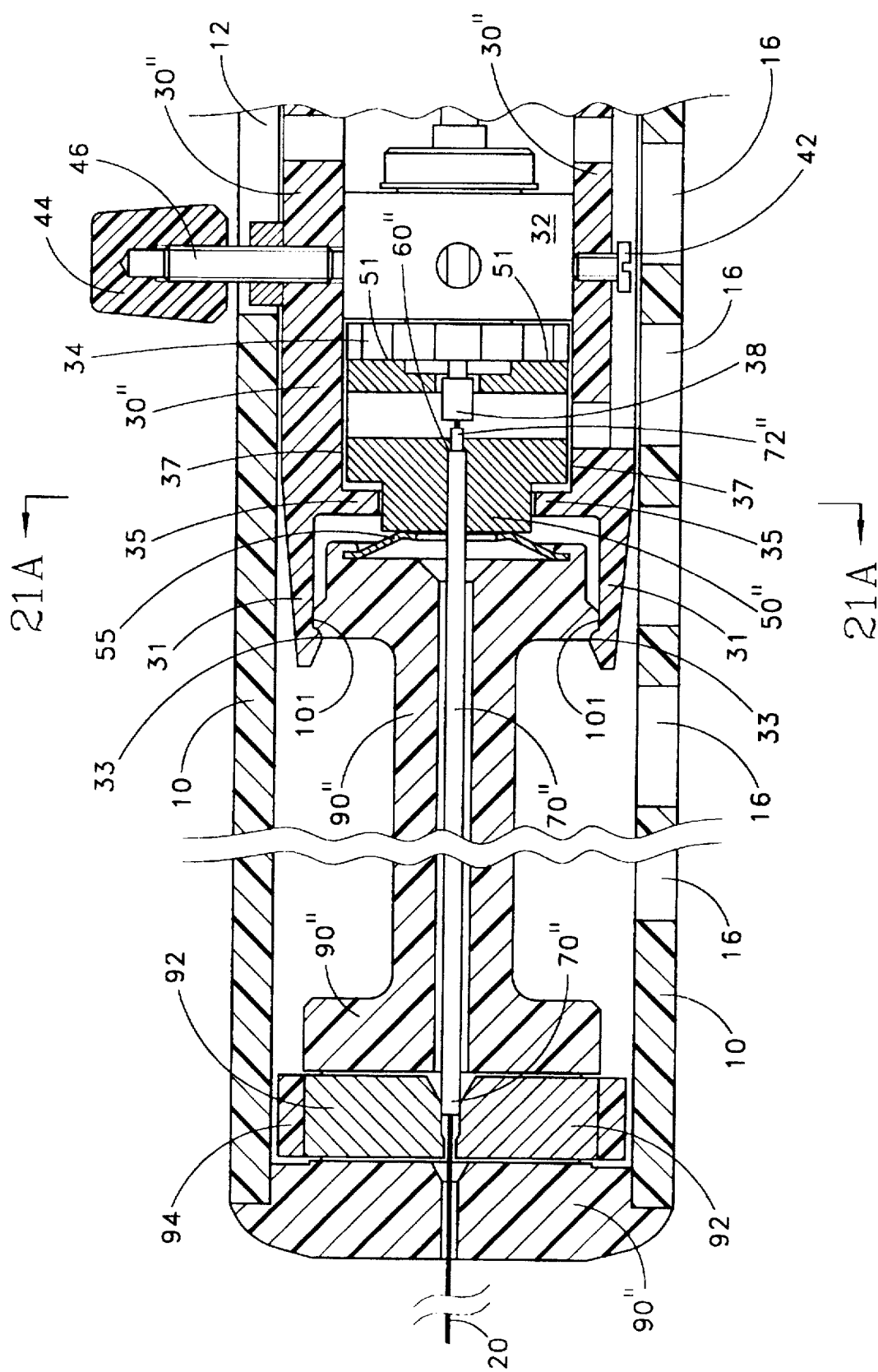
FIG. 20 is a longitudinal cross-sectional view of the atherectomy device of FIG. 19 but showing the device in a moved position.

The preferred embodiment illustrated in the drawings utilizes the resilient nature of the handle housing 10 and a narrowed portion 13 of the slot 12 as a type of detent to prevent the control knob 44 from entering the range of transitional positions without the exertion of a little extra force, thereby preventing inadvertent movement of the control knob 44 from the range of turbine carriage-locked positions into the turbine carriage-unlocked position, and vice versa. Other types of mechanical restrictions in the slot 12 may also be provided to serve this function, such as a spring biased detent mechanism, or equivalent structures. Thus, this disengagable mechanical linkage functions as a turbine carriage lock for automatically restraining the turbine carriage 30 from longitudinal movement with respect to the handle when the turbine carriage 30 is moved longitudinally to the turbine carriage-locked position. (The "turbine carriage lock" is sometimes referred to as the "prime mover lock" for automatically restraining the prime mover from longitudinal movement with respect to the handle when the prime mover is moved longitudinally to the prime mover-locked position.) Other types of disengagable mechanical linkages between the turbine carriage and the handle may also be utilized to function as a turbine carriage lock for releasably locking the turbine carriage in the turbine carriage-locked position. Many types of such linkages will include a pair of interlocking members that are releasably engageable with each other, one of the members being carried by the turbine carriage 30 and the other being carried by the handle. Such interlocking members may be comprised of a detent and complementary member engageable with the detent, such as the narrowed portion 13 (detent) of the slot 12 and the collar 48 (complementary member) discussed above. Another example of such a linkage is shown in FIGS. 19–20 described below.

Referring to FIG. 12, when the control knob 44 is being moved through the range of transitional positions the brake pad 62 carried by the brake shoe 50 engages the proximal surface of the turbine wheel 34 to prevent the rotation of the turbine wheel 34 and the attached drive shaft 21. Notice that this braking of the turbine wheel 34 already has occurred in FIG. 12, while the clamping blocks 92 are still firmly gripping the guide wire 20.

Figure 14:
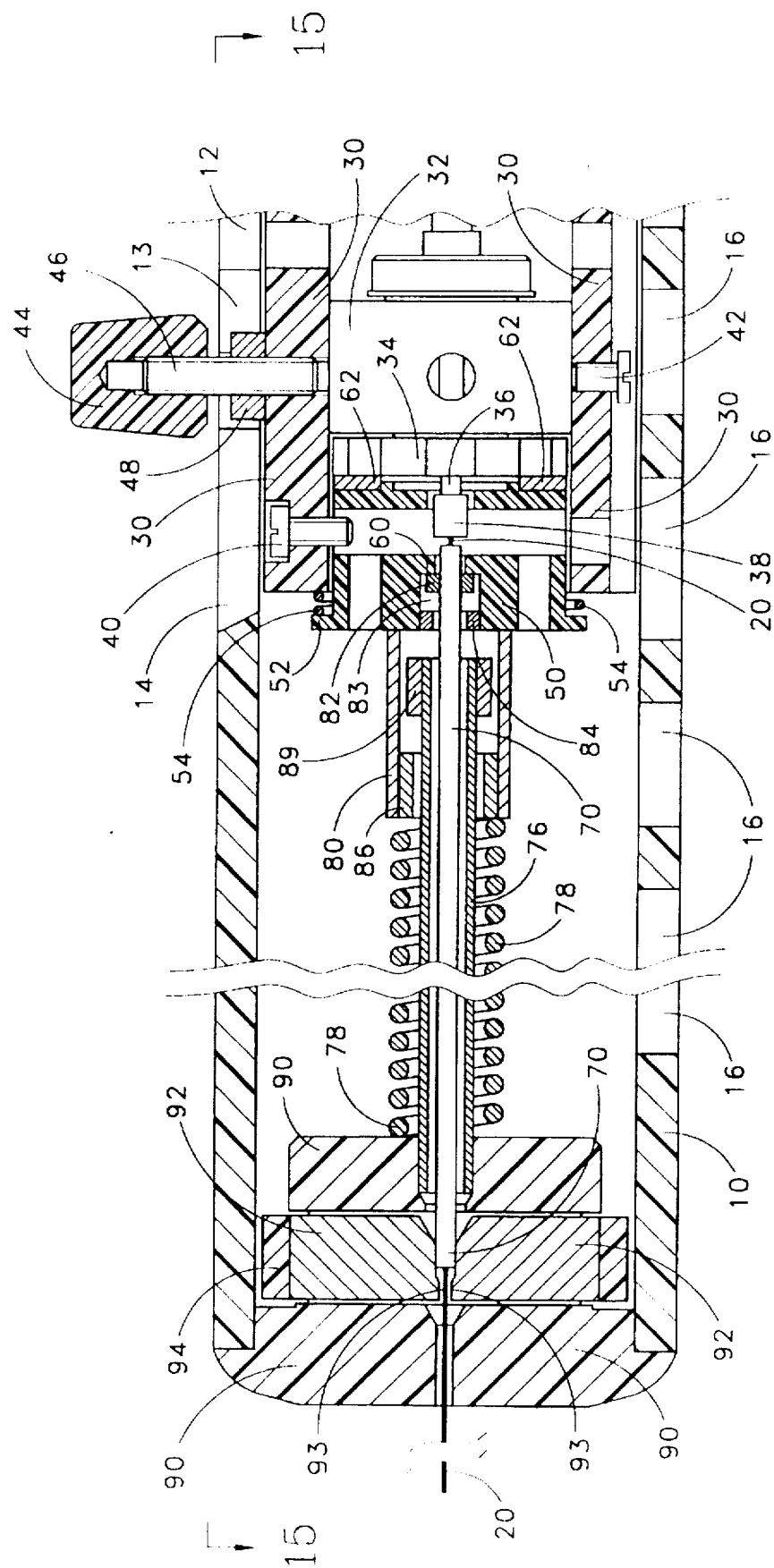
FIG. 14 is a longitudinal cross-sectional view similar to FIG. 8, showing the atherectomy device in another moved position, the turbine carriage being located in its turbine carriage-locked position.
Figure 15:
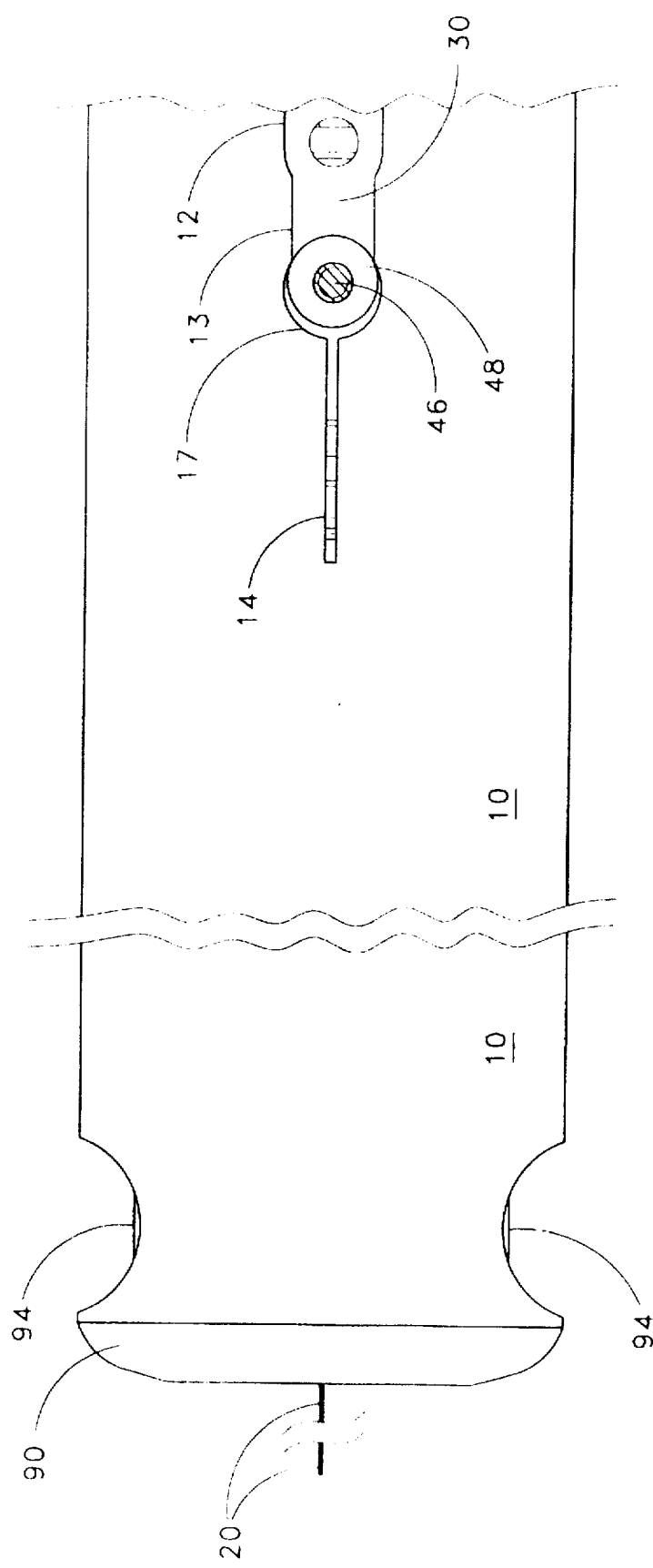
FIG. 15 is a top view (partial cross-section haven been taken along lines 15—15 of FIG. 14) showing the proximal portion of the atherectomy device in the position illustrated in FIG. 14.
Figure 16:
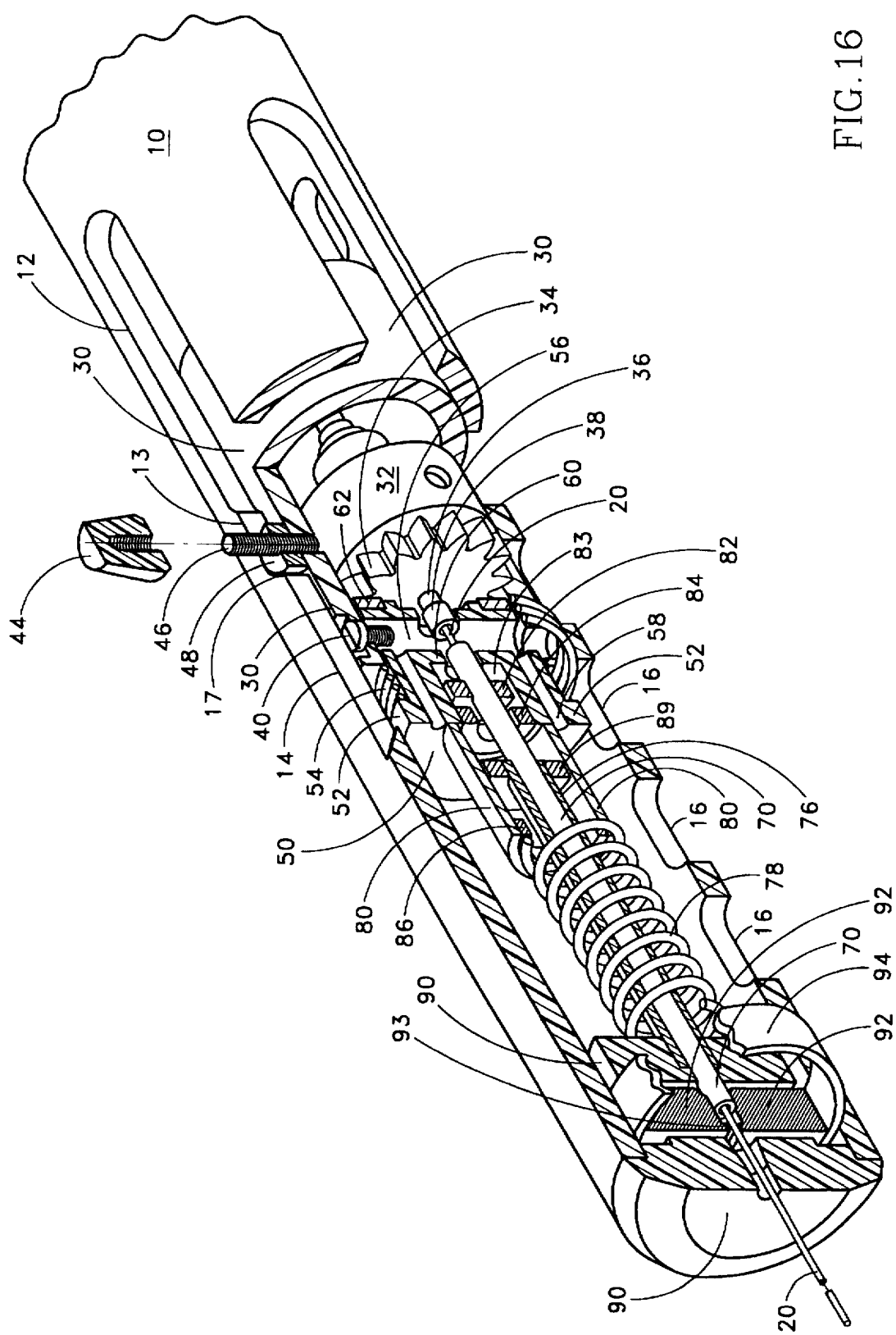
FIG. 16 is a partial longitudinal cross-section of a perspective view of the proximal portion of the handle of the atherectomy device in the position illustrated in FIGS. 14-15.

Further proximal movement of the control knob 44 will move the control knob 44 out of the range of transitional positions and into the turbine carriage-locked position shown in FIGS. 14–16. In the turbine carriage-locked position, the clamping blocks 92 are spaced from each other to release the guide wire 20, and the turbine wheel 34 continues to be firmly engaged by the brake shoe 50 to prevent rotation of the turbine and drive shaft 21. The collar 48 no longer engages the walls of the narrowed portion 13 of the slot 12 in the handle housing 10, but rather is located in the most proximal portion 17 of the slot 12. The control knob 44 and the turbine are thus "locked" in the turbine carriage-locked position by the narrowed portion 13 of the slot 12. The control knob 44 and the turbine may be moved out of this turbine carriage-locked position by applying a little extra forward force to the control knob 44 to urge the collar 48 in between the walls of the narrowed portion 13 of the slot 12, through the range of transitional positions and into the range of turbine carriage-unlocked positions, where the control knob 44 and the turbine are free to be moved along the range of turbine carriage-unlocked positions.

The mechanism for causing the braking and unclamping sequence that occurs as the control knob 44 is moved from the range of turbine carriage-unlocked positions through the range of transitional positions to the turbine carriage-locked position is as follows. Referring again to FIGS. 7–9 (which show the control knob 44 in the range of turbine carriage-unlocked positions), the brake shoe engagement mechanism is located proximally of the brake shoe 50. As described above, the brake shoe engagement mechanism includes an abutment 80 and a brake shoe engagement spring 78. Both the abutment 80 and the brake shoe engagement spring 78 are carried by an outer telescopic tube 76. The outer telescopic tube 76 is carried by a housing 90 of the guide wire clamp with the proximal end of the outer telescopic tube 76 extending into the central opening of the clamp housing 90. Thus, the brake shoe engagement spring 78 is compressed between the abutment 80 and the clamp housing 90. The brake shoe engagement spring 78 may be a conventional coil spring as is shown in FIGS. 7–9 (the diameter and pitch of the brake shoe engagement spring 78 are somewhat exaggerated in the drawings for the sake of clarity—preferably the inner diameter of the brake shoe engagement spring 78 is just slightly larger than the outer diameter of the outer telescopic tube 76). The abutment 80 in this embodiment is comprised of a tube with an inner diameter that is larger than the outer diameter of the outer telescopic tube 76. The abutment tube 80 is interlocked with the outer telescopic tube 76 by an inner collar 86 and an outer collar 89. The inner collar 86 is secured to the inner surface of the abutment tube 80, and the outer collar 89 is secured to the distal end of the outer telescopic tube 76. This interlocking configuration, formed by the inner collar 86 and the outer collar 89, prevents the brake shoe engagement spring 78 from pushing the proximal end of the abutment tube 80 distally beyond the distal end of the outer telescopic tube 76.

When the control knob 44 is located in the range of turbine carriage-unlocked positions, as it is in FIGS. 7–9, the distal end of the abutment 80 is spaced from the proximal surface of the brake shoe 50, and the brake shoe biasing spring 54 prevents the brake shoe 50 from contacting the turbine wheel 34. When the control knob 44 is moved to the proximal end of the range of turbine carriage-unlocked positions, (see FIGS. 10–11), the proximal surface of the brake shoe 50 contacts the distal end of the abutment 80, but the brake shoe 50 has not yet operatively engaged the turbine wheel 34. As the control knob 44 is moved further proximally into the range of transitional positions, (see FIGS. 12–13), the distal end of the abutment 80 begins to press against the proximal surface of the brake shoe 50. The brake shoe engagement spring 78 is designed and selected to be sufficiently strong that it overpowers the brake shoe biasing spring 54, urging the brake shoe 50 against the turbine wheel 34. Engagement of the brake shoe 50 (through its brake pad 62) with the turbine wheel 34 prevents rotation of the turbine wheel 34 (see FIG. 12).

As the control knob 44 is moved through the range of transitional positions and the braking of the turbine wheel 34 is occurring, another movement is also in progress to release the clamp. FIGS. 7–9, which show the control knob 44 in the range of turbine carriage-unlocked positions, also depict the clamp control mechanism which provides control of the position of the clamp, the clamp being movable from a guide wire-clamped position to a guide wire-released position. Preferably the clamp control mechanism comprises a clamp control rod having a proximal end portion and a distal end portion, the distal end portion of the clamp control rod being operatively connected to the brake shoe 50. In FIGS. 7–9 the clamp control rod is actually a tube (clamp control tube 70), having a central lumen through which the guide wire 20 may pass. Preferably the clamp control tube includes a polytetrafluoroethylene lining 72, as is shown in FIGS. 8A and 9A.

The clamp control tube 70 is slidably received within a central lumen of the outer telescopic tube 76. The clamp control tube 76 is longer than the outer telescopic tube 76, and is longitudinally movable with respect to the guide wire clamp from a range of clamp-released positions (sometimes referred to as a "range of disengaged positions") to a clamp-engaged position (sometimes referred to as an "engaged position"), in which position the proximal end portion of the clamp control tube 70 extends proximally beyond the proximal end of the outer telescopic tube 76 and becomes wedged between the clamping blocks 92, thereby releasing the guide wire 20 from the clamp.

The clamp control tube 70 includes a radially outwardly extending flange 82 (here shown as a separate component secured to a distal end portion of the clamp control tube 70), the brake shoe including a central cavity 83 capturing the radially outwardly extending flange 82. This central cavity 83 of the brake shoe 50 desirably is longitudinally longer (preferably at least about 1 mm longer) than the flange 82 of the clamp control tube 70, permitting limited longitudinal movement of the clamp control tube 70 with respect to the brake shoe 50.

The longitudinal movement of the flange 82 is restricted distally by shoulder 60 of the brake shoe 50 and proximally by a complementary flange 84 secured to the brake shoe 50. Thus, the clamp control tube 70 generally moves forward and backward together with the brake shoe 50 as the brake shoe 50 is moved forward and backward together with the turbine carriage 30 in response to the forward and backward movements of the control knob 44. When the control knob 44 is located in the range of turbine carriage-unlocked positions, as shown in FIGS. 7–9, the proximal end of the clamp control tube 70 is spaced quite a distance from the clamping blocks 92. FIGS. 10–11 show the control knob at the proximal end of the range of turbine carriage-unlocked positions. In FIG. 10 the flange 82 has been pushed proximally by the shoulder 60 of the brake shoe 50, causing the proximal end of the clamp control tube 70 to closely approach the clamping blocks 92. Although in FIG. 10 the distance between the proximal end of the clamp control tube 70 and the clamping blocks 92 is fairly small, the clamp control tube 70 has not yet engaged the clamping blocks 92. In FIGS. 12–13, the control knob has been moved proximally into the range of transitional positions. Notice that in FIG. 12 the abutment 80 is pressing against the proximal surface of the brake shoe 50, urging the brake shoe 50 (and its brake pad 62) against the turbine wheel 34 to prevent it from rotating. Thus, the brake shoe 50 has moved to its brake shoe-engaged position, while the clamp control tube 70 has still not contacted the clamping blocks 92 to unclamp the guide wire 20, though the distance between the proximal end of the clamp control tube 70 and the clamping blocks 92 is now even smaller than in FIG. 10.

In FIGS. 14–16 the control knob 44 has been moved completely through the range of transitional positions to its most proximal position, the turbine carriage-locked position. In this position, the brake continues to be engaged while the proximal end portion of the clamp control tube 76, acting as a wedge, has been urged between the clamping blocks 92, spacing the clamping surfaces 93 from each other and moving the guide wire clamp into its guide wire-released position. When the control knob 44 has been moved into the turbine-locked position and the guide wire clamp has been moved into its guide wire-released position, both the drive shaft 21 and the handle of the atherectomy device may be advanced over the guide wire 20 (at the beginning of the procedure), the guide wire 20 may be repositioned (during the atherectomy procedure), or the guide wire 20 may be removed from the device (at the end of the procedure). When the control knob 44 is moved into the turbine-locked position the brake becomes automatically engaged with the turbine well before the clamp is released; thus there is no opportunity for the turbine and drive shaft 21 to rotate when the guide wire 20 is unclamped. Braking the turbine wheel 34 in the turbine-locked position assures operational safety of the device because the turbine will not rotate in the turbine carriage-locked position even if compressed gas is supplied to the turbine.

The sequence of operation of the brake and clamp when the control knob 44 is moved from the turbine carriage-locked position to the turbine carriage-unlocked position is just the reverse of the above description, with the clamp being moved into its guide wire-clamped position before the brake is released.

FIGS. 17–18 depict a second embodiment of the atherectomy handle of the invention. This embodiment functions essentially identically to the first embodiment depicted in FIGS. 6–16, but a few of the components are modified for more efficient production of the device.

The distal end of the outer telescopic tube 76' is flared outwardly to define a flange 77, eliminating the need to attach the outer collar 89 utilized in the first embodiment. The abutment 80' is simply a washer disposed between the distal end of the brake shoe engagement spring 78 and the flange 77 at the distal end of the outer telescopic tube 76'. The brake shoe 50' includes a proximally extending cylindrical portion 61 which has a proximal end 63 that abuts the washer 80' when the control knob 44 and turbine carriage 30 are moved proximally to the range of transitional positions and then into the turbine carriage-locked position. The brake shoe biasing mechanism consists of a resilient O-ring 54' rather than the coil spring shown in FIGS. 6–16. The distal end of the clamp control tube 70' has a radially outwardly extending flange 85 that is captured within the central cavity 83' in the brake shoe 50' (the cavity being defined in part by a washer 64 which is glued or otherwise secured within the proximally extending cylindrical portion 61 of the brake shoe 50'). As with the prior embodiment, the central cavity 83 of the brake shoe 50' desirably is longitudinally longer than the flange 85 of the clamp control tube 70', permitting limited longitudinal movement of the clamp control tube 70' with respect to the brake shoe 50'. Preferably the central cavity 83 is at least about 1 mm longer than the thickness of the flange 85 of the clamp control tube 70', permitting at least about 1 mm of longitudinal movement of the clamp control tube 70' with respect to the brake shoe 50'.

FIG. 17 depicts this embodiment with the control knob 44 (and the associated turbine carriage 30 and other connected components) located in the range of turbine carriage-unlocked positions, and FIG. 18 shows the configuration of the device when the control knob 44 has been moved to the turbine carriage-locked position. In FIG. 17, the brake is disengaged and the clamp is in its guide wire-clamped position, securing the guide wire 20 against longitudinal and rotational movement. In this position, the abutment 80' is spaced away from the proximally extending cylindrical portion of brake shoe 50', and the proximal end of the clamp control tube 70' is spaced away from the clamping blocks 92.

In FIG. 18 the control knob 44 (together with the associated turbine carriage 30 and other connected components) has been moved to the turbine carriage-locked position. The abutment 80' is firmly pressed against the brake shoe 50' so that the brake shoe has moved from its brake shoe-released position into its brake shoe-engaged position and is engaged with the turbine wheel, preventing rotation of the turbine and the drive shaft. FIG. 18 also demonstrates that when the control knob 44 has been moved into the turbine carriage-locked position, the proximal end portion of the clamp control tube 70' has been inserted between the clamping blocks 92, functioning as the clamp control mechanism to move the clamp from its guide wire-clamped position to its guide wire-released position, permitting the guide wire 20 to be placed in the atherectomy device, to be repositioned or removed.

FIGS. 19–21C depict another embodiment of the atherectomy handle of the invention. In this embodiment the turbine carriage 30" has a generally cylindrical inner cavity 37 in which the turbine and the distal portion of the brake shoe 50" are disposed. The distal portion of the brake shoe 50" preferably has a generally cylindrical shape that is closely received in the turbine carriage cavity 37. The proximal portion of the brake shoe 50", however, preferably has a non-cylindrical shape, and the turbine carriage 30" includes a radially inwardly extending portion 35 which defines a complementary non-cylindrical opening in the proximal portion of the turbine carriage 30". One possible non-cylindrical shape for these components is illustrated in the cross-section shown in FIG. 21A. Other suitable shapes may also be utilized. The non-cylindrical shape of the proximal portion of the brake shoe 50" and the corresponding non-cylindrical shape of the opening in the turbine carriage 30" (through which the proximal portion of the brake shoe extends) prevent rotation of the brake shoe 50" with respect to the turbine carriage 30". This is a necessary condition for the brake shoe 50" to perform its braking function when it engages the turbine wheel 34.

The brake shoe 50" in this embodiment includes a turbine wheel engaging surface 51 which is positioned to define at least part of a wall of a turbine wheel chamber 39 containing the turbine wheel 34. The brake shoe biasing spring is not utilized and is not necessary in this embodiment because whenever compressed gas is supplied to the turbine wheel 34 to rotate the turbine the compressed gas will exert pressure on the turbine wheel engaging surface 51 of the brake shoe 50", thereby urging the brake shoe 50" to move away from the turbine wheel 34.

The embodiment of FIGS. 19–21C utilizes a modified clamp control tube 70" which is telescopically received within a central lumen of a modified clamp housing 90". The distal end portion of the clamp control tube 70" is rigidly secured to the brake shoe 50" with the distal end of the clamp control tube 70" engaging the shoulder 60" of the brake shoe 50". The inner polytetrafluoroethylene lining 72" of the clamp control tube 70" extends distally slightly beyond the end of the clamp control tube 70".

The embodiment shown in FIGS. 19–21C includes an alternate configuration of a turbine carriage lock for automatically restraining the turbine carriage 30" from longitudinal movement with respect to the handle when the turbine carriage 30" is moved longitudinally to the prime mover-locked position. The turbine carriage lock utilizes a pair of releasably interlocking members. One of the interlocking members comprises a pair of tabs 31 extending proximally from the turbine carriage 30", each tab having a radially inwardly extending shoulder 33. The other interlocking member is a complementary ridge carried by the handle for releasable engagement with the radially inwardly extending shoulder 33 of the tabs 31. Although the complementary ridge could be carried directly by the handle housing 10, in the embodiment depicted in FIGS. 19–21C the complementary ridge 101 is a generally annular ridge carried by a housing 90" of the guide wire clamp, the clamp housing 90" in turn being secured to the handle housing 10.

FIGS. 19–20 and 21B–21C illustrate an alternate brake shoe engagement mechanism which is comprised of a generally disk-shaped leaf spring 55 carried by the distal end of the clamp housing 90", the disk-shaped leaf spring 55 functioning both as the abutment and as the brake shoe engagement spring for causing the brake shoe to move from its brake shoe-released position to its brake shoe-engaged position. Details of a preferred configuration for the disk-shaped leaf spring 55 are illustrated in FIGS. 21B–21C. The disk-shaped leaf spring 55 is generally circular in shape, having a peripheral base portion 49, an upwardly angled intermediate portion 53, and a raised center portion 57. Relief slots 59 are provided along the upwardly angled portion 57 and the raised center portion 53 to permit deflection of these sections under pressure, the size and locations of these slots 59, along with the thickness and type of material utilized, determine the spring constant for the disk-shaped leaf spring 55.

FIG. 19 shows this embodiment with the control knob 44 (together with the associated turbine carriage 30" and other connected components) located in the range of turbine carriage-unlocked positions, and FIG. 20 shows the configuration of the device when the control knob 44 has been moved to the turbine carriage-locked position. In FIG. 19, the brake is disengaged from the turbine, the clamp is in its guide wire-clamped position, securing the guide wire 20 against longitudinal and rotational movement, and the prime mover carriage lock is disengaged, with the radially inwardly extending shoulder 33 spaced away from the complementary ridge 101 of the guide wire clamp housing 90".

In FIG. 20 the control knob 44 (together with the associated turbine carriage 30" and other connected components) has been moved to the turbine carriage-locked position. The radially inwardly extending shoulder 33 is engaged with the complementary ridge 101 of the clamp housing 90". The brake shoe 50' is firmly pressed against the disk-shaped leaf spring 55 so that the brake is engaged, preventing rotation of the turbine and drive shaft 21. The proximal end portion of the clamp control tube 70" has been inserted between the clamping blocks 92, functioning as the clamp control mechanism to move the clamp from its guide wire-clamped position to its guide wire-released position, permitting the guide wire 20 to be repositioned or removed.

FIGS. 22–25B depict details of the structure and function of the preferred clamp utilized in the embodiments of FIGS. 6–18. In addition to releasing the guide wire 20 from the clamp each time when the turbine carriage and the turbine are placed in the prime mover-locked position, this clamp also enables the operator to release the guide wire 20 from the clamp even when the clamp control mechanism is in the guide wire-clamped position. A pair of opposed clamping blocks 92 is disposed in a slot 91 in the clamp housing 90. A clamp biasing mechanism comprised of at least one clamp biasing spring is provided for biasing at least one of the clamping blocks 92 toward the other to clamp the guide wire 20. Each of the clamping blocks 92 includes a clamping surface 93 and a spring engaging surface 131. The clamp biasing spring preferably comprises a resilient collar 94 encircling the clamping blocks 92, the size and shape of the clamping blocks 92 and the resilient collar 94 being selected so that the resilient collar 94 pushes on the spring engaging surfaces 131 to bias the clamping blocks 92 toward each other, clamping the guide wire 20 between the clamping surfaces 93.

The handle housing 10 is sized and shaped with respect to the collar 94 to permit manual compression of the collar 94. Preferably the handle housing 10 substantially surrounds the collar 94, the handle housing 10 including at least one opening 18 (and preferably two openings 18) aligned with the collar 94 to permit manual compression of the collar 94. Thus, the resilient circumferential collar 94 may be manually compressed (through the openings 18 in the handle housing 10) to a shape in which the collar 94 does not bias the clamping blocks 92 toward each other and the guide wire 20 is released from the clamp.

The clamp housing 90 maintains alignment of the clamping blocks 92 with respect to each other and with respect to the resilient collar 94, the handle housing 10 and the guide wire 20.

Figure 23:
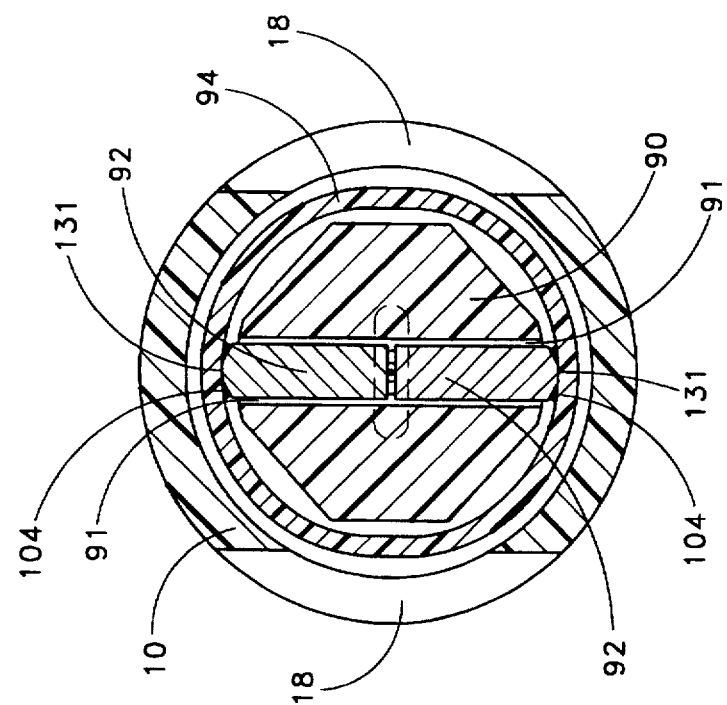
FIG. 23 is a transverse cross-sectional view of FIG. 22, taken along lines 23—23 thereof.
Figure 23A:
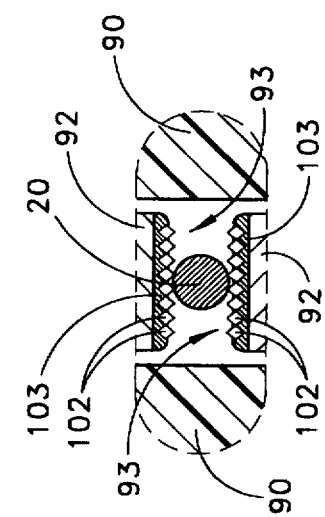
FIG. 23A is an enlarged view of a portion of FIG. 23.
Figure 22:
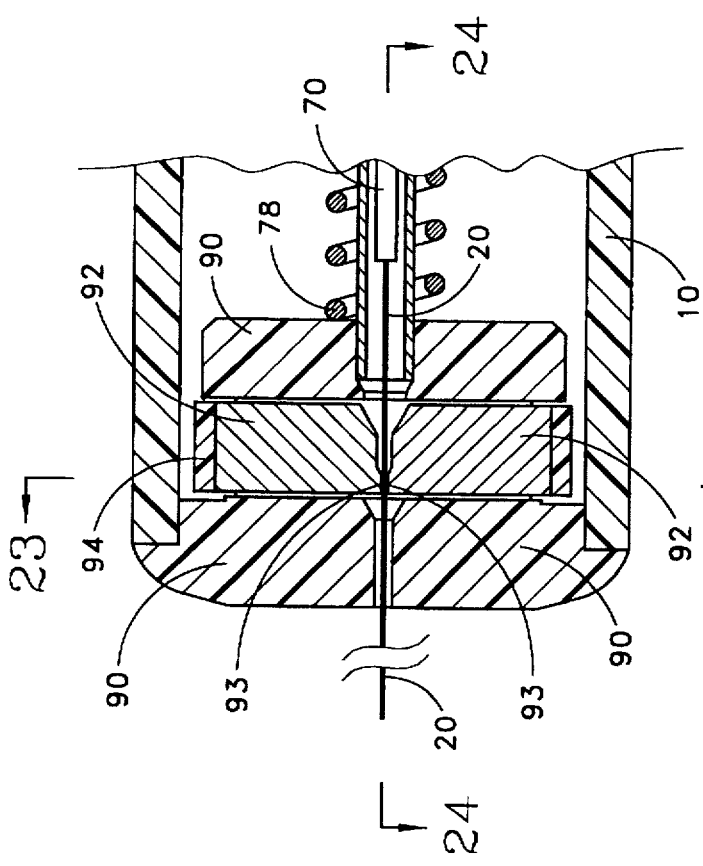
FIG. 22 is a longitudinal cross-sectional view of the clamp portion of the atherectomy device of the invention.

As is illustrated in FIG. 23A, the clamping surfaces 93 of the clamping blocks 92 may be provided with a coating of diamond chips 102, secured by a suitable bonding material 103, to provide a better grip on the guide wire 20. Other equivalent techniques may be utilized to provide adequate engagement of the clamping surfaces 93 with the guide wire 20. (For simplicity in illustration the polytetrafluoroethylene lining 72 of the clamp control tube 70 is not shown in FIG. 23 or 23A, or in a number of the other ensuing drawings illustrating different clamp embodiments.)

Figure 24:
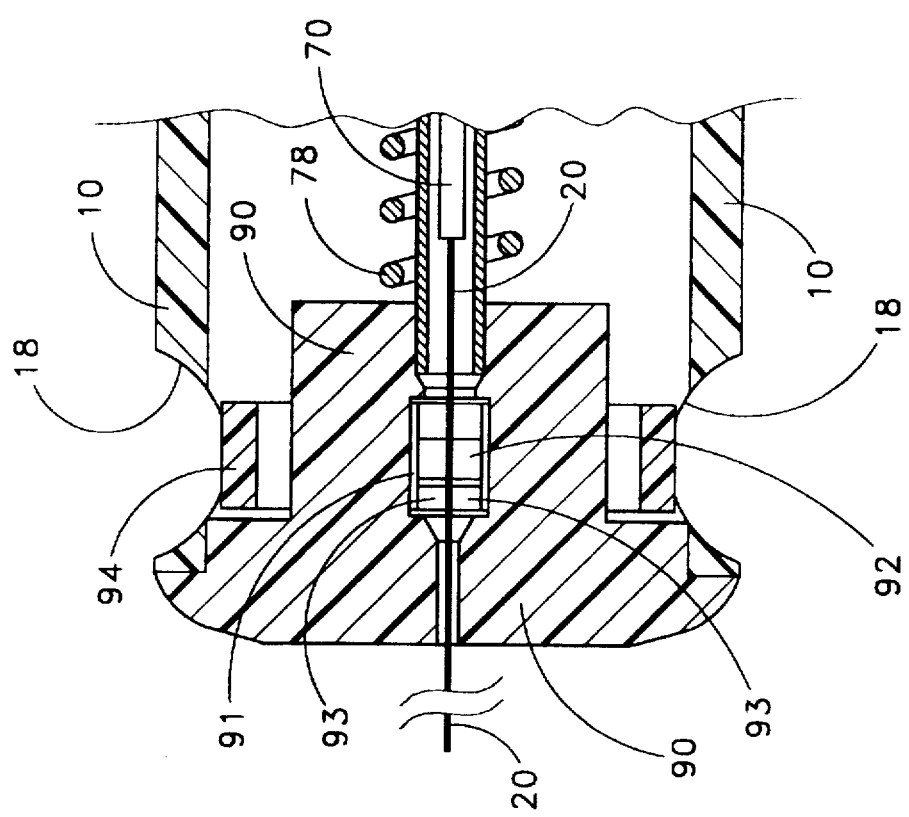
FIG. 24 is a longitudinal cross-sectional view of FIG. 23, taken along lines 24—24 thereof.

FIG. 24 is a cross-sectional view of the clamp taken along lines 24—24 of FIG. 23. This view shows additional details of the clamp housing 90 which contains the clamping blocks 92, and also illustrates the alignment of a pair of side openings 18 in the handle housing 10 with the resilient circumferential collar 94. In FIG. 25A the guide wire 20 is clamped between the clamping surfaces 93 of the clamping blocks 92. As may been seen by comparing the shape of the resilient collar 94 in FIGS. 25A and 25B, the side openings 18 permit manual compression of the collar 94 to a shape in which the deformed collar 94 does not bias the clamping blocks 92 toward each other and in which the guide wire 20 is released from the clamp even if the clamp control mechanism is in the guide wire-clamped position. In FIG. 25B the clamping blocks are depicted as being spaced away from the guide wire-in this embodiment of the clamp each clamping block 92 is secured (such as by an adhesive 104) to the resilient collar 94 so that when the collar 94 is compressed it actually pulls the clamping blocks 92 away from the guide wire 20. The use of such an adhesive 104 is not necessarily required, however.

Figure 26A:
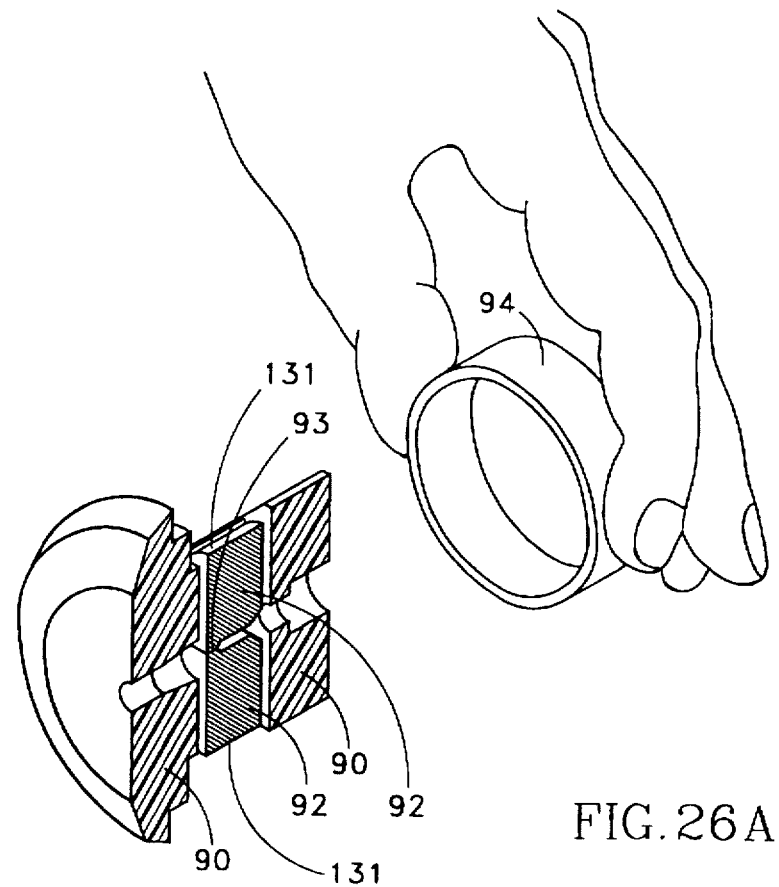
FIGS. 26A-26D depict a sequence of steps for mounting a resilient collar on a housing of the guide wire clamp of the atherectomy device of the invention.
Figure 26B:
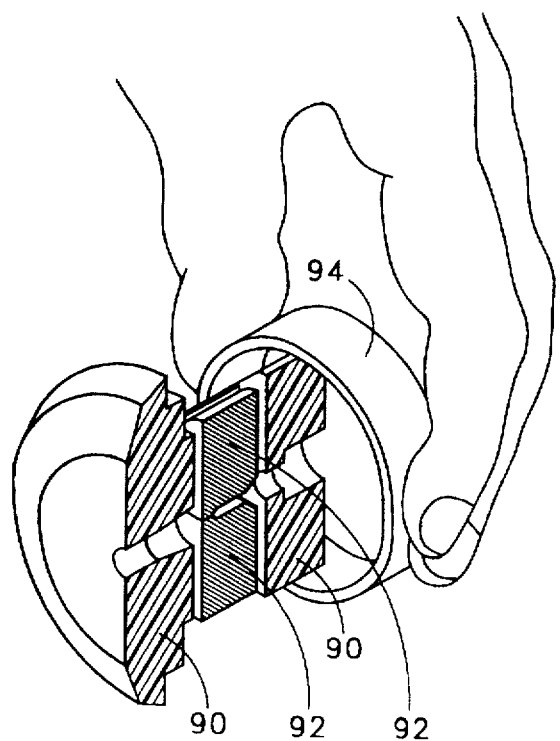
Figure 26C:
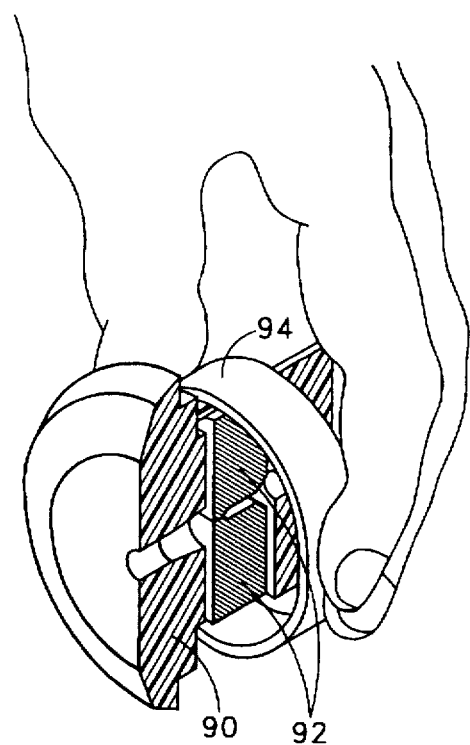
Figure 26D:
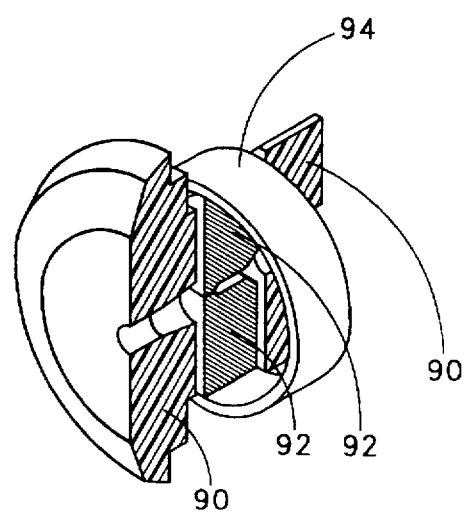

FIGS. 26A–26D depict a method for mounting the resilient collar 94 on the clamp housing 90. In FIG. 26A the clamping blocks 92 have been located in their proper positions within the clamp housing 90. The resilient collar 94 is then compressed (so that it assumes an oval shape) and slipped over the distal end portion of the clamp housing 90, as is shown in FIGS. 26B–26C. When the collar 94 is released, it preferably retains a slightly oval shape, thereby continually pressing on the spring engaging surfaces 131 of the clamping blocks and biasing the clamping blocks 92 and their clamping surfaces 93 toward each other. (In most of the drawings the collar 94 appears to be substantially round, but preferably it is slightly oval in shape.) The height of the distal end portion of the clamp housing 90 is greater than the distance between the spring engaging surfaces 131 of the clamping blocks 92. The height of the distal end portion of the clamp housing 90 is also substantially greater than its width, thus permitting the collar 94 to be moved easily into its position over the distal end portion of the clamp housing 90 when the collar 94 is compressed to an oval shape. Because the portions of the clamp housing 90 located just proximally and distally of the collar 94 have a greater height than the inner vertical diameter of the collar, these portions of the housing maintain the collar 94 in longitudinal alignment with the clamping blocks 92 and with the handle housing 10.

Figure 27:
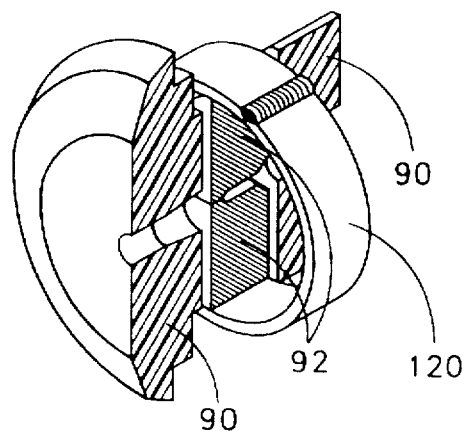
FIG. 27 depicts an alternate embodiment of a clamp biasing spring usable in the atherectomy device of the invention.
Figure 28:
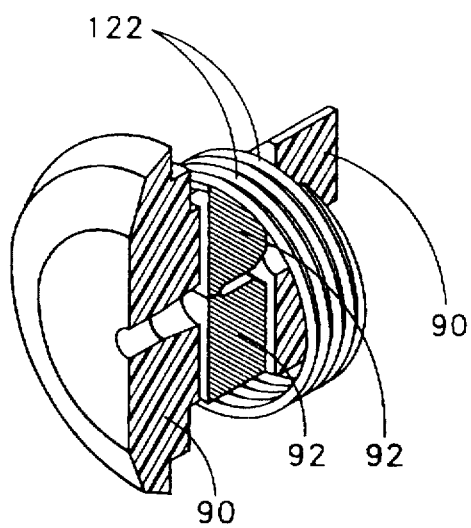
FIG. 28 depicts another embodiment of a clamp biasing spring usable in the atherectomy device of the invention.
Figure 29:
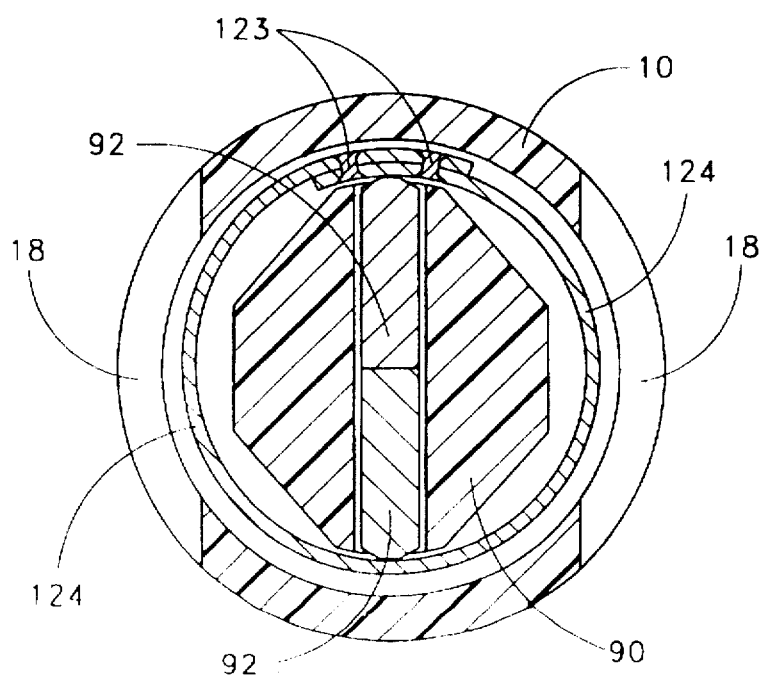
FIG. 29 depicts another embodiment of a clamp biasing spring usable in the atherectomy device of the invention.

FIGS. 27–31 illustrate alternate configurations for the clamp biasing spring. In FIG. 27 the clamp biasing spring is formed by welding a strip of metal into a resilient circumferential collar 120. In FIG. 28 a helically wound coil 122 is utilized, and in FIG. 29 rivets 123 are used to secure a strip of metal (preferably nitinol) into a resilient circumferential collar 124.

Figure 31:
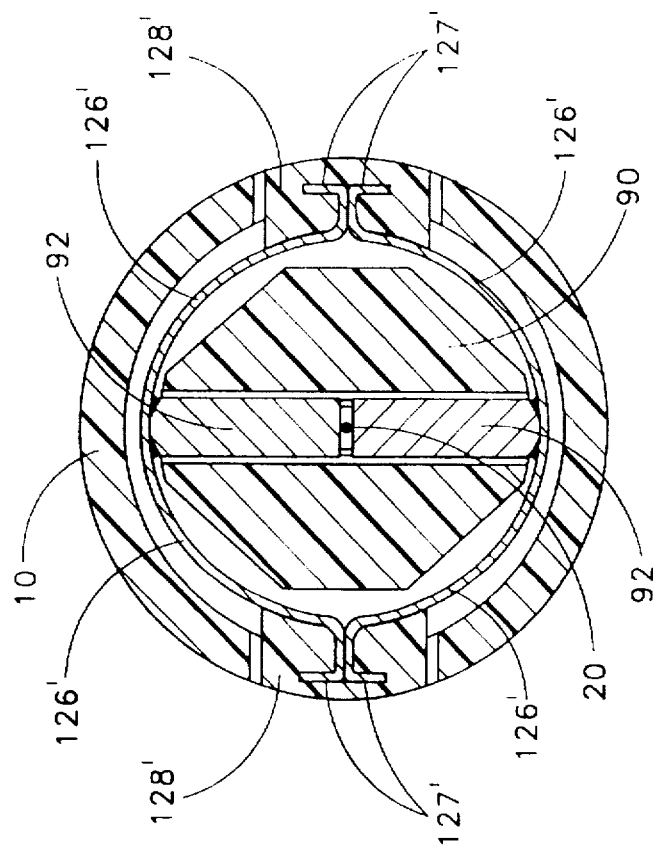
FIG. 31 depicts yet another embodiment of a clamp biasing spring usable in the atherectomy device of the invention.
Figure 30:
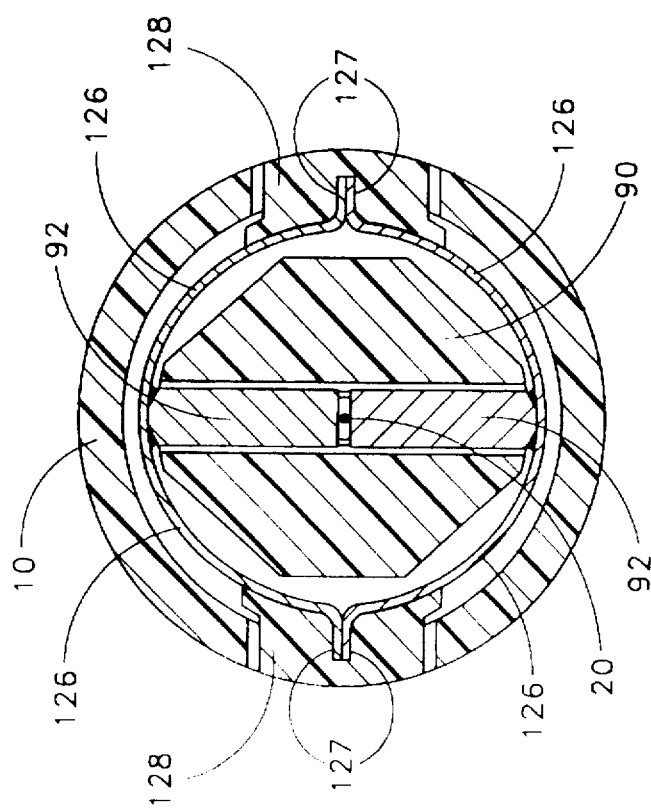
FIG. 30 depicts another embodiment of a clamp biasing spring usable in the atherectomy device of the invention.

In FIG. 30 the clamp biasing spring is comprised of a pair of generally semi-circular bands 126, the respective ends 127 of the bands 126 being secured adjacent to each other by a pair of buttons 128 that are glued or otherwise attached to the bands 126. The buttons 128 extend radially outwardly through the openings 18 in the handle housing 10 to facilitate manual compression of the bands 128. The generally semi-circular bands 126' in FIG. 31 are essentially similar to those of FIG. 30, but the ends 127' of the bands 126' are curved into a shape that facilitates use of insertion molding technology for connecting the ends 127' of the bands 126' to the buttons 128'. Each button 128' may be also molded with an appropriately formed longitudinal slot extending from front to back, and the ends 127' of the bands 128' may then be slid into the respective slots in the buttons 128' to lock the bands 126' into a circumferential collar shape.

Figure 33:
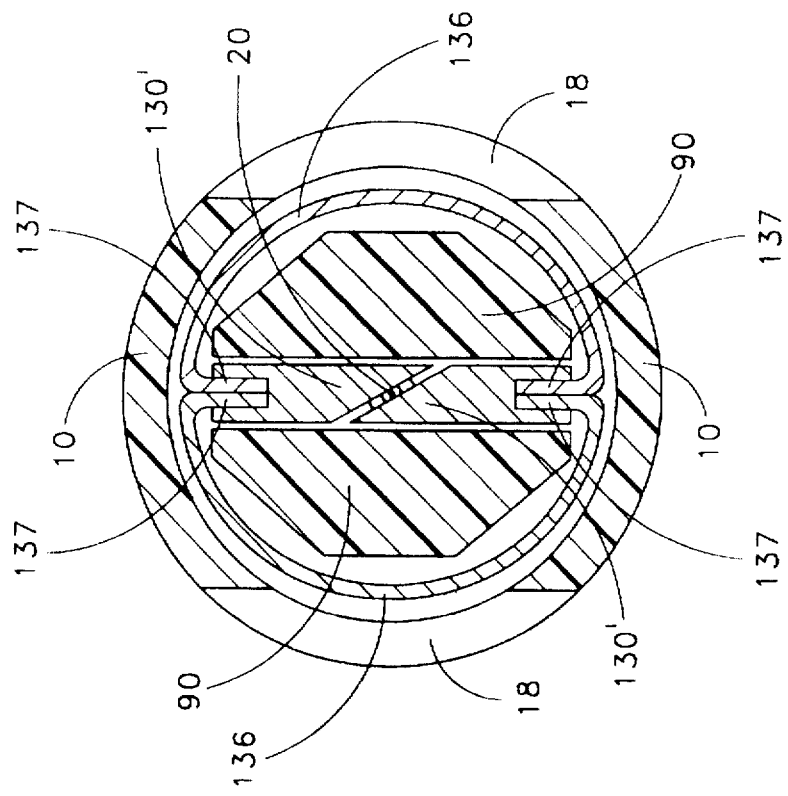
FIG. 33 depicts another embodiment of clamping blocks and a clamp biasing spring usable in the atherectomy device of the invention.
Figure 32:
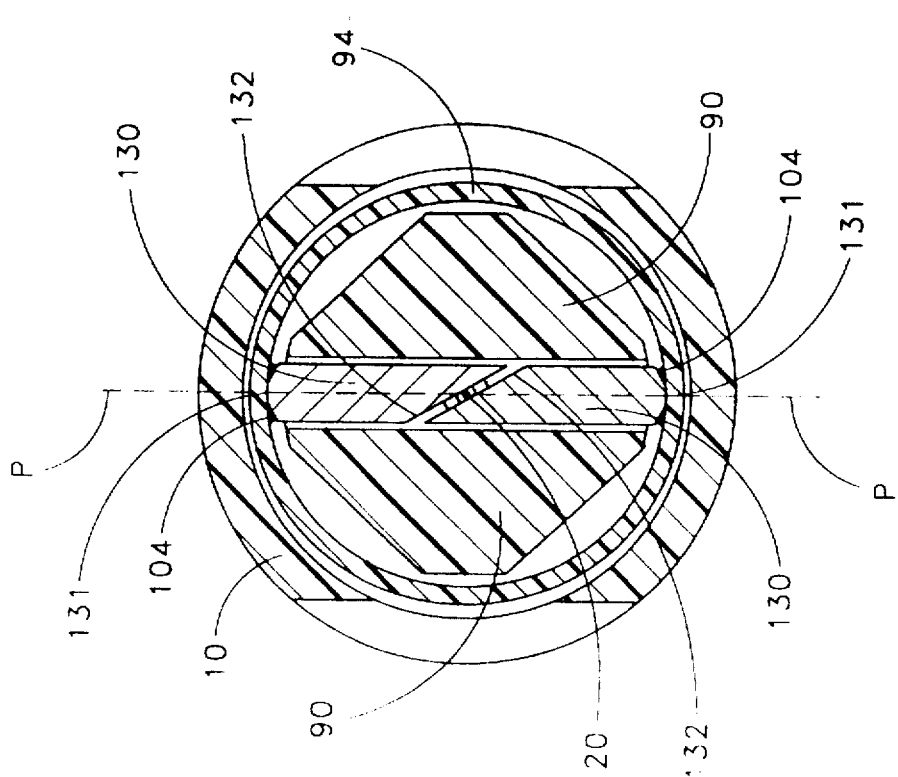
FIG. 32 depicts an alternate embodiment of clamping blocks usable in the atherectomy device of the invention.

FIG. 32 depicts an alternate embodiment for the clamping blocks. In this embodiment the clamping surfaces 132 of the clamping blocks 130 are oriented at an acute angle to a plane "P" which contains (or is parallel to) the longitudinal axis of the guide wire 20, the plane extending from the spring-engaging surface 131 of one of the clamping blocks 130 to the spring-engaging surface 131 of the other clamping block 130. The drive shaft has a primary direction of rotation selected so that frictional torque conveyed by friction from the drive shaft to the guide wire 20 urges the guide wire 20 to rotate in a direction that increases the clamping force exerted by the clamping blocks 130 on the guide wire 20. In this embodiment the clamping blocks 92 preferably are secured at their peripheral ends to the inner surface of the resilient collar 94 by, e.g., a suitable adhesive 104. Coating of the clamping surfaces with diamond grit in this embodiment is not required, but it may be desirable to increase the coefficient of friction between the clamping surfaces and the guide wire by appropriately coating or treating the clamping surfaces. For example, clamping blocks of FIG. 32 may be made from aluminum alloy and their clamping surfaces may be coated with, e.g., aluminum oxide ($Al_2O_3$). In FIG. 33 the clamp biasing spring is comprised of a pair of generally semi-circular bands 136, the respective ends 137 of the bands 136 being secured adjacent to each other within complementary slots formed in the clamping blocks 130'.

FIGS. 34A-34B illustrate another alternate embodiment for the guide wire clamp and its clamping blocks. In this embodiment each clamping block 140 includes a radially central end 142 and a radially peripheral end 144. Each clamping block 140 has a recess 146 near its central end 142, the recess 146 being formed within the clamping block to define a clamping foot 148 at the central end 142 of the clamping block 140. Each clamping block 140 carries a clamping surface 150 on the clamping foot 148, which may be provided with a coating of diamond chips 102, secured by a suitable bonding material 103, to provide a better grip on the guide wire 20 (see FIG. 34C). The opposed clamping blocks 140 are positioned with respect to each other so that the clamping foot 148 of one clamping block 140 is received in the recess 146 of the other clamping block 140. As can be seen in the drawings, the clamping surface 150 of each clamping block 140 preferably is located on what may be referred to as a dorsal surface of the foot 148 of the clamping block 140.

At least one (and preferably both) of the clamping blocks 140 includes one or more slots 152 near its peripheral end 144 for receiving at least one clamp biasing spring 154 which urges the peripheral ends 144 of the clamping blocks 140 away from each other, thereby moving the clamping feet 148 and the clamping surfaces 150 toward each other. A pair of clamp biasing springs 154 may be used as shown in FIGS. 34A-34B, opposite ends of the springs 154 being received in corresponding slots 152 in the clamping blocks 140. Alternately a single circumferential collar or any other suitable biasing mechanism may be employed.

Figure 35:
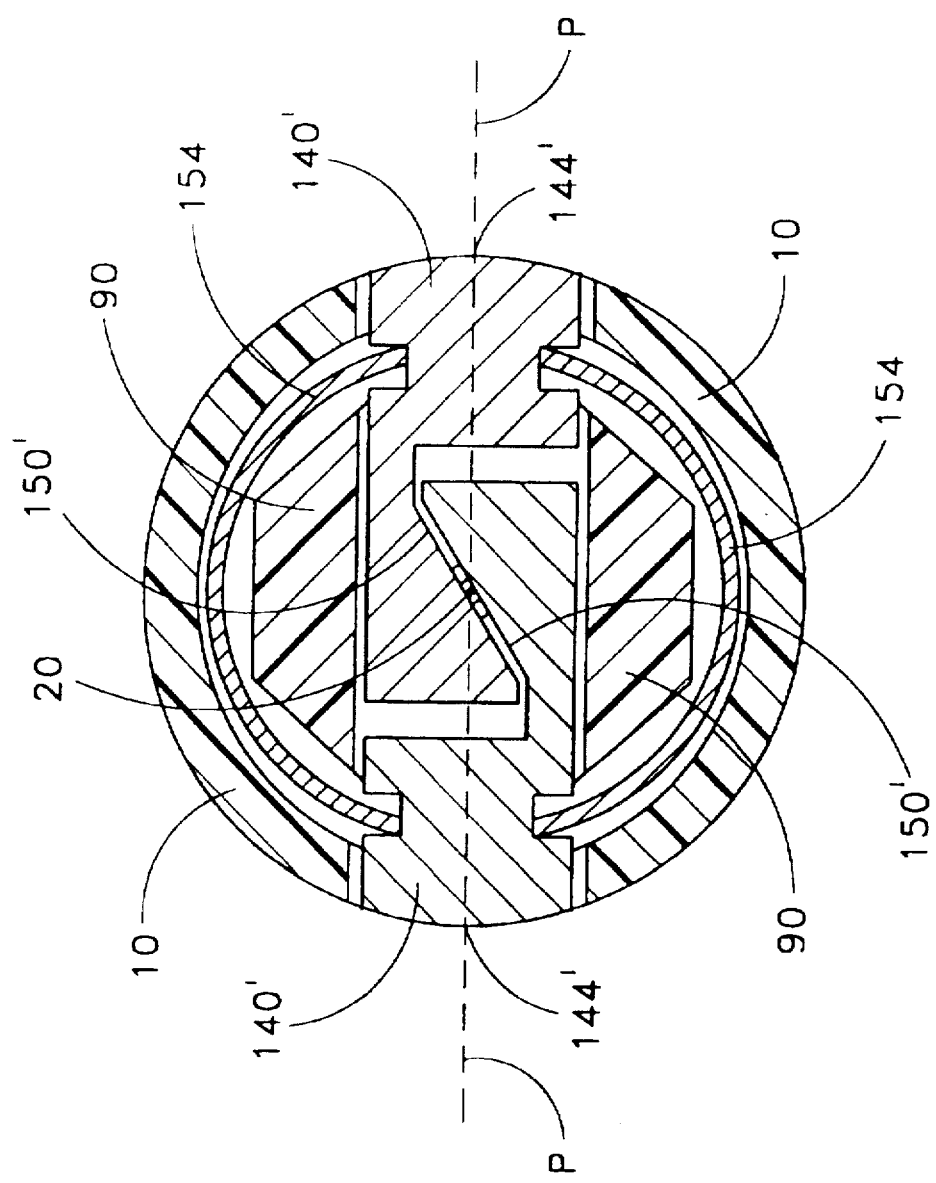
FIG. 35 depicts another embodiment of clamping blocks usable in the atherectomy device of the invention.
Figure 36:
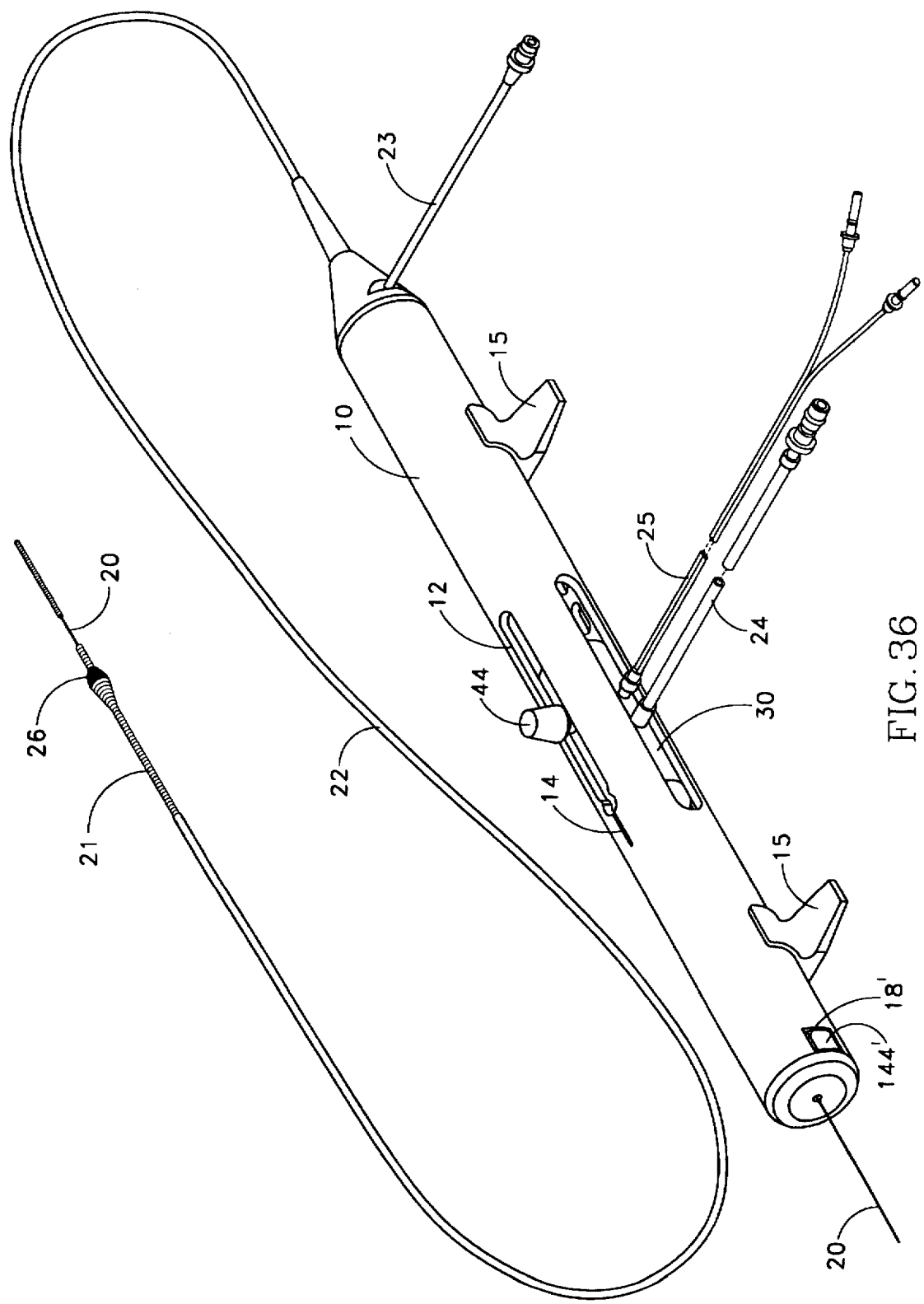
FIG. 36 is a perspective view of an atherectomy device of the invention utilizing the guide wire clamp design of any of FIGS. 30-31 or 34A-35.

In FIGS. 34A-34C the clamping surfaces 150 of the clamping blocks 140 are generally parallel to each other and to the longitudinal axis of the guide wire 20. As is shown in FIG. 35, the clamping surfaces 150' of the two clamping blocks 140' may be oriented at an acute angle to a plane "P" which contains (or is parallel to) the longitudinal axis of the guide wire 20, the plane extending from the radially peripheral end 144' of one of the clamping blocks 140' to the radially peripheral end 144' of the other clamping block 140'. In this embodiment the drive shaft has a primary direction of rotation selected so that frictional torque conveyed by friction from the drive shaft to the guide wire 20 urges the guide wire 20 to rotate in a direction that increases the clamping force exerted by the clamping blocks on the guide wire. The handle housing 10 is sized and shaped with respect to the clamp and its clamping blocks 140 or 140' to permit application of manual pressure on the clamping blocks 140 or 140', thereby compressing the clamp biasing springs 154 and releasing the guide wire 20 from the clamp. FIG. 36 illustrates a handle housing 10 having a pair of generally square openings 18' through which the peripheral ends 144' of the clamping blocks 140' extend (one of the openings not being visible since it is on the opposite side of the handle housing 10). Generally square openings of this type in the handle housing 10 may also be used to provide access to the clamping blocks 140 shown in FIGS. 34A-34B or to the resilient collar buttons 128 and 128' shown in FIGS. 30-31.

Figure 37B:
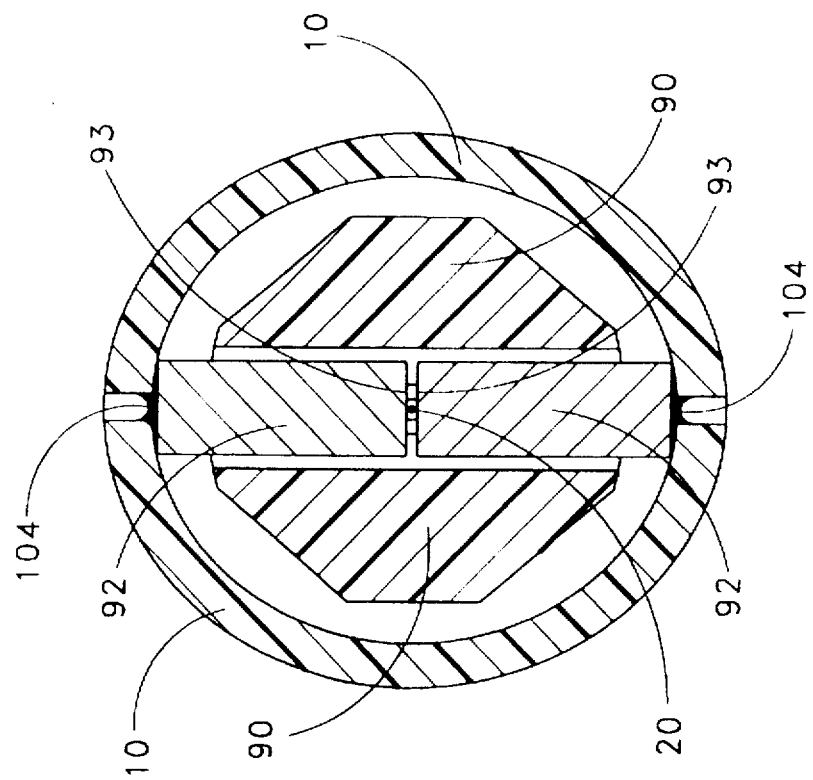
FIG. 37B depicts the clamp of FIG. 37A in a moved position.
Figure 37A:
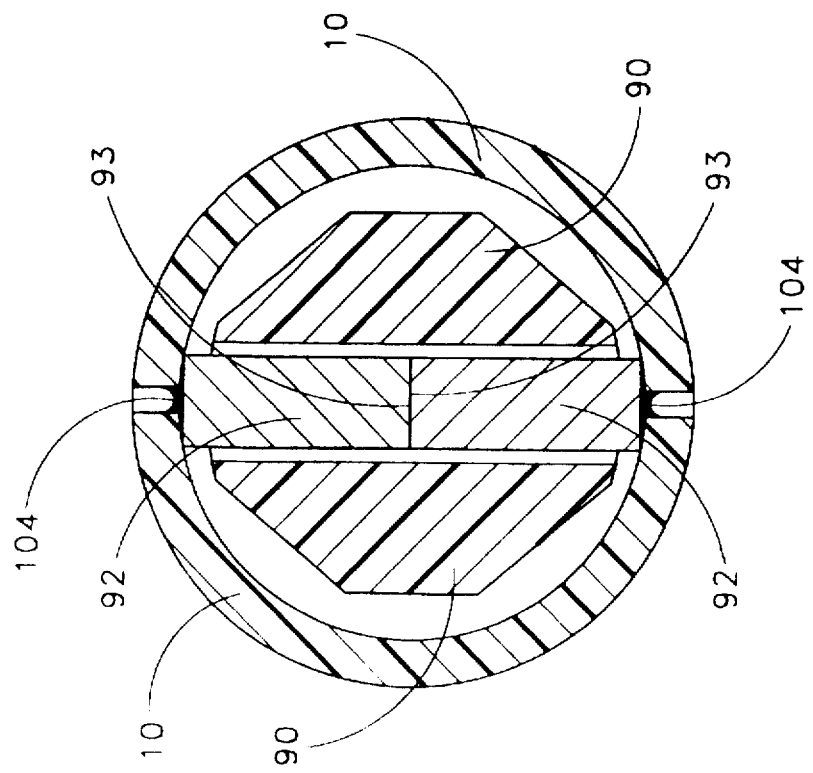
FIG. 37A depicts yet another embodiment where the handle housing is sufficiently resilient to function as the clamp biasing spring.

FIGS. 37A-37B depict another embodiment where the handle housing 10, which substantially surrounds the clamp, is sufficiently resilient to function as the clamp biasing spring. In this embodiment the clamping blocks 92 are secured at their peripheral ends to the inner wall of the handle housing 10 by a suitable adhesive 104. FIG. 37A depicts the clamping blocks with their clamping surfaces 93 abutting each other, and FIG. 37B shows the clamping blocks 92 with the guide wire 20 inserted between the clamping surfaces 93. In this condition the handle housing 10 in FIG. 37B is oval in shape (somewhat exaggerated in this drawing for illustrative purposes), its resilient nature providing sufficient force to clamp the guide wire securely between the clamping surfaces 93.

While a preferred embodiment of the present invention has been described, it should be understood that various changes, adaptations and modifications may be made therein without departing from the spirit of the invention and the scope of the appended claims.

What is claimed is:

1. An atherectomy device comprising:

a handle;

a rotatable prime mover movable longitudinally with respect to the handle;

a rotatable drive shaft having a proximal end connected to the prime mover for rotation and longitudinal movement therewith;

a prime mover brake associated with the handle, the brake being selectively movable with respect to the prime mover from a brake-engaged position, preventing rotation of the prime mover and the drive shaft, to a brake-released position permitting rotation of the prime mover and the drive shaft;

a guide wire disposed within the drive shaft and having a proximal portion extending from the proximal end of the drive shaft;

a guide wire clamp associated with the handle to releasably clamp the proximal portion of the guide wire, the clamp being movable from a guide wire-clamped position to a guide wire-released position.

2. The atherectomy device of claim 1, further comprising a clamp control mechanism for controlling the position of the clamp.

3. The atherectomy device of claim 2 wherein the prime mover is movable with respect to the handle from a prime mover-locked position, in which position the prime mover is restrained from longitudinal movement with respect to the handle, and in which position the prime mover brake is in its brake-engaged position and the clamp control mechanism is in a clamp-released position, to a range of prime mover unlocked positions, in which positions longitudinal movement of the prime mover with respect to the handle is substantially not restrained and in which positions the prime mover brake is in its brake-released position and the clamp control mechanism is in a clamp-engaged position.

4. The atherectomy device of claim 3 wherein the brake comprises a brake shoe and a brake shoe engagement mechanism for moving the brake shoe from a brake shoe-released position to a brake shoe-engaged position where the brake shoe is operatively engaged with the prime mover to prevent rotation of the prime mover and the drive shaft.

5. The atherectomy device of claim 4 wherein the prime mover, the brake shoe and the brake shoe engagement mechanism are positioned with respect to one another so that as the prime mover is moved to its prime mover-locked position the brake shoe encounters the brake shoe engagement mechanism, which causes the brake shoe to move from its brake shoe-released position to its brake shoe-engaged position.

6. The atherectomy device of claim 3 wherein the brake comprises a brake shoe and a brake shoe biasing mechanism for biasing the brake shoe away from the prime mover.

7. The atherectomy device of claim 6 wherein the brake further comprises a brake shoe engagement mechanism for overriding the brake shoe biasing mechanism and causing the brake shoe to move from its brake shoe-released position to its brake shoe-engaged position.

8. The atherectomy device of claim 7 wherein the prime mover, the brake shoe, and the brake shoe engagement mechanism are positioned with respect to one another so that as the prime mover is moved to its prime mover-locked position the brake shoe encounters the brake shoe engagement mechanism, which overrides the brake shoe biasing mechanism, causing the brake shoe to move from its brake shoe-released position to its brake shoe-engaged position, thus preventing rotation of the prime mover.

9. The atherectomy device of claim 5 or 8 wherein the brake shoe is operatively connected to the clamp control mechanism.

10. The atherectomy device of claim 9 wherein the brake shoe engagement mechanism includes a resilient element positioned so that as soon as the brake shoe engages the prime mover, further advancement of the prime mover into its prime mover-locked position causes the brake shoe to compress the resilient element of the brake shoe engagement mechanism and to move the clamp control mechanism into its clamp-released position thereby moving the clamp into its guide wire-released position.

11. The atherectomy device of claim 10 wherein the resilient element comprises a spring.

12. The atherectomy device of claim 11 wherein the spring is a coil spring.

13. The atherectomy device of claim 11 wherein the spring is a leaf spring.

14. The atherectomy device of claim 7 wherein the brake shoe engagement mechanism comprises a resilient element operatively positioned between the brake shoe and the handle so that when the prime mover is moved to the prime mover-locked position the brake shoe operatively engages the resilient element.

15. The atherectomy device of claim 14 wherein the resilient element of the brake engagement mechanism is carried by an outer telescopic tube, the outer telescopic tube having a lumen for receiving a clamp control tube therein, the outer telescopic tube being secured with respect to the guide wire clamp, and having a distal end carrying restriction means for retaining the resilient element on the tube.

16. The atherectomy device of claim 15 wherein the brake shoe engagement mechanism also includes an abutment positioned between the resilient element and the brake shoe.

17. The atherectomy device of claim 16 wherein the abutment is carried by the outer telescopic tube.

18. The atherectomy device of claim 16 wherein the resilient element, the abutment and the brake shoe are positioned with respect to one another so that when the prime mover is moved to the prime mover-locked position the brake shoe encounters the abutment, causing the resilient element of the brake shoe engagement mechanism to override the brake shoe biasing mechanism and to move the brake shoe from its brake shoe-released position to its brake shoe-engaged position, thus preventing rotation of the prime mover.

19. The atherectomy device of claim 14 wherein the clamp includes a housing, the resilient element of the brake shoe engagement mechanism being carried by the clamp housing.

20. The atherectomy device of claim 19 wherein the clamp housing has a lumen for telescopically receiving a clamp control tube therein.

21. The atherectomy device of claim 2 wherein the prime mover, the prime mover brake and the clamp control mechanism are operatively interconnected so that when the prime mover is in a range of prime mover-unlocked positions, in which positions the prime mover is substantially not restrained from longitudinal movement with respect to the handle, the prime mover brake is in its brake-released position and the clamp control mechanism is in a clamp-engaged position.

22. The atherectomy device of claim 2 wherein the prime mover, the prime mover brake and the clamp control mechanism are operatively interconnected so that when the prime mover is in a prime mover-locked position, in which position the prime mover is restrained against longitudinal movement with respect to the handle, the prime mover brake is in its brake-engaged position and the clamp control mechanism is in a clamp-released position.

23. The atherectomy device of claim 2 wherein the prime mover, the prime mover brake and the clamp control mechanism are operatively interconnected so that as the prime mover is moved toward a brake-engaged position the brake enters its brake-engaged position, substantially preventing rotation of the prime mover, before the clamp control mechanism causes the clamp to move into its guide wire-released position.

24. The atherectomy device of claim 2 wherein the prime mover, the prime mover brake and the clamp control mechanism are operatively interconnected so that as the prime mover is moved from a brake-engaged position where the brake is operatively engaged with the prime mover to a brake-released position where the brake is disengaged from the prime mover, the clamp control mechanism causes the clamp to move into its guide wire-clamped position before the brake moves into its brake-released position.

25. The atherectomy device of claim 1 wherein the brake comprises a brake shoe which is selectively movable with respect to the prime mover from a brake shoe-released position to a brake shoe-engaged position where the brake shoe is operatively engaged with the prime mover to prevent rotation of the prime mover and the drive shaft.

26. The atherectomy device of claim 25 wherein the brake further comprises a brake shoe engagement mechanism for moving the brake shoe from the brake shoe-released position to the brake shoe-engaged position.

27. The atherectomy device of claim 25 wherein the brake further comprises a brake shoe biasing mechanism for biasing the brake shoe away from the prime mover, and a brake shoe engagement mechanism for overriding the brake shoe biasing mechanism and causing the brake shoe to move from its brake shoe-released position to its brake shoe-engaged position.

28. The atherectomy device of claim 25, 26 or 27 wherein the brake shoe is operatively connected to a clamp control mechanism for controlling the position of the guide wire clamp.

29. The atherectomy device of claim 28 wherein the clamp is comprised of a pair of opposed clamping blocks, each having a clamping surface, and a clamp biasing mechanism for biasing at least one of the clamping surfaces toward the other to clamp the guide wire.

30. The atherectomy device of claim 29 wherein the clamp control mechanism comprises a clamp control rod having a proximal end portion and a distal end portion, the distal end portion of the clamp control rod being operatively connected to the brake shoe.

31. The atherectomy device of claim 30 wherein the distal end portion of the clamp control rod includes a radially outwardly extending flange, the brake shoe including a central cavity capturing the radially outwardly extending flange.

32. The atherectomy device of claim 31 wherein the central cavity of the brake shoe is longitudinally longer than the flange of the clamp control rod, permitting limited longitudinal movement of the clamp control rod with respect to the brake shoe.

33. The atherectomy device of claim 32 wherein the central cavity of the brake shoe is at least about 1 mm longer than the flange of the control rod, permitting at least about 1 mm of longitudinal movement of the control rod with respect to the brake shoe.

34. The atherectomy device of claim 30 wherein the clamp control rod comprises a tube having a lumen for receiving the guide wire therethrough.

35. The atherectomy device of claim 30 wherein the clamp control rod is movable longitudinally from a range of disengaged positions where the clamp control rod permits the clamp to be in its guide wire-clamped position to an engaged position where the clamp control rod causes the clamp to move into its guide wire-released position.

36. The atherectomy device of claim 35 wherein the brake shoe engagement mechanism comprises a resilient element and wherein the clamp control rod, the brake shoe and the brake shoe engagement mechanism are positioned with respect to one another so that as the clamp control rod is moved from its range of disengaged positions to its engaged position the resilient element of the brake shoe engagement mechanism causes the brake shoe to move into its brake shoe-engaged position before the clamp control rod causes the clamp to move into its guide wire-released position.

37. The atherectomy device of claim 36 wherein the resilient element comprises a spring.

38. The atherectomy device of claim 37 wherein the spring is a coil spring.

39. The atherectomy device of claim 37 wherein the spring is a leaf spring.

40. The atherectomy device of claim 35 wherein the clamp control rod causes the clamp to move into its guide wire-released position by wedging the proximal end portion of the rod between the clamping blocks.

41. The atherectomy device of claim 27 wherein the brake shoe engagement mechanism comprises a resilient element operatively positioned between the brake shoe and the handle so that when the prime mover is moved to a prime mover-locked position the brake shoe operatively engages the resilient element.

42. The atherectomy device of claim 41 wherein the resilient element of the brake engagement mechanism is carried by an outer telescopic tube, the outer telescopic tube having a lumen for receiving a clamp control tube therein, the outer telescopic tube being secured with respect to the guide wire clamp, and having a distal end carrying restriction means for retaining the resilient element on the tube.

43. The atherectomy device of claim 42 wherein the brake shoe engagement mechanism also includes an abutment positioned between the resilient element and the brake shoe.

44. The atherectomy device of claim 43 wherein the abutment is carried by the outer telescopic tube.

45. The atherectomy device of claim 43 wherein the resilient element, the abutment and the brake shoe are positioned with respect to one another so that when the prime mover is moved to the prime mover-locked position the brake shoe encounters the abutment, causing the resilient element of the brake shoe engagement mechanism to override the brake shoe biasing mechanism and to move the brake shoe from its brake shoe-released position to its brake shoe-engaged position, thus preventing rotation of the prime mover.

46. The atherectomy device of claim 41 wherein the clamp includes a housing, the resilient element of the brake shoe engagement mechanism being carried by the clamp housing.

47. The atherectomy device of claim 46 wherein the clamp housing has a lumen for telescopically receiving a clamp control tube therein.

48. The atherectomy device of claim 14 or 41 wherein the resilient element comprises a spring.

49. The atherectomy device of claim 48 wherein the spring is a coil spring.

50. The atherectomy device of claim 48 wherein the spring is a leaf spring.

51. The atherectomy device of claim 6 or 27 wherein the prime mover comprises a compressed gas driven turbine having a turbine wheel.

52. The atherectomy device of claim 51 wherein the turbine wheel is disposed within a turbine wheel chamber, the brake shoe biasing mechanism comprising a turbine wheel engaging surface of the brake shoe, the turbine wheel engaging surface being positioned to define at least part of a wall of the turbine wheel chamber so that when compressed gas is supplied to the turbine wheel to rotate the turbine the compressed gas will exert pressure on the turbine wheel engaging surface of the brake shoe, thereby urging the brake shoe away from the turbine wheel.

53. The atherectomy device of claim 6 or 27 wherein the brake shoe biasing mechanism comprises a resilient element operatively positioned between the brake shoe and the prime mover to urge the brake shoe away from the prime mover.

54. The atherectomy device of claim 53 further comprising a prime mover carriage, the resilient element disposed between the brake shoe and the prime mover carriage to urge the brake shoe away from the prime mover.

55. The atherectomy device of claim 54 wherein the resilient element is a spring.

56. The atherectomy device of claim 55 wherein the spring is a coil spring.

57. The atherectomy device of claim 54 wherein the resilient element is a resilient O-ring.

58. The atherectomy device of claim 6 or 27 wherein the prime mover, the brake shoe, and the brake shoe biasing mechanism are carried by a prime mover carriage.

59. The atherectomy device of claim 1 wherein the prime mover comprises a compressed gas driven turbine having a turbine wheel disposed within a turbine wheel chamber.

60. The atherectomy device of claim 59 wherein the brake includes a brake shoe having a turbine wheel engaging surface, the turbine wheel engaging surface being positioned to define at least part of a wall of the turbine wheel chamber so that when compressed gas is supplied to the turbine wheel to rotate the turbine the compressed gas will exert pressure on the turbine wheel engaging surface of the brake shoe, thereby urging the brake shoe away from the turbine wheel.

61. The atherectomy device of claim 1 wherein the prime mover and the prime mover brake are carried by a prime mover carriage.

62. The atherectomy device of claim 1, further comprising a prime mover carriage carrying the prime mover, the prime mover carriage being movable longitudinally with respect to the handle from a prime mover-locked position, in which position the prime mover carriage is restrained from longitudinal movement with respect to the handle, to a range of prime mover-unlocked positions, in which positions longitudinal movement of the prime mover carriage with respect to the handle is substantially not restrained.

63. The atherectomy device of claim 62, further comprising a prime mover carriage lock for automatically restraining the prime mover carriage from longitudinal movement with respect to the handle when the prime mover carriage is moved longitudinally to the prime mover-locked position.

64. The atherectomy device of claim 63 wherein the prime mover carriage lock comprises a disengagable mechanical linkage between the prime mover carriage and the handle for releasably locking the prime mover carriage in the prime mover-locked position.

65. The atherectomy device of claim 64 wherein the disengagable mechanical linkage comprises a detent and a complementary member engageable with the detent.

66. The atherectomy device of claim 65 wherein the handle includes a housing having an elongated slot defined by opposing walls of the handle housing, and the carriage includes a shaft extending radially outwardly between the opposing walls of the elongated slot in the handle housing.

67. The atherectomy device of claim 66 wherein the detent is comprised of a narrowed portion in the elongated slot of the handle housing.

68. The atherectomy device of claim 67 wherein the shaft extending outwardly from the carriage has a diameter larger than the width of the narrowed portion in the elongated slot of the handle housing.

69. The atherectomy device of claim 67 wherein the shaft extending outwardly from the carriage includes a collar disposed about the shaft, the collar having a diameter that is larger than the width of the narrowed portion in the elongated slot of the handle housing.

70. The atherectomy device of claim 68 or 69 wherein the narrowed portion of the elongated slot is constructed so that when the shaft is urged into the narrowed portion of the elongated slot the narrowed portion resiliently widens to permit the shaft to pass therethrough so that the carriage becomes releasably locked in the prime mover-locked position.

71. The atherectomy device of claim 70 wherein the handle housing includes a relief slot extending from an end of the elongated slot.

72. The atherectomy device of claim 71 wherein the relief slot extends from the end of the elongated slot closest to the narrowed portion in the elongated slot.

73. The atherectomy device of claim 69 wherein the collar is made from a resilient material.

74. The atherectomy device of claim 69 wherein the collar is rotatable with respect to the shaft.

75. The atherectomy device of claim 64 wherein the disengagable mechanical linkage comprises a pair of interlocking members that are releasably engageable with each other.

76. The atherectomy device of claim 75 wherein one of the interlocking members comprises a tab extending proximally from the prime mover carriage, the tab having a radially extending shoulder, the other interlocking member being carried by the handle and having a complementary ridge for releasable engagement with the radially extending shoulder.

77. The atherectomy device of claim 76 wherein the interlocking member carried by the handle is secured directly to the handle.

78. The atherectomy device of claim 76, wherein the guide wire clamp is positioned within the handle to releasably clamp the guide wire.

79. The atherectomy device of claim 78 wherein the interlocking member carried by the handle is carried by a housing of the guide wire clamp which in turn is secured to the handle.

80. The atherectomy device of claim 76 wherein the radially extending shoulder extends radially inwardly from the tab.

81. The atherectomy device of claim 76 further comprising a pair of tabs extending proximally from the prime mover carriage, the tabs being located on opposite sides of the prime mover carriage.

82. The atherectomy device of claim 76 wherein the ridge carried by the other interlocking member is a generally annular ridge.

83. An atherectomy device comprising:
a handle;
a rotatable prime mover which is movable longitudinally with respect to the handle;
a rotatable drive shaft having a proximal end connected to the prime mover for rotation and longitudinal movement therewith;
a brake shoe which is selectively movable with respect to the prime mover from a brake shoe-released position to a brake shoe-engaged position where the brake shoe is operatively engaged with the prime mover to prevent rotation of the prime mover and the drive shaft; and
a prime mover carriage which is movable longitudinally with respect to the handle, the prime mover and the brake shoe being carried by the prime mover carriage.

84. The atherectomy device of claim 83 wherein the prime mover carriage carries a brake shoe biasing spring for biasing the brake shoe away from the prime mover.

85. The atherectomy device of claim 83 wherein the prime mover carriage carries a resilient O-ring for biasing the brake shoe away from the prime mover.

86. The atherectomy device of claim 83 wherein the prime mover comprises a compressed gas driven turbine having a turbine wheel disposed within a turbine wheel chamber.

87. The atherectomy device of claim 86 wherein the brake shoe includes a turbine wheel engaging surface, the turbine wheel engaging surface being positioned to define at least part of a wall of the turbine wheel chamber so that when compressed gas is supplied to the turbine wheel to rotate the turbine the compressed gas will exert pressure on the turbine wheel engaging surface of the brake shoe, thereby urging the brake shoe away from the turbine wheel.

88. The atherectomy device of claim 83 further comprising a brake shoe biasing mechanism for biasing the brake shoe away from the prime mover and a brake shoe engagement spring for overriding the brake shoe biasing mechanism and causing the brake shoe to move from its brake shoe-released position to its brake shoe-engaged position.

89. The atherectomy device of claim 83 further comprising a guide wire disposed within the drive shaft, the guide wire having a proximal portion extending from the proximal end of the drive shaft, and a clamp associated with the handle for releasably clamping the proximal portion of the guide wire.

90. The atherectomy device of claim 89 wherein the clamp is comprised of a pair of opposed clamping blocks, each having a clamping surface, and a clamp biasing mechanism for biasing at least one of the clamping surfaces toward the other to clamp the guide wire.

91. The atherectomy device of claim 90 wherein the clamp is movable from a guide wire-clamped position to a guide wire-released position, the atherectomy device including a clamp control tube for controlling the position of the clamp, the clamp control tube having a proximal end portion and a distal end portion, the distal end portion of the clamp control tube being operatively connected to the brake shoe.

92. The atherectomy. device of claim 91 wherein the clamp control tube is movable longitudinally from a range of positions where its proximal end portion is spaced from the clamping blocks to a position where its proximal end portion is wedged between the clamping blocks, moving the clamp to its guide wire-released position where the clamping surfaces of the clamping blocks are spaced apart sufficiently to release the guide wire.

93. The atherectomy device of claim 91 wherein the distal end portion of the clamp control tube includes a radially outwardly extending flange, the brake shoe including a central cavity capturing the radially outwardly extending flange.

94. The atherectomy device of claim 93 wherein the central cavity of the brake shoe is longitudinally longer than the flange of the clamp control tube, permitting limited longitudinal movement of the clamp control tube with respect to the brake shoe.

95. The atherectomy device of claim 90 wherein the clamp is movable from a guide wire-clamped position to a guide wire-released position, the atherectomy device including a clamp control rod for controlling the position of the clamp, the clamp control rod having a proximal end portion and a distal end portion, the distal end portion of the clamp control rod being operatively connected to the prime mover carriage.

96. An atherectomy device comprising:
 a handle;
 a rotatable prime mover disposed within the handle;
 a rotatable drive shaft having a proximal end connected to the prime mover for rotation therewith; and
 a brake shoe located within the handle, the brake shoe being selectively movable with respect to the prime mover from a brake shoe-released position to a brake shoe-engaged position where the brake shoe is operatively engaged with the prime mover to prevent rotation of the prime mover and the drive shaft.

97. The atherectomy device of claim 96 further comprising a brake shoe control mechanism for controlling the position of the brake shoe with respect to the prime mover.

98. The atherectomy device of claim 97 wherein the brake shoe control mechanism comprises a brake shoe biasing mechanism for biasing the brake shoe away from the prime mover, and a brake shoe engagement mechanism for overriding the brake shoe biasing mechanism and causing the brake shoe to move from its brake shoe-released position to its brake shoe-engaged position.

99. The atherectomy device of claim 98 further comprising a prime mover carriage which is movable longitudinally with respect to the handle, the prime mover carriage carrying the prime mover, the brake shoe and the brake shoe biasing mechanism.

100. The atherectomy device of claim 99 wherein the prime mover carriage is movable with respect to the handle from a prime mover-locked position, in which position the carriage and the prime mover are restrained from longitudinal movement with respect to the handle, to a range of prime mover unlocked positions, in which positions longitudinal movement of the carriage and the prime mover with respect to the handle are substantially unrestrained.

101. The atherectomy device of claim 100, further comprising a guide wire disposed within the drive shaft, the guide wire having a proximal portion extending from the proximal end of the drive shaft, and a clamp disposed within the handle for releasably clamping the proximal portion of the guide wire.

102. The atherectomy device of claim 101 wherein the clamp is comprised of a pair of opposed clamping blocks, each having a clamping surface, and a clamp biasing mechanism for biasing at least one of the clamping surfaces toward the other to clamp the guide wire.

103. The atherectomy device of claim 102 wherein the clamp includes a clamp housing having a slot in which the clamping blocks are disposed, the clamp housing maintaining alignment of the clamping blocks with respect to each other and with respect to the handle.

104. The atherectomy device of claim 102 wherein the clamp is movable from a guide wire-clamped position to a guide wire-released position, the atherectomy device including a clamp control mechanism for controlling the position of the clamp.

105. The atherectomy device of claim 104 wherein the clamp control mechanism includes a clamp control tube having a lumen for receiving the guide wire therethrough, the clamp control tube having a proximal end portion and a distal end portion, the distal end portion of the clamp control tube being operatively connected to the brake shoe.

106. The atherectomy device of claim 105 wherein the clamp control tube is movable longitudinally from a range of positions where its proximal end portion is spaced from the clamping blocks to a position where its proximal end portion is wedged between the clamping blocks, moving the clamp to its guide wire-released position where the clamping surfaces of the clamping blocks are spaced apart sufficiently to release the guide wire.

107. The atherectomy device of claim 106 wherein the prime mover carriage, the brake shoe, and the brake shoe engagement mechanism are positioned with respect to one another so that as the prime mover carriage is moved to its prime mover-locked position the brake shoe encounters the brake shoe engagement mechanism, which overrides the brake shoe biasing mechanism, causing the brake shoe to move into its brake shoe-engaged position, thus preventing rotation of the prime mover.

108. The atherectomy device of claim 107 wherein the brake shoe engagement mechanism includes a spring element positioned so that as soon as the brake shoe engages the prime mover, further advancement of the prime mover carriage into its prime mover-locked position causes the brake shoe to compress the spring element of the brake shoe engagement mechanism and to wedge the proximal end portion of the clamp control tube between the clamping blocks, thereby moving the clamp into its guide wire-released position.

109. The atherectomy device of claim 105 wherein the distal end portion of the clamp control tube includes a radially outwardly extending flange, the brake shoe including a central cavity capturing the radially outwardly extending flange.

110. The atherectomy device of claim 109 wherein the central cavity of the brake shoe is longitudinally longer than the flange of the clamp control tube, permitting limited longitudinal movement of the clamp control tube with respect to the brake shoe.

111. The atherectomy device of claim 110 wherein the central cavity of the brake shoe is at least about 1 mm longer than the flange of the control tube, permitting at least about 1 mm of longitudinal movement of the control tube with respect to the brake shoe.

112. An atherectomy device comprising:
a handle;
a rotatable turbine disposed within the handle;
a rotatable drive shaft having a proximal end connected to the turbine for rotation therewith; and
a brake shoe located within the handle, the brake shoe being longitudinally movable with respect to the turbine from a brake shoe-released position to a brake shoe-engaged position where the brake shoe is operatively engaged with the turbine to prevent rotation of the turbine and the drive shaft.

113. The atherectomy device of claim 112 further comprising a guide wire disposed within the drive shaft, the guide wire having a proximal portion extending from the proximal end of the drive shaft, and a guide wire clamp disposed within the handle for releasably clamping the proximal portion of the guide wire.

114. The atherectomy device of claim 113 further comprising a clamp control tube for controlling the position of the clamp, the clamp control tube having a distal end portion operatively connected to the brake shoe for longitudinal movement therewith.

115. The atherectomy device of claim 114 wherein the distal end portion of the clamp control tube includes a radially outwardly extending flange, the brake shoe including a central cavity capturing the radially outwardly extending flange.

116. The atherectomy device of claim 115 wherein the central cavity of the brake shoe is longitudinally longer than the flange of the clamp control tube, permitting limited longitudinal movement of the clamp control tube with respect to the brake shoe.

117. The atherectomy device of claim 112 further comprising a brake shoe control mechanism for controlling the position of the brake shoe with respect to the turbine.

118. The atherectomy device of claim 117 wherein the brake shoe control mechanism comprises a brake shoe biasing mechanism for biasing the brake shoe away from the turbine, and a brake shoe engagement mechanism for overriding the brake shoe biasing mechanism and causing the brake shoe to move from its brake shoe-released position to its brake shoe-engaged position.

119. The atherectomy device of claim 118 further comprising a turbine carriage which is movable longitudinally with respect to the handle, the turbine carriage carrying the turbine, the brake shoe and the brake shoe biasing mechanism.

120. An atherectomy device comprising:
a handle;
a rotatable turbine having a turbine wheel, the turbine being disposed within the handle;
a rotatable drive shaft having a proximal end connected to the turbine for rotation therewith; and
a brake shoe located within the handle, the brake shoe being longitudinally movable with respect to the turbine wheel from a brake shoe-released position to a brake shoe-engaged position where the brake shoe is operatively engaged with the turbine wheel to prevent rotation of the turbine and the drive shaft.

121. The atherectomy device of claim 120 further comprising a brake shoe biasing spring for biasing the brake shoe away from the turbine wheel.

122. The atherectomy device of claim 121 further comprising a brake shoe engagement spring for overriding the brake shoe biasing spring and causing the brake shoe to move from its brake shoe-released position to its brake shoe-engaged position.

123. The atherectomy device of claim 122 further comprising an abutment disposed within the handle, the abutment being positioned between the brake shoe and the brake shoe engagement spring.

124. The atherectomy device of claim 121 further comprising a turbine carriage which is movable longitudinally with respect to the handle, the turbine carriage carrying the turbine, the brake shoe and the brake shoe biasing spring.

125. An atherectomy device comprising:
a handle;
a rotatable prime mover;
a prime mover carriage carrying the prime mover, the prime mover carriage being movable longitudinally with respect to the handle from a prime mover-locked position, in which position the prime mover carriage is restrained from longitudinal movement with respect to the handle, to a range of prime mover-unlocked positions, in which positions longitudinal movement of the prime mover carriage with respect to the handle is substantially not restrained;
a rotatable drive shaft having a proximal end connected to the prime mover for rotation and longitudinal movement therewith; and
a prime mover carriage lock for automatically restraining the prime mover carriage from longitudinal movement with respect to the handle when the prime mover carriage is moved longitudinally to the prime mover-locked position.

126. The atherectomy device of claim 125 wherein the prime mover carriage lock comprises a disengagable mechanical linkage between the prime mover carriage and the handle for releasably locking the prime mover carriage in the prime mover-locked position.

127. The atherectomy device of claim 126 wherein the disengagable mechanical linkage comprises a detent and complementary member engageable with the detent.

128. The atherectomy device of claim 127 wherein the handle includes a housing having an elongated slot defined by opposing walls of the handle housing, and the carriage includes a shaft extending radially outwardly between the opposing walls of the elongated slot in the handle housing.

129. The atherectomy device of claim 128 wherein the detent is comprised of a narrowed portion in the elongated slot of the handle housing.

130. The atherectomy device of claim 129 wherein the shaft extending outwardly from the carriage has a diameter larger than the width of the narrowed portion in the elongated slot of the handle housing.

131. The atherectomy device of claim 129 wherein the shaft extending outwardly from the carriage includes a collar disposed about the shaft, the collar having a diameter that is larger than the width of the narrowed portion in the elongated slot of the handle housing.

132. The atherectomy device of claim 130 or 131 wherein the narrowed portion of the elongated slot is constructed so that when the shaft is urged into the narrowed portion of the elongated slot the narrowed portion resiliently widens to permit the shaft to pass therethrough so that the carriage becomes releasably locked in the prime mover-locked position.

133. The atherectomy device of claim 132 wherein the handle housing includes a relief slot extending from an end of the elongated slot.

134. The atherectomy device of claim 133 wherein the relief slot extends from the end of the elongated slot closest to the narrowed portion in the elongated slot.

135. The atherectomy device of claim 131 wherein the collar is made from a resilient material.

136. The atherectomy device of claim 131 wherein the collar is rotatable with respect to the shaft.

137. The atherectomy device of claim 126 wherein the disengagable mechanical linkage comprises a pair of interlocking members that are releasably engageable with each other.

138. The atherectomy device of claim 137 wherein one of the interlocking members comprises a tab extending proximally from the prime mover carriage, the tab having a radially extending shoulder, the other interlocking member being carried by the handle and having a complementary ridge for releasable engagement with the radially extending shoulder.

139. The atherectomy device of claim 138 wherein the interlocking member carried by the handle is secured directly to the handle.

140. The atherectomy device of claim 138 further comprising a guide wire disposed within the drive shaft and a guide wire clamp positioned within the handle to releasably clamp the guide wire.

141. The atherectomy device of claim 140 wherein the interlocking member carried by the handle is carried by a housing of the guide wire clamp which in turn is secured to the handle.

142. The atherectomy device of claim 138 wherein the radially extending shoulder extends radially inwardly from the tab.

143. The atherectomy device of claim 138 further comprising a pair of tabs extending proximally from the prime mover carriage, the tabs being located on opposite sides of the prime mover carriage.

144. The atherectomy device of claim 138 wherein the ridge carried by the other interlocking member is a generally annular ridge.

145. An atherectomy device comprising:
a handle housing;
a rotatable prime mover movable longitudinally with respect to the handle housing;
a rotatable drive shaft having a proximal end connected to the prime mover for rotation and longitudinal movement therewith;
a guide wire disposed within the drive shaft, the guide wire having a longitudinal axis and a proximal portion extending proximally from the proximal end of the drive shaft; and
a clamp disposed within the handle housing for releasably clamping the proximal portion of the guide wire, the clamp being comprised of a pair of opposed clamping blocks, each having a clamping surface, and at least one clamp biasing spring for biasing at least one of the clamping surfaces toward the other to clamp the guide wire.

146. The atherectomy device of claim 145 wherein the clamp biasing spring comprises a resilient collar encircling the clamping blocks, the size and shape of the clamping blocks and the resilient collar being selected so that the resilient collar biases the clamping blocks toward each other to clamp the guide wire between the clamping surfaces.

147. The atherectomy device of claim 146 wherein the handle housing is sized and shaped with respect to the collar to permit manual compression of the collar to a shape in which the collar does not bias the clamping blocks toward each other.

148. The atherectomy device of claim 147 wherein the handle housing substantially surrounds the collar, the handle housing including at least one opening aligned with the collar to permit manual compression of the collar.

149. The atherectomy device of claim 148 wherein the handle housing includes a pair of openings aligned with the collar to permit manual compression of the collar.

150. The atherectomy device of claim 146 wherein the clamp includes a clamp housing having a slot in which the clamping blocks are disposed, the clamp housing maintaining alignment of the clamping blocks with respect to each other and with respect to the resilient collar, the handle housing and the guide wire.

151. The atherectomy device of claim 146 wherein the resilient collar is comprised of a pair of generally semicircular bands.

152. The atherectomy device of claim 145 wherein each clamping block has a clamping surface and a spring-engaging surface, the clamping surfaces of the two clamping blocks being generally parallel to each other and to the longitudinal axis of the guide wire.

153. The atherectomy device of claim 152 wherein the clamping surfaces of the two clamping blocks are oriented at an acute angle to a plane which contains or is parallel to the guide wire's longitudinal axis, the plane extending from the spring-engaging surface of one of the clamping blocks to the spring-engaging surface of the other clamping block.

154. The atherectomy device of claim 153 wherein the drive shaft has a primary direction of rotation selected so that frictional torque conveyed by friction from the drive shaft to the guide wire urges the guide wire to rotate in a direction that increases the clamping force exerted by the clamping blocks on the guide wire.

155. The atherectomy device of claim 145 wherein each clamping block includes a radially central end and a radially peripheral end.

156. The atherectomy device of claim 155 wherein each clamping block has a recess near its central end, the recess being formed within the clamping block to define a clamping foot at the central end of the clamping block, the clamping surface being carried by the clamping foot.

157. The atherectomy device of claim 156 wherein the opposed clamping blocks are positioned with respect to each other so that the clamping foot of one clamping block is received in the recess of the other clamping block.

158. The atherectomy device of claim 157 wherein the clamping surface of each clamping block is located on a dorsal surface of the foot of the clamping block.

159. The atherectomy device of claim 158 wherein at least one of the clamping blocks includes one or more slots near its peripheral end for receiving at least one clamp biasing spring which urges the peripheral ends of the clamping blocks away from each other, thereby moving the clamping feet and the clamping surfaces toward each other.

160. The atherectomy device of claim 159 wherein the clamping surfaces of the two clamping blocks are generally parallel to each other and to the longitudinal axis of the guide wire.

161. The atherectomy device of claim 160 wherein the clamping surfaces of the two clamping blocks are oriented at an acute angle to a plane which contains or is parallel to the guide wire's longitudinal axis, the plane extending from the radially peripheral end of one of the clamping blocks to the radially peripheral end of the other clamping block.

162. The atherectomy device of claim 161 wherein the drive shaft has a primary direction of rotation selected so that frictional torque conveyed by friction from the drive shaft to the guide wire urges the guide wire to rotate in a direction that increases the clamping force exerted by the clamping blocks on the guide wire.

163. The atherectomy device of claim 158 wherein the handle housing is sized and shaped with respect to the clamp and its clamping blocks to permit application of manual pressure on at least one of the clamping blocks, thereby compressing one or more of the clamp biasing springs and releasing the guide wire from the clamp.

164. The atherectomy device of claim 163 wherein the handle housing substantially surrounds the clamp, the handle housing including a pair of openings aligned with the clamping blocks to permit manual compression of one or more of the clamp biasing springs by simultaneously pushing on both of the clamping blocks.

165. The atherectomy device of claim 145 or 164 wherein at least one of the clamping blocks includes a peripheral end extending outwardly through an opening in the handle housing to facilitate manual compression of one or more of the clamp biasing springs.

166. The atherectomy device of claim 145 wherein the clamp is movable from a guide wire-clamped position to a guide wire-released position, the atherectomy device including a clamp control mechanism for controlling the position of the clamp.

167. The atherectomy device of claim 166 wherein the clamp control mechanism includes a clamp control tube having a lumen for receiving the guide wire therethrough, the clamp control tube having a distal end portion and a proximal end portion.

168. The atherectomy device of claim 167 wherein the clamp control tube is longitudinally movable from a range of positions where its proximal end portion is spaced from the clamping blocks to a position where its proximal end portion is wedged between the clamping blocks, moving the clamp to its guide wire-released position where the clamping surfaces of the clamping blocks are spaced apart sufficiently to release the guide wire.

169. The atherectomy device of claim 168 further comprising a brake shoe which is longitudinally movable with respect to the prime mover from a brake shoe-released position to a brake shoe-engaged position where the brake shoe is operatively engaged with the prime mover to prevent rotation of the prime mover and the drive shaft.

170. The atherectomy device of claim 169 further comprising a prime mover carriage which is movable longitudinally with respect to the handle, both the prime mover and the brake shoe being carried by the prime mover carriage.

171. The atherectomy device of claim 169 wherein the distal end portion of the clamp control tube is operatively connected to the brake shoe for longitudinal movement therewith.

172. The atherectomy device of claim 171 wherein the distal end portion of the clamp control tube includes a radially outwardly extending flange, the brake shoe including a central cavity capturing the radially outwardly extending flange.

173. The atherectomy device of claim 172 wherein the central cavity of the brake shoe is longitudinally longer than the flange of the clamp control tube, permitting limited longitudinal movement of the clamp control tube with respect to the brake shoe.

174. The atherectomy device of claim 173 wherein the central cavity of the brake shoe is at least about 1 mm longer than the flange of the control tube, permitting at least about 1 mm of longitudinal movement of the control tube with respect to the brake shoe.

175. The atherectomy device of claim 166 further comprising a prime mover carriage which is movable longitudinally with respect to the handle, the prime mover being carried by the prime mover carriage.

176. The atherectomy device of claim 175 wherein the clamp control mechanism is operatively connected to the prime mover carriage.

177. The atherectomy device of claim 145 wherein the clamp includes a clamp housing having a slot in which the clamping blocks are disposed, the clamp housing maintaining alignment of the clamping blocks with respect to each other and with respect to the handle housing and the guide wire.

178. The atherectomy device of claim 145 wherein the clamping surfaces are provided with a diamond coating to provide adequate engagement of the clamping surfaces with the guide wire.

179. The atherectomy device of claim 145 wherein the clamping surfaces are provided with a coating of material which provides a higher coefficient of friction between the coating material and the guide wire than the coefficient of friction between the guide wire and the material from which the clamping blocks are made.

180. An atherectomy device comprising:

a handle housing;

a turbine carriage disposed within the handle housing, the turbine carriage carrying a rotatable turbine including a turbine wheel, the turbine carriage being movable longitudinally within the handle housing from a range of turbine carriage-unlocked positions to a turbine carriage-locked position, in which position the turbine carriage, together with the rotatable turbine, is restrained from longitudinal movement with respect to the handle housing;

a rotatable drive shaft having a proximal end connected to the turbine for rotation and longitudinal movement therewith;

a brake shoe disposed within the handle housing, the brake shoe being selectively movable from a brake shoe-released position to a brake shoe engaged position in which position the brake shoe is engaged with the turbine wheel to prevent rotation of the turbine;

the brake shoe being automatically moved to the brake shoe-engaged positions whenever the turbine carriage is moved to the turbine carriage-locked position, and the brake shoe being automatically moved to the brake shoe-released position whenever the turbine carriage is moved to a range of turbine carriage-unlocked position;

a guide wire disposed within the drive shaft and having a proximal portion extending from the proximal end of the drive shaft;

a guide wire clamp for releasably clamping the proximal portion of the guide wire, the clamp being comprised of a pair of opposed clamping blocks, each having a clamping surface, and a resilient circumferential collar disposed around the clamping blocks for biasing the clamping blocks toward each other in order to clamp the guide wire between the clamping surfaces of the clamping blocks; and a clamp control tube being movable from a range of positions where it is spaced from the clamping blocks to a position where it is wedged between the clamping blocks, thereby spacing the clamping surfaces of the clamping blocks away from each other to release the guide wire from the clamp;

the clamp control tube, the brake shoe and the turbine carriage being operatively interconnected so that when the turbine carriage is moved into its turbine carriage-locked position the clamp control tube becomes wedged between the clamping blocks, releasing the guide wire from the clamp; and when the turbine carriage is moved into its range of turbine carriage-unlocked positions the clamp control tube is moved away from the clamping blocks so that the guide wire is clamped between the clamping blocks of the guide wire clamp.

181. The atherectomy device of claim 180 wherein the clamp control tube, the brake shoe and the turbine carriage are operatively interconnected so that as the turbine carriage is moved toward its turbine carriage-locked position the brake shoe reaches its brake shoe-engaged position preventing rotation of the turbine before the clamp control tube is wedged between the clamping blocks, thereby releasing the guide wire from the clamp.

182. An atherectomy device comprising:

a handle housing;

a turbine carriage disposed within the handle housing, the turbine carriage carrying a rotatable turbine and being movable longitudinally within the handle housing;

a rotatable drive shaft having a proximal end connected to the turbine for rotation and longitudinal movement therewith; and a brake shoe disposed within the handle housing;

the turbine carriage being movable longitudinally within the handle housing from a position where the turbine is spaced away from the brake shoe to a position where the turbine engages the brake shoe to prevent rotation of the turbine.

* * * * *